(12) United States Patent
Van Den Hazel et al.

(10) Patent No.: US 6,958,388 B2
(45) Date of Patent: Oct. 25, 2005

(54) INTERFERON GAMMA POLYPEPTIDE VARIANTS

(75) Inventors: Bart Van Den Hazel, Olufsvej (DK); Anne Dam Jensen, Svanevej (DK); Frank Bech. Nygaard, Strandvej (DK); Kim Vilbour Andersen, Broenshoej (DK)

(73) Assignee: Maxygen, ApS, Horsholm (DK)

( * ) Notice: Subject to any disclaimer, the term of this patent is extended or adjusted under 35 U.S.C. 154(b) by 63 days.

(21) Appl. No.: 10/195,707

(22) Filed: Jul. 15, 2002

(65) Prior Publication Data

US 2003/0133907 A1 Jul. 17, 2003

Related U.S. Application Data

(63) Continuation-in-part of application No. 10/116,273, filed on Apr. 4, 2002.
(60) Provisional application No. 60/356,321, filed on Feb. 11, 2002, provisional application No. 60/289,398, filed on May 7, 2001, and provisional application No. 60/282,254, filed on Apr. 6, 2001.

(51) Int. Cl.$^7$ .................. C07K 17/00; A61K 38/21; C12P 21/04
(52) U.S. Cl. ............... 530/351; 424/85.5; 424/85.4; 435/69.51
(58) Field of Search .............. 424/85.5, 85.4; 530/351; 435/69.51

(56) References Cited

U.S. PATENT DOCUMENTS

| | | | |
|---|---|---|---|
| 4,457,867 A | 7/1984 | Ishida |
| 4,588,585 A | 5/1986 | Mark et al. |
| 4,604,284 A | 8/1986 | Kung et al. |
| 4,695,623 A | 9/1987 | Stabinsky |
| 4,727,138 A | 2/1988 | Goeddel et al. |
| 4,758,656 A | 7/1988 | Itoh et al. |
| 4,762,791 A | 8/1988 | Goeddel et al. |
| 4,832,959 A | 5/1989 | Engels et al. |
| 4,835,256 A | 5/1989 | Taniguchi et al. |

(Continued)

FOREIGN PATENT DOCUMENTS

| | | |
|---|---|---|
| CA | 2096532 | 5/1992 |
| EP | 077 670 B1 | 4/1983 |
| EP | 088 540 A2 | 9/1983 |
| EP | 089 676 A2 | 9/1983 |
| EP | 098 110 A2 | 1/1984 |
| EP | 110 044 A1 | 6/1984 |
| EP | 146 354 A2 | 6/1985 |
| EP | 158 198 A1 | 10/1985 |
| EP | 170 917 B1 | 2/1986 |
| EP | 219 781 A2 | 4/1987 |
| EP | 229 108 B1 | 7/1987 |
| EP | 256 424 B1 | 8/1987 |
| EP | 236 987 B1 | 9/1987 |
| EP | 237 019 A2 | 9/1987 |
| EP | 306 870 A2 | 3/1989 |
| EP | 121 157 B1 | 6/1989 |
| EP | 145 174 B1 | 9/1989 |
| EP | 370 205 A2 | 5/1990 |
| EP | 446 582 B1 | 9/1991 |
| EP | 546 099 B1 | 10/1994 |
| EP | 795 332 A2 | 9/1997 |
| EP | 593 868 B1 | 4/1998 |
| EP | 860 442 A1 | 8/1998 |
| WO | 92/08737 A1 | 11/1991 |
| WO | 92/22310 A1 | 6/1992 |
| WO | 99/03887 A1 | 7/1998 |
| WO | 99/67291 A2 | 6/1999 |
| WO | 01/23006 A1 | 9/2000 |
| WO | 01/36001 A2 | 11/2000 |

OTHER PUBLICATIONS

Alberts et al., Molecular Biology of the Cell, 1989.*

Wetzel, et al., *Mutational Analysis of the C–terminus of Human Interferon–γ*, Protein Engineering, 3:(7) pp. 611–623(1990).

Arakawa, et al , *Role of Polycationic C–terminal Portion in the Structure and Activity of Recombinant Human Interferon–γ\**, The Journal of Biological Chemistry, 261 (18), Jun. 25, pp. 8534–8539 (1986).

Arakawa, et al., *Structure and Activity of Glycosylated Human Interferon–γ* Journal of Interferon Research, 6:687–695 (1986).

Bulleid, et al , *Source of heterogeneity in secreted interferon–γ* Biochem, J. 268:777–781 (1990).

(Continued)

Primary Examiner—Janet Andres
(74) Attorney, Agent, or Firm—Donald J. Pochopien; Sharon Fujita; McAndrews, Held & Malloy

(57) ABSTRACT

When interferon gamma (IFNG) is produced in mammalian cell lines a heterogenous population of IFNG polypeptides is obtained due to C-terminal processing of the IFNG polypeptide. Clearly, this constitutes a severe problem in that valuable polypeptide material is lost and, further, it is necessary to carry out time-consuming and cumbersome purification in order to obtain a homogenous population of active IFNG polypeptides having the desired length. It has now been found that an IFNG fragment containing 132 amino acid residues (truncated at the nucleotide level by introducing a stop-codon after the codon encoding amino acid residue no. 132) does not undergo C-terminal truncation or, at least, is not significantly C-terminally truncated. Furthermore, as the IFNG fragment containing 132 amino acid residues is active, this opens up the possibility of producing a homogenous active IFNG polypeptide in eukaryotic host cells, such as CHO cells. More particularly, the present invention relates to an IFNG polypeptide variant exhibiting IFNG activity and having the amino acid sequence shown in SEQ ID NO:12. In a highly preferred embodiment of the invention, the variant comprises at least one further modification, such as 1–10 further modifications, relative to the amino acid sequence shown in SEQ ID NO:12. A particular preferred further modification is E38N+S40T.

57 Claims, 6 Drawing Sheets

U.S. PATENT DOCUMENTS

| | | |
|---|---|---|
| 4,845,196 A | 7/1989 | Cowling |
| 4,855,238 A | 8/1989 | Gray et al. |
| 4,897,471 A | 1/1990 | Stabinsky |
| 4,898,931 A | 2/1990 | Itoh et al. |
| 4,904,584 A | 2/1990 | Shaw |
| 4,921,698 A | 5/1990 | Shirai et al. |
| 4,925,793 A | 5/1990 | Goeddel et al. |
| 4,929,554 A | 5/1990 | Goeddel et al. |
| 4,944,941 A | 7/1990 | Ammann |
| 4,966,843 A | 10/1990 | McCormick et al. |
| 4,980,455 A | 12/1990 | Sakaguchi et al. |
| 5,004,689 A | 4/1991 | Fiers et al. |
| 5,041,376 A | 8/1991 | Gething et al. |
| 5,096,705 A | 3/1992 | Goeddel et al. |
| 5,109,120 A | 4/1992 | Ueno et al. |
| 5,157,004 A | 10/1992 | Sakaguchi et al. |
| 5,362,490 A | 11/1994 | Kurimoto et al. |
| 5,376,567 A | 12/1994 | McCormick et al. |
| 5,382,657 A | 1/1995 | Karasiewicz et al. |
| 5,518,899 A | 5/1996 | Kurimoto et al. |
| 5,541,293 A | 7/1996 | Stabinsky |
| 5,554,515 A | 9/1996 | Kurimoto et al. |
| 5,574,137 A | 11/1996 | Gray et al. |
| 5,582,824 A | 12/1996 | Goeddel et al. |
| 5,595,888 A | 1/1997 | Gray et al. |
| 5,661,009 A | 8/1997 | Stabinsky |
| 5,672,692 A | 9/1997 | Kurimoto et al. |
| 5,690,925 A | 11/1997 | Gray et al. |
| 5,711,944 A | 1/1998 | Gilbert et al. |
| 5,723,121 A | 3/1998 | Takenaga et al. |
| 5,738,846 A | 4/1998 | Greenwald et al. |
| 5,747,646 A | 5/1998 | Hakimi et al. |
| 5,770,191 A * | 6/1998 | Johnson et al. ............ 424/85.5 |
| 5,792,834 A | 8/1998 | Hakimi et al. |
| 6,042,822 A | 3/2000 | Gilbert et al. |
| 6,046,034 A | 4/2000 | Waschutza et al. |
| 6,120,762 A | 9/2000 | Johnson et al. |
| 6,497,871 B1 | 12/2002 | Gray et al. |

OTHER PUBLICATIONS

Cantell, et al, *Differential Inactivation of Interferon by a Protease from Human Granulocytes*, Journal of Interferon Research 12:177–183 (1992).

Castro, et al., *The macroheterogeneity of recombinant human interferon–γ produced by Chinese–hamster ovary cells is affected by the protein and lipid content of the culture medium*, Biotechnol. Appl. Biochem., 21:87–100 (1995).

Curling, et al., *Recombinant human interferon–γ Differences in glycosylation and proteolytic processing lead to heterogeneity in batch culture*, Biochem. J., 272:333–337 (1990).

Devos, et al., *Molecular cloning of human immune interferon cDNA and its expression in eukaryatic cells*, Nucleic Acids Research, 10(8), 2487–2501, Nov. 8, 1982.

Ealick, et al., *Three–Dimensional Structure of Recombinant Human Interferon–γ* Science, 252:698–702 (1991).

Farrar, et al., *The Molecular Cell Biology of Interferon–γ and its Receptor*, Annu. Rev. Immunol. 11:572–611 (1993).

Gray, et al., *Structure of the human immune interferon gene*, Nature, 298:859–863 (Aug. 1992).

Griggs, et al., *The N–terminus and C–Terminus of IFN–γ Are Binding Domains for Cloned Soluble IFN–γReceptor*. The Journal of Immunology, 149 (2) 517–520 (Jul. 15, 1992).

Gu, et al., *Improvement of Interferon–γ Sialylation in Chinese Hamster Ovary Cell Culture by Feeding of N–Acetylmannosamine*, Biotechnology & Bioengineering, 58 (6) 642–648 (1998).

Haelewn, et al., *Interaction of truncated human interferon γ variants with the interferon γ receptor: crucial importance of Arg–129* , Biochem. J., 324, 591–595 (1997).

Harmon, et al., *Rapid Monitoring of Site–Specific Glycosylation Microheterogeneity of Recombinant Human Interferon–γ*, Anal. Chem., 68 (9) 1465–1473 (1996).

Hogrefe, et al., *Amino Terminus Is Essential to the Structural Integrity of Recombinant Human Interferon–γ* The Journal of Biological Chemistry, 264 (21) 12179–86 (1989).

Hooker, et al., *Constraints on the Transport and Glycosylation of Recombinant IFN–γ in Chinese Hamster Ovary and Insect Cells*. Biotechnology & Bioengineering, 63 (5) 559–572 (1999).

Hsu, et al., *Structure and Activity of Recombinant Human Interferon–γ Analogs*, Journal of Interferon Research, 6:663–670 (1986).

James, et al., *N–Glycosylation of Recombinant Human Interferon–γ Produced in Different Animal Expression Systems*, Bio/Technology, 13–592–96 (Jun. 13, 1995).

Kita, et al., *Characterization of a Polyethylene Glycol Conjugate of Recombinant Human Interferon–γ* Drug Design and Delivery, 6:157–167 (1990).

Kontsek, et al., *Engineered Acid–Stabile Human Interferon Gamma*, Cytokine, 12 (6) 708–710 (Jun. 2000.

Lander, et al., *Design, Characterization, and Structure of a Biologically Active Single–chain Mutant of Human IFN–γ*, J. Mol. Biol., 299:169–179 (2000).

Leinikki, et al., *Reduced Receptor Binding by a Human Interferon–γ Fragment Lacking[ ] Carboxyl–TerminalAmino Acids*, Journal of Immunology, 139 (10) 3360–3366 (1987).

Littman, et al., *Binding of Unglycosylated and Glycosylated Human Recombinant Interferon–γ to Cellular Receptors*, Journal of Interferon Research. 5: 471–476 (1985).

Lord, et al., *Functional Domains of Human Interferon Gamma Probed With Antipeptide Antibodies*, Molecular Immunology, 26 (7) 637–640 (1989).

Luk, et al., *Structure–Function Analysis of the Human Interferon γ*, The Journal of Biological Chemistry, 265 (22) 13314–13319 (1990).

Lundell, et al., *Importance of the Loop Connecting A and B Helices of Human Interferon–γ in Recognition by Interferon–γ Receptor**, The Journal of Biological Chemistry, 269 (23) 16159–16162.

Lundell, et al., *Structural Elements Required for Receptor Recognition of Human Interferon–Gamma*, Pharmac. Ther. 64:1–21 (1994).

Lundell, et al , *The carboxyl–terminal region of human interferon γ is important for biological activity: mutagenic and NMR analysis*, Protein Engineering. 4 (3) 335–341 (1991).

Lunn, et al., *A point mutation of human interferon γ abolishes receptor recognition*, Protein Engineering, 5 (3) 253–257 (1992).

Lunn, et al., *A point mutation that decreases the thermal stability of human interferon γ*, Protein Engineering, 5 (3) 249–257 (1992).

Mortz, et al., *Mass spectrometric characterization of glycosylated interferon–γ variants separated by gel electrophoresis*, Electrophoresis, 17:926–931 (1996).

Nishi, et al., *Cloning and Expression of a Novel Variant of Human Interferon–γ cDNA*, J. Biochem, 97 (1) 153–159 (1985).

Nyberg, et al., *Metabolic Effects on Recombinant Interferon–γ Glycosylation in Continuous Culture of Chinese Hamster Ovary Cells*. Biotechnology & Bioengineering, 62 (3) 336–347 (1999).

Oliver, et al., *The use of electrospray ionization MS to determine the structure of glycans in intact glycoproteins*. Biochem Mass Spectro., 24:917–927 (1996).

Pan, et al., *Structural characterization of human interferon γ*, FEBS 145–149 (1987).

Rinderknecht, et al., *Natural Human Interferon–γ*, Journal of Biological Chemistry, 259 (11) 6790–6797 (1984).

Riske, et al , *Characterization of Human Interferon–γ and Human Interleukin–2 from Recombinant Mammalian Cell Lines and Peripheral Blood Lympocytes*Lymphokine and Cytokine Research, 10 (3) 213–218, (1991).

Sakaguchi, et al., *Human interferon–γ lacking 23 COOH–terminal amino acids is biologically active*, FEBS Letters, 230 (1,2) 201–204 (Mar. 1988).

Sano, et al., *Structural Characterization of Recombinant Human Interferon–Gammas Derived from Two Different Mammalian Cells*, Microbiol Immunol.. 32 (5) 499–510 (1988).

Sareneva, et al., *Biosynthesis and N–glycosylation of human interferon–γ Asn25 and Asn97 differ markedly in how efficiently they are glycosylated and in their oligosaccharide composition*, Eur. J. Biochem., 242:191–200 (1996).

Sareneva, et al., *N–glycosylation of human interferon–γ glycans at Asn–25 are critical for protease resistance*, Biochem. J. 308;9–14 (1995).

Sareneva, et al., *Role of N–glycosylation in the synthesis, dimerization and secretion of human interferon–γ*. Biochem. J., 303:831–840 (1994).

Sareneva. et al., *Effect of Carbohydrates on the Pharmacokinetics of Human Interferon–γ*, Journal of Interferon Research, 13:267–269 (1993).

Seelig, et al., *Evidence for a Polypepide Segment on the Carboxyl Terminus of Recombinant Human γ Interferon Involved in Expression of Biological Activity*, Biochemistry, 27 (6) 1981–1987 (1988).

Slodowski, et al., *Carboxy–terminal trunecaed rhuIFN–γ with a substitution of Gln133 o Ser132 to leucine leads to higher biological activity than in the wild type*, Euro. J. Biochem, 202:1133–1140 (1991).

Subramaniam, et al., *The Carboxyl Terminus of Interferon–γContains a Functional Polybasic Nuclear Localization Sequence*, Journal of Biological Chemistry, 274 (1) 403–407 (1999).

Tang, et al., *Studies on the PEGylation of Protein at a Specific Site: Sulthydryl–PEGylation of 97 Cys–INF–γ*, Acta Biochimica et Biophysica Sinica, 28 (3) 1–5 (May, 1996).

Tang, et al., *Cloning and structure of the human immune interferon–γ chromosomal gene*, The EMBO Journal, 1 (8) 953–958 (1982).

Trousdale, et al., *Human Alpha and Gamma Interferon Analogs in Rabbits with Herpetic Keratitis*, Invest Ophth. & Vis. Sci., 26 (9) 1244–1251 (1985).

Waschütza, et al., *Interferon–γvariants with deletions in the AB surface loop*, Eur. J. Biochem., 256:303–309 (1998).

Wetzel, et al., *Mutations in Human Interferon Gamma Affecting Inclusion Body Formation Identified by a General Immunochemical Screen*, Bio/Technology, 9:731–737 (1991).

Zhang, et al., *Quantitative analysis and process monitoring of site–specific glycosylation microheterogeneity in recombinant human interferon–γ from Chinese hamster ovary cell culture by hydrophilic interaction chromatography*, Journal of Chromatogr. B, 712:73–82 (1998).

Ziesche, et al., *A Preliminary Study of Long–Term Treatment with Interferon Gamma–1b and Low–Dose Prednisolone in Patients with Idiopathic Pulmonary Fibrosis*, The New England Journal of Medicine, 341 (7) 1264–1269 (1999).

* cited by examiner

INTERFERON GAMMA POLYPEPTIDE VARIANTS

This application is a continuation-in-part of U.S. Ser. No. 10/116,273, filed Apr. 4, 2002; which claims priority from each of U.S. Ser. No. 60/356,321, filed Feb. 11, 2002; U.S. Ser. No. 60/289,398, filed May 7, 2001; and U.S. Ser. No. 60/282,254, filed Apr. 6, 2001.

FIELD OF THE INVENTION

The present invention relates to novel interferon gamma polypeptide variants having interferon gamma (IFNG) activity, methods for their preparation, pharmaceutical compositions comprising the polypeptide variants and their use in the treatment of diseases, in particular for the treatment of interstitial pulmonary diseases, such as idiopathic pulmonary fibrosis.

BACKGROUND OF THE INVENTION

Interferon gamma (IFNG) is a cytokine produced by T-lymphocytes and natural killer cells and exists as a homodimer of two noncovalently bound polypeptide subunits. The mature form of each dimer comprises 143 amino acid residues (shown in SEQ ID NO:17), the precursor form thereof includes 166 amino acid residues (shown in SEQ ID NO:18).

Each subunit has two potential N-glycosylation sites (Aggarwal et al., Human Cytokines, Blackwell Scientific Publications, 1992) at positions 25 and 97. Depending on the degree of glycosylation the molecular weight of IFNG in dimer form is 34–50 kDa (Farrar et al., Ann. Rev. Immunol, 1993, 11:571–611).

The primary sequence of wild-type human IFNG (huIFNG) was reported by Gray et al. (Nature 298:859–863, 1982), Taya et al. (EMBO J. 1:953–958, 1982), Devos et al. (Nucleic Acids Res. 10:2487–2501, 1982) and Rinderknecht et al. (J. Biol. Chem. 259:6790–6797, 1984), and in EP 0 077 670, EP 0 089 676 and EP 0 110 044. The 3D structure of huIFNG was reported by Ealick et al. (Science 252:69–702, 1991).

Various naturally-occurring or mutated forms of the IFNG subunit polypeptides have been reported, including one comprising a Cys-Tyr-Cys N-terminal amino acid sequence (positions (−3)–(−1) relative to SEQ ID NO:17), one comprising an N-terminal methionine (position −1 relative to SEQ ID NO:17), and various C-terminally truncated forms comprising 127–134 amino acid residues. It is known that 1–15 amino acid residues may be deleted from the C-terminus without abolishing IFNG activity of the molecule. Furthermore, heterogenecity of the huIFNG C-terminus was described by Pan et al. (Eur. J. Biochem. 166:145–149, 1987).

HuIFNG muteins were reported by Slodowski et al. (Eur. J. Biochem. 202:1133–1140, 1991), Luk et al. (J. Biol. Chem. 265:13314–13319, 1990), Seelig et al., (Biochemistry 27:1981–1987, 1988), Trousdale et al. (Invest. Ophthalmol. Vis. Sci. 26:1244–1251, 1985), and in EP 146354. A natural huIFNG variant was reported by Nishi et al. (J. Biochem. 97:153–159, 1985).

U.S. Pat. No. 6,046,034 discloses thermostable recombinant huIFNG (rhuIFNG) variants having incorporated up to 4 pairs of cysteine residues to enable disulphide bridge formation and thus stabilization of the IFNG variant in homodimer form.

WO 92/08737 discloses IFNG variants comprising an added methionine in the N-terminal end of the full (residues 1–143) or partial (residues 1–132) amino acid sequence of wild-type human IFNG. EP 0 219 781 discloses partial huIFNG sequences comprising amino acid residues 3–124 (of SEQ ID NO:17). U.S. Pat. No. 4,832,959 discloses partial huIFNG sequences comprising residues 1–127, 5–146 and 5–127 of an amino acid sequence that compared to SEQ ID NO:17 has three additional N-terminal amino acid residues (Cys-Tyr-Cys). U.S. Pat. No. 5,004,689 discloses a DNA sequence encoding huIFNG without the 3 N-terminal amino acid residues (Cys-Tyr-Cys) and its expression in E. coli. EP 0 446 582 discloses E. coli produced rhuIFNG free of an N-terminal methionine. U.S. Pat. No. 6,120,762 discloses a peptide fragment of huIFNG comprising residues 95–134 thereof (relative to SEQ ID NO:18).

High level expression of rhuIFNG was reported by Wang et al. (Sci. Sin. B 24:1076–1084, 1994).

Glycosylation variation in rhuIFNG has been reported by Curling et al. (Biochem. J. 272:333–337, 1990) and Hooker et al., (J. of Interferon and Cytokine Research, 1998, 18: 287–295).

Polymer-modification of rhuIFNG was reported by Kita et al. (Drug Des. Deliv. 6:157–167, 1990), and in EP 236987 and U.S. Pat. No. 5,109,120.

WO 92/22310 discloses asialoglycoprotein conjugate derivatives of interferons, inter alia huIFNG.

IFNG fusion proteins have been described. For instance, EP 0 237 019 discloses a single chain polypeptide having region exhibiting interferon β activity and one region exhibiting IFNG activity.

EP 0 158 198 discloses a single chain polypeptide having a region exhibiting IFNG activity and a region exhibiting IL-2 activity. Several references described single chain dimeric IFNG proteins, e.g. Landar et al. (J. Mol. Biol., 2000, 299:169–179).

WO 99/02710 discloses single chain polypeptides, one example among many being IFNG.

WO 99/03887 discloses PEGylated variants of polypeptides belonging to the growth hormone superfamily, wherein a non-essential amino acid residue located in a specified region of the polypeptide has been replaced by a cysteine residue. IFNG is mentioned as one example of a member of the growth hormone super family, but modification thereof is not discussed in any detail.

IFNG has been suggested for treatment of interstitial lung diseases (also known as Interstitial Pulmonary Fibrosis (IPF) (Ziesche et al. (N. Engl. J. Med. 341:1264–1269, 1999 and Chest 110:Suppl:25S, 1996) and EP 0 795 332) for which purpose IFNG can be used in combination with prednisolone. In addition to IPF, granulomatous diseases (Bolinger et al, Clinical Pharmacy, 1992, 11:834–850), certain mycobacterial infections (N. Engl. J. Med. 330:1348–1355, 1994), kidney cancer (J. Urol. 152:841–845, 1994), osteopetrosis (N. Engl. J. Med. 332:1594–1599, 1995), scleroderma (J. Rheumatol. 23:654–658, 1996), hepatitis B (Hepatogastroenterology 45:2282–2294, 1998), hepatitis C (Int. Hepatol. Communic. 6:264–273, 1997), septic shock (Nature Medicine 3:678–681, 1997), and rheumatoid arthritis may be treated with IFNG.

As a pharmaceutical compound rhuIFNG is used with a certain success, above all, against some viral infections and tumors. rhuIFNG is usually applicable via parenteral, preferably via subcutaneous, injection. Maximum serum concentrations have been found after seven hours. The half-life in plasma is 30 minutes after iv administration. For this reason efficient treatment with rhuIFNG involves frequent injections. The main adverse effects consist of fever, chills, sweating, headache, myalgia and drowsiness. These effects are associated with injecting rhuIFNG and are observed within the first hours after injection. Rare side effects are local pain and erythema, elevation of liver enzymes, reversible granulo- and thrombopenia and cardiotoxicity.

WO 01/36001 discloses novel IFNG conjugates comprising a non-polypeptide moiety attached to an IFNG polypeptide which have been modified by introduction and/or deletion of attachment sites for such non-polypeptide moieties, e.g. PEG and glycosylation sites.

It is well known that when N-glycosylated molecules, such as IFNG, are produced in a glycosylating host not all potential N-glycosylation sites are fully utilized. This means that quite often a mixture of proteins having a varying degree of in vivo N-glycosylation is obtained, which in turn has the consequence that subsequent purification is necessary. Furthermore, it is often time-consuming and cumbersome to separate identical proteins having a varying degree of glycosylation. It has now surprisingly been found that by substitution of one or more amino acid residues located close to an in vivo N-glycosylation site (independently of whether said in vivo N-glycosylation site is naturally occurring in IFNG or whether the in vivo N-glycosylation site has been introduced, such as described in WO 01/36001) it is possible to obtain an increased fraction of fully glycosylated IFNG molecules. In particular, it has been found that changing the naturally occurring N-glycosylation site N-Y-S at positions 97, 98 and 99 of hIFNG to N-Y-T gives rise to a dramatically increased fraction of fully glycosylated IFNG molecules.

Furthermore, it is known that when IFNG is produced in mammalian cell lines a heterogenous population of IFNG polypeptides is obtained due to C-terminal truncation of the IFNG polypeptide (reviewed in Lundell et al. *Pharmac. Ther.* 64, 1–21, 1994). Clearly, this constitutes a severe problem in that valuable polypeptide material is lost and, further, it is necessary to carry out time-consuming and cumbersome purification in order to obtain a homogenous population of active IFNG polypeptides having the desired length. Most likely, this truncation is effected by endo- and/or exoprotease activity produced by the host cell.

Thus, it is also an object of the present invention to provide IFNG fragments and variants thereof, which are not prone to C-terminal truncation during production, purification or storage.

BRIEF DISCLOSURE OF THE INVENTION

Thus, in a first aspect the present invention relates to an IFNG polypeptide variant exhibiting IFNG activity and having the amino acid sequence shown in SEQ ID NO:12 ([S99T]huIFNG-132). In a highly preferred embodiment of the invention, the variant comprises at least one further modification, such as 1–10 further modifications, relative to the amino acid sequence shown in SEQ ID NO:12. An example of a particular preferred further modification is E38N+S40T.

Another aspect of the present invention relates to a nucleotide sequence encoding an IFNG polypeptide variant exhibiting IFNG activity and having the amino acid sequence shown in SEQ ID NO:12.

In a still further aspect the present invention relates to a nucleotide sequence encoding an IFNG polypeptide variant exhibiting IFNG activity, wherein said variant comprises at least one modification, such as 1–10 modifications, relative to the amino acid sequence shown in SEQ ID NO:12.

An additional aspect of the present invention relates to a nucleotide sequence encoding a polypeptide having the amino acid sequence shown in SEQ ID NO:29.

In further aspects the present invention relates to an expression vector comprising a nucleotide sequence of the invention, and to a glycosylating host cell comprising a nucleotide sequence of the invention or an expression vector of the invention.

In a still further aspect the present invention relates a population of IFNG polypeptide variants, or to a composition comprising a population of IFNG polypeptide variants, wherein said population comprises at least 70% of the IFNG polypeptide variant having the amino acid sequence shown in SEQ ID NO:12. In a highly preferred embodiment of the invention, said population comprises at least 70% of an IFNG polypeptide variant which comprises at least one further modification, such as 1–10 further modifications, relative to the amino acid sequence shown in SEQ ID NO:12. An example of a particular preferred further modification is E38N+S40T.

In a still further aspect the present invention relates to a pharmaceutical composition comprising an IFNG variant of the invention.

In a still further aspect the present invention relates to a method for producing an IFNG polypeptide variant of the invention, said method comprising (a) culturing a eukaryotic host cell, preferably a CHO cell, comprising a nucleotide sequence which encodes an IFNG polypeptide variant of the invention under conditions conducive for expression of the polypeptide variant;

(b) optionally reacting said polypeptide variant with a non-polypeptide moiety in vitro under conditions conducive for conjugation to take place; and (c) recovering the polypeptide variant.

In an even further aspect the present invention relates to a method for reducing or avoiding C-terminal heterogeneity of an IFNG polypeptide produced in a eukaryotic host cell, said method comprising culturing a eukaryotic host cell comprising a nucleotide sequence which encodes an IFNG polypeptide variant of the invention under conditions conducive for expression of the polypeptide variant.

Further aspects of the invention will be apparent from the below disclosure and the appended claims.

rhuIFNG. The [E38N+S40T+S99T] variant was administered in a dose of $1.15 \times 10^7$ AU/kg, whereas the two PEGylated variants were administered in a dose of $4.6 \times 10^6$ AU/kg.

Figure 4:
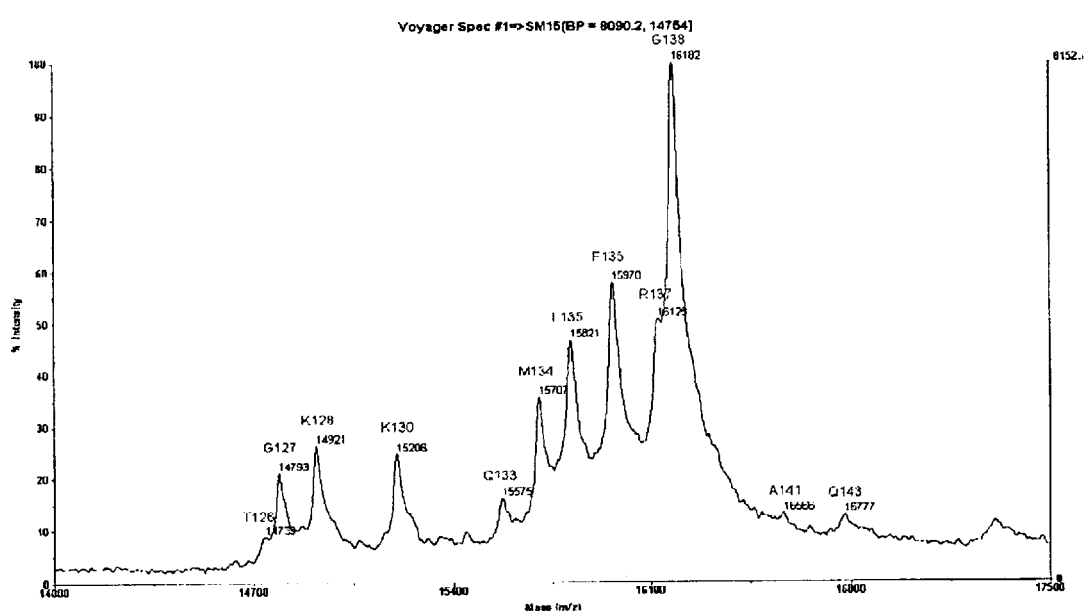

FIG. 4 shows a MALDI-TOF mass spectra of [E38N+S40T+S99T]rhuIFNG purified from culture media by diafiltration followed by cation exchange, immunoprecipitation and de-glycosylation with PNGase F. See Example 12 for further details.

Figure 5:
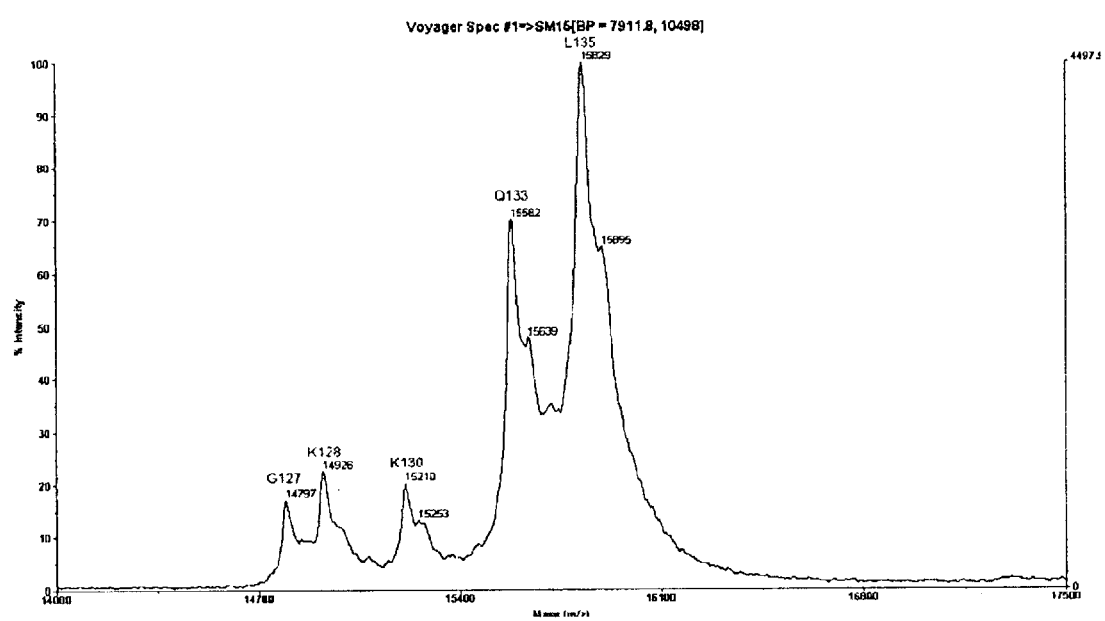

FIG. 5 shows a MALDI-TOF mass spectra of [E38N+S40T+S99T]rhuIFNG-135 purified from culture media by diafiltration followed by cation exchange, immunoprecipitation and de-glycosylation with PNGase F. See Example 12 for further details.

Figure 6:
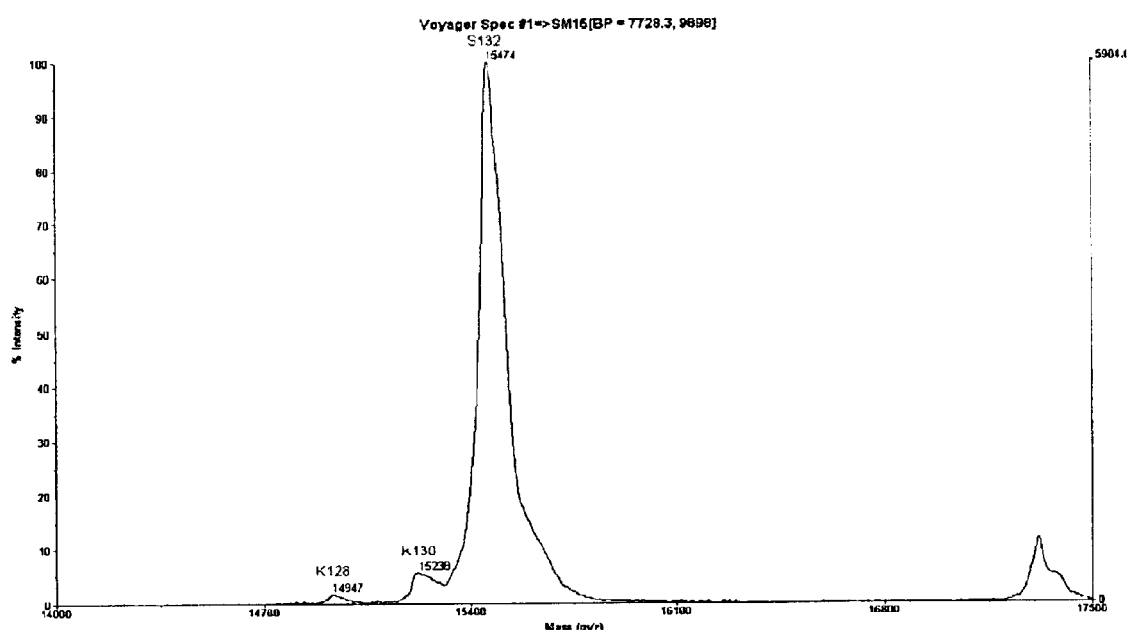

FIG. 6 shows a MALDI-TOF mass spectra of [E38N+S40T+S99T]rhuIFNG-132 purified from culture media by diafiltration followed by cation exchange, immunoprecipitation and de-glycosylation with PNGase F. See Example 12 for further details.

DETAILED DESCRIPTION OF THE INVENTION

Definitions

In the context of the present application and invention the following definitions apply:

The term "conjugate" (or interchangeably "conjugated polypeptide" or "conjugated variant") is intended to indicate a heterogeneous (in the sense of composite or chimeric) molecule formed by the covalent attachment of one or more polypeptide variant(s) to one or more non-polypeptide moieties. The term covalent attachment means that the polypeptide variant and the non-polypeptide moiety are either directly covalently joined to one another, or else are indirectly covalently joined to one another through an intervening moiety or moieties, such as a bridge, spacer, or linkage moiety or moieties. Preferably, a conjugated polypeptide variant is soluble at relevant concentrations and conditions, i.e. soluble in physiological fluids such as blood. Examples of conjugated polypeptide variants of the invention include glycosylated and/or PEGylated polypeptide variants. The term "non-conjugated polypeptide variant" may be used about the polypeptide part of the conjugated polypeptide variant.

The term "non-polypeptide moiety" is intended to indicate a molecule that is capable of conjugating to an attachment group of the IFNG polypeptide variant. Preferred examples of such molecules include polymer molecules, lipophilic compounds, sugar moieties or organic derivatizing agents. It will be understood that the non-polypeptide moiety is linked to the polypeptide through an attachment group of the polypeptide variant. Except where the number of non-polypeptide moieties, such as polymer molecule(s), attached to the IFNG polypeptide variant is expressly indicated every reference to "a non-polypeptide moiety" attached to the IFNG polypeptide variant or otherwise used in the present invention shall be a reference to one or more non-polypeptide moieties attached to the IFNG polypeptide variant.

The term "polymer molecule" is defined as a molecule formed by covalent linkage of two or more monomers, wherein none of the monomers is an amino acid residue. The term "polymer" may be used interchangeably with the term "polymer molecule".

The term "sugar moiety" is intended to indicate a carbohydrate molecule attached by in vivo or in vitro glycosylation, such as N- or O-glycosylation.

An "N-glycosylation site" has the sequence N-X-S/T/C", wherein X is any amino acid residue except proline, N is asparagine and S/T/C is either serine, threonine or cysteine, preferably serine or threonine, and most preferably threonine. An "O-glycosylation site" is the OH-group of a serine or threonine residue.

The term "attachment group" is intended to indicate an amino acid residue group capable of coupling to the relevant non-polypeptide moiety such as a polymer molecule or a sugar moiety. Useful attachment groups and their matching non-polypeptide moieties are apparent from the table below.

| Attachment group | Amino acid | Examples of non-polypeptide moiety | Conjugation method/activated PEG | Reference |
|---|---|---|---|---|
| —NH$_2$ | N-terminal, Lys | Polymer, e.g. PEG | mPEG-SPA Tresylated mPEG | Shearwater Inc. Delgado et al, critical reviews in Therapeutic Drug Carrier Systems 9(3,4): 249–304 (1992) |
| —COOH | C-term, Asp, Glu | Polymer, e.g. PEG Sugar moiety | mPEG-Hz In vitro coupling | Shearwater Inc |
| —SH | Cys | Polymer, e.g. PEG, | PEG-vinylsulphone PEG-maleimide | Shearwater Inc Delgado et al, critical reviews in Therapeutic |
| | | Sugar moiety | In vitro coupling | Drug Carrier Systems 9(3,4): 249–304 (1992) |
| —OH | Ser, Thr, OH—, Lys | Sugar moiety | In vivo O-linked glycosylation | |
| —CONH$_2$ | Asn as part of an N-glycosylation site | Sugar moiety | In vivo glycosylation | |
| Aromatic residue | Phe, Tyr, Trp | Sugar moiety | In vitro coupling | |

-continued

| Attachment group | Amino acid | Examples of non-polypeptide moiety | Conjugation method/activated PEG | Reference |
|---|---|---|---|---|
| —CONH$_2$ | Gln | Sugar moiety | In vitro coupling | Yan and Wold, Biochemistry, 1984, Jul 31; 23(16): 3759–65 |
| Aldehyde Ketone | Oxidized carbohydrate | Polymer, e.g. PEG, PEG-hydrazide | PEGylation | Andresz et al., 1978, Makromol. Chem. 179: 301; WO 92/16555, WO 00/23114 |
| Guanidino | Arg | Sugar moiety | In vitro coupling | Lundblad and Noyes, Chimical Reagents for Protein Modification, CRC Press Inc. Boca Raton, Fl |
| Imidazole ring | His | Sugar moiety | In vitro coupling | As for guanidine |

For in vivo N-glycosylation, the term "attachment group" is used in an unconventional way to indicate the amino acid residues constituting an N-glycosylation site (with the sequence N-X-S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present. Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the IFNG polypeptide is to be understood as one, two or all of the amino acid residues constituting an N-glycosylation site is/are to be altered in such a manner that either a functional N-glycosylation site is introduced into the amino acid sequence, removed from said sequence or a functional N-glycosylation site is retained in the amino acid sequence (e.g. by substituting a serine residue, which already constitutes part of an N-glycosylation site, with a threonine residue and vice versa).

In the present application, amino acid names and atom names (e.g. CA, CB, CD, CG, SG, NZ, N, O, C, etc) are used as defined by the Protein DataBank (PDB) which are based on the IUPAC nomenclature (IUPAC Nomenclature and Symbolism for Amino Acids and Peptides (residue names, atom names etc.), Eur. J. Biochem., 138, 9–37 (1984) together with their corrections in Eur. J. Biochem., 152, 1 (1985). CA is sometimes referred to as Cα, CB as Cβ. The term “amino acid residue” is intended to indicate an amino acid residue contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gin or Q), arginine (Arg or R), serine (Ser or S), threonine (Thr or T), valine (Val or V), tryptophan (Trp or W), and tyrosine (Tyr or Y) residues.

Numbering of amino acid residues in this document is from the N-terminus of [S99T]huIFNG without signal peptide (i.e. SEQ ID NO:1) or, where relevant, from the N-terminus of huIFNG without signal peptide (i.e. SEQ ID NO:17).

The terminology used for identifying amino acid positions/substitutions is illustrated as follows: G18 indicates position 18 occupied by glycine in the amino acid sequence shown in SEQ ID NO:1 or SEQ ID NO:17. G18N indicates that the Gly residue of position 18 has been replaced with an Asn. Multiple substitutions are indicated with a “+”, e.g. G18N+S20T means an amino acid sequence which comprises a substitution of the Gly residue in position 18 with an Asn and a substitution of the Ser residue in position 20 with Thr. Alternative substitutions are indicated with a “/”. For example, G18S/T covers the following individual substitutions: G18S and G18T. Deletions are indicated by an asterix. For example, G18* indicates that the Gly residue in position 18 has been deleted. Insertions are indicated the following way: Insertion of an additional Ser residue after the Gly residue located at position 18 is indicated as G18GS. Combined substitutions and insertions are indicated in the following way: Substitution of the Gly residue at position 18 with an Ser residue and insertion of an Ala residue after the position 18 amino acid residue is indicated as G18SA.

The term “nucleotide sequence” is intended to indicate a consecutive stretch of two or more nucleotide molecules. The nucleotide sequence may be of genomic, cDNA, RNA, semisynthetic, synthetic origin, or any combinations thereof.

The term “polymerase chain reaction” or “PCR” generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

“Cell”, “host cell”, “cell line” and “cell culture” are used interchangeably herein and all such terms should be understood to include progeny resulting from growth or culturing of a cell.

“Transformation” and “transfection” are used interchangeably to refer to the process of introducing DNA into a cell.

“Operably linked” refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

The term "modification", as used herein, covers substitution, insertion and deletion.

The terms "mutation" and "substitution" are used interchangeably herein.

The term "introduce" is primarily intended to mean substitution of an existing amino acid residue, but may also mean insertion of an additional amino acid residue.

The term "remove" is primarily intended to mean substitution of the amino acid residue to be removed for another amino acid residue, but may also mean deletion (without substitution) of the amino acid residue to be removed.

The term "amino acid residue comprising an attachment group for the non-polypeptide moiety" is intended to indicate that the amino acid residue is one to which the non-polypeptide moiety binds (in the case of an introduced amino acid residue) or would have bound (in the case of a removed amino acid residue).

The term "one difference" or "differs from" as used in connection with specific modifications is intended to allow for additional differences being present apart from the specified amino acid difference. Thus, in addition to amino acid residue alterations disclosed herein aiming at optimising the utilization of glycosylation sites or removing and/or introducing amino acid residues comprising an attachment group for a non-polypeptide moiety, the IFNG polypeptide variant may, if desired, comprise other modifications that are not related to such alterations. These may, for example, include truncation of the C-terminus by one or more amino acid residues, addition of one or more extra residues at the N- and/or C-terminus, e.g. addition of a Met residue at the N-terminus, addition of the amino acid sequence Cys-Tyr-Cys at the N-terminus, as well as "conservative amino acid substitutions", i.e. substitutions performed within groups of amino acids with similar characteristics, e.g. small amino acids, acidic amino acids, polar amino acids, basic amino acids, hydrophobic amino acids and aromatic amino acids. Examples of conservative substitutions in the present invention may in particular be selected from the groups listed in the table below.

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Histidine (H) | Lysine (K) | |
| 5 | Isoleucine (I) | Leucine (L) | Methionine (M) | Valine (V) |
| 6 | Phenylalanine (F) | Tyrosine (Y) | Tryptophan (W) | |

The term "at least one" as used about a non-polypeptide moiety, an amino acid residue, a substitution, etc., is intended to mean one or more.

The term "$AUC_{sc}$" or "Area Under the Curve when administered subcutaneously" is used in its normal meaning, i.e. as the area under the IFNG activity in serum-time curve, where the IFNG polypeptide variant has been administered subcutaneously, in particular when administered subcutaneously in rats. Once the experimental IFNG activity-time points have been determined, the $AUC_{sc}$ may conveniently be calculated by a computer program, such as GraphPad Prism 3.01.

The term "functional in vivo half-life" is used in its normal meaning, i.e. the time at which 50% of the biological activity of the polypeptide is still present in the body/target organ, or the time at which the activity of the polypeptide is 50% of the initial value.

As an alternative to determining functional in vivo half-life, "serum half-life" may be determined, i.e. the time at which 50% of the polypeptide circulates in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life". The serum half-life may conveniently by determined in rats, cf. the Materials and Method section herein. It is important to note that the term "serum half-life", when used herein, for a given IFNG polypeptide variant must be determined for a sample that has been administered intravenously (iv).

The term "serum" is used in its normal meaning, i.e. as blood plasma without fibrinogen and other clotting factors.

The term "huIFNG" is intended to mean the mature form of wild-type human IFNG having the amino sequence shown in SEQ ID NO:17.

The term "rhuIFNG" is intended to cover the mature form of wild-type human IFNG having the amino acid sequence shown in SEQ ID NO:17, which has been produced by recombinant means.

The term "[S99T]huIFNG" is used to indicate the mature form of wild-type human IFNG, wherein the serine residue in position 99 has been replaced with a threonine residue (disclosed in SEQ ID NO:1).

The term "huIFNG-132" refers to the mature form of wild-type human IFNG, which lacks 11 amino acid residues at the C-terminal, i.e. this fragment contains 132 amino acid residues (disclosed in SEQ ID NO:29).

The term "[S99T]huIFNG-132" refers to the mature form of wild-type human IFNG, which lacks 11 amino acid residues at the C-terminal and wherein the serine residue in position 99 has been replaced with a threonine residue, i.e. this fragment contains 132 amino acid residues (disclosed in SEQ ID NO:12).

The term "huIFNG-135" refers to the mature form of wild-type human IFNG, which lacks 8 amino acid residues at the C-terminal, i.e. this fragment contains 135 amino acid residues (disclosed in SEQ ID NO:26).

The term "[S99T]huIFNG-135" refers to the mature form of wild-type human IFNG, which lacks 8 amino acid residues at the C-terminal and wherein the serine residue in position 99 has been replaced with a threonine residue, i.e. this fragment contains 135 amino acid residues (disclosed in SEQ ID NO:9).

When used herein the terms "glycosylated" or "in glycosylated form" indicate that the IFNG polypeptide are produced in a cell capable of glycosylating the polypeptide and, therefore, the IFNG polypeptide is glycosylated at its native N-glycosylation sites at position 25 and 97, respectively. Furthermore, if the terms "glycosylated" or "in glycosylated form" are used about a variant comprising an introduced N-glycosylation site (such as E38N+S40T), these terms indicate that the variant is not only glycosylated at its native N-glycosylation sites at position 25 and 97, but also glycosylated at the introduced N-glycosylation site (such as also glycosylated in position 38).

When used herein the term "ACTIMMUNE® IFNG" refers to the 140 amino acid form (ACTIMMUNE® is C-terminally truncated with 4 amino acid residues and includes one N-terminal Met residue) of IFNG (disclosed in SEQ ID NO:34) achieved by fermentation of a genetically engineered *E. coli* bacterium. Further information of ACTIMMUNE® IFNG is available from InterMune Inc.

The polypeptide is normally cleared by the action of one or more of the reticuloendothelial systems (RES), kidney, spleen or liver, or by specific or unspecific proteolysis. The term "renal clearance" is used in its normal meaning to indicate any clearance taking place by the kidneys, e.g. by glomerular filtration, tubular excretion or tubular elimination. Normally, renal clearance depends on physical characteristics of the polypeptide, including molecular weight, size (relative to the cutoff for glomerular filtration), symmetry, shape/rigidity, charge, attached carbohydrate chains and the presence of cellular receptors for the polypeptide. A molecular weight of about 67 kDa is normally considered to be a cut-off-value for renal clearance. Renal clearance may be measured by any suitable assay, e.g. an established in vivo assay. For instance, renal clearance may be determined by administering a labelled (e.g. radiolabelled or fluorescence labelled) conjugated polypeptide to a patient and measuring the label activity in urine collected from the patient. Reduced renal clearance is determined relative to the reference molecule, such as huIFNG, [S99T]huIFNG or ACTIMMUNE® IFNG. The functionality to be retained is normally selected from antiviral, antiproliferative, immunomodulatory or IFNG receptor binding activity.

The term "increased" as used about the functional in vivo half-life or serum half-life is used to indicate that the relevant half-life of the IFNG variant is statistically significantly increased relative to that of a reference molecule, such as glycosylated huIFNG (SEQ ID NO: 17), glycosylated [S99T]huIFNG (SEQ ID NO: 1) or ACTIMMUNE® IFNG (SEQ ID NO:34—produced in *E. coli*), when administered intravenously and when determined under comparable conditions. Thus, interesting IFNG polypeptide variants are such variants, which have an increased functional in vivo half-life or an increased serum half-life as compared to any of the reference molecules mentioned above.

The term "increased" as used about the $AUC_{sc}$ is used to indicate that the Area Under the Curve for an IFNG variant of the invention, when administered subcutaneously, is statistically significantly increased relative to that of a reference molecule, such as glycosylated huIFNG (SEQ ID NO: 17), glycosylated [S99T]huIFNG (SEQ ID NO: 1) or ACTIMMUNE® IFNG (SEQ ID NO:34—produced in *E. coli*), determined under comparable conditions. Thus, preferred IFNG variants are such variants, which have an increased $AUC_{sc}$, as compared to any of the reference molecules mentioned above. Evidently, the same amount of IFNG activity should be administered for the IFNG variant of the invention and the reference molecule. Consequently, in order to make direct comparisons between different IFNG molecules, the $AUC_{sc}$ values may be normalized, i.e. they may be expressed as $AUC_{sc}$ dose administered.

The term "$T_{max,sc}$" is used about the time in the IFNG activity in serum-time curve when the highest IFNG activity in serum is observed: Preferred IFNG variants of the invention are such variants which have an increased $T_{max,as}$ compared to huIFNG, [S99T]huIFNG, huIFNG-132 or [S99T]huIFNG-132, in their glycosylated forms, or ACTIMMUNE® IFNG.

The term "reduced immunogenicity" is intended to indicate that the IFNG polypeptide variant gives rise to a measurably lower immune response than a reference molecule, e.g. huIFNG, [S99T]huIFNG, huIFNG-132 or [S99T]huIFNG-132, in their glycosylated forms, or ACTIMMUNE® IFNG, as determined under comparable conditions. The immune response may be a cell or antibody mediated response (see, e.g., Roitt: Essential Immunology (8th Edition, Blackwell) for further definition of immunogenicity). Normally, reduced antibody reactivity is an indication of reduced immunogenicity. Reduced immunogenicity may be determined by use of any suitable method known in the art, e.g. in vivo or in vitro.

In the present context the terms "increased glycosylation", "increased degree of in vivo N-glycosylation" or "increased degree of N-glycosylation" are intended to indicate increased levels of attached carbohydrate molecules, normally obtained as a consequence of increased (or better) utilization of glycosylation site(s). It is well-known (Hooker et al., 1998, J. Interferon and Cytokine Res. 18, 287–295 and Sarenva et al., 1995, Biochem J., 308, 9–14) that when huIFNG is expressed in CHO cells only about 50% of the IFNG molecules utilizes both glycosylation sites, about 40% utilizes one glycosylation site (1N), and about 10% is not glycosylated (0N). The increased degree of in vivo N-glycosylation may be determined by any suitable method known in the art, e.g. by SDS-PAGE. One convenient assay for determining increased glycosylation is the method described in the section entitled "Determination of Increased Glycosylation" in the Materials and Methods section herein.

The term "exhibiting IFNG activity" is intended to indicate that the polypeptide variant has one or more of the functions of native huIFNG or rhuIFNG, including the capability to bind to an IFNG receptor and cause transduction of the signal transduced upon huIFNG-binding of its receptor as determined in vitro or in vivo (i.e. in vitro or in vivo bioactivity). The IFNG receptor has been described by Aguet et al. (Cell 55:273–280, 1988) and Calderon et al. (Proc. Natl. Acad. Sci. USA 85:4837–4841, 1988). A suitable assay for testing IFNG activity is the assay entitled "Primary Assay" disclosed herein. When using the "Primary Assay" described herein, polypeptide variants "exhibiting IFNG activity" have a specific activity of at least 5% as compared to huIFNG or huIFNG-132. It will be understood, that depending on which specific modifications are performed, for example whether the variant is PEGylated or not, may lead to activities over a wide range. Thus, examples of specific activities may range from as low as 5% to as high as 150% as compared to huIFNG or huIFNG-132. For example, the specific activity may be at least 10% (e.g. 10–125%), such as at least 15% (e.g. 15–125%), e.g. at least 20% (such as 20–125%), at least 25% (e.g. 25–125%), at least 30% (e.g. 30–125%), at least 35% (e.g. 35–125%), at least 40% (e.g. 40–125%), at least 45% (e.g. 45–125%), at least 50% (e.g. 50–125%), at least 55% (e.g. 55–125%), at least 60% (e.g. 60–125%), at least 65% (e.g. 65–125%), at least 70% (e.g. 70–125%), at least 75% (e.g. 75–125%), at least 80% (e.g. 80–125%) or at least 90% (e.g. 90–110%) as compared to the specific activity of huIFNG or huIFNG-132.

An "IFNG polypeptide" is a polypeptide exhibiting IFNG activity, i.e. the term "IFNG polypeptide" is used about any IFNG molecule (independently of whether this molecule is huIFNG, a truncated form thereof, or a variant thereof) as long as said IFNG molecule exhibits IFNG activity as defined herein. The term "IFNG polypeptide" is used herein about the polypeptide in monomer or dimeric form, as appropriate. For instance, when specific substitutions are indicated these are normally indicated relative to the huIFNG polypeptide monomer. When reference is made to the IFNG molecule of the invention this is normally in dimeric form (and thus, e.g., comprises two IFNG polypeptide monomers modified as described). The dimeric form of the IFNG polypeptides may be provided by the normal association of two monomers or be in the form of a single chain dimeric IFNG polypeptide.

The term "parent" is intended to indicate the IFNG polypeptide to have the glycosylation site(s) improved in accordance with the present invention. Although the parent polypeptide to be modified by the present invention may be any polypeptide with IFNG activity, and thus be derived from any origin, e.g. a non-human mammalian origin, it is preferred that the parent polypeptide is huIFNG with the amino acid sequence shown in SEQ ID NO:17 or a fragment thereof, in particular SEQ ID NO:29.

A "fragment" is a part of the full-length IFNG polypeptide sequence (e.g. a fragment of the full-length huIFNG polypeptide shown in SEQ ID NO:17, such as SEQ ID NO:29, or a fragment of the full-length [S99T]huIFNG polypeptide variant shown in SEQ ID NO:1, such as SEQ ID NO:12) exhibiting IFNG activity, e.g. a C-terminally or N-terminally truncated version thereof. Specific examples of IFNG polypeptide variant fragments include [S99T]huIFNG C-terminally truncated with 1–15 amino acid residues, e.g. with 1 amino acid residue (SEQ ID NO:2), 2 amino acid residues (SEQ ID NO:3), 3 amino acid residues (SEQ ID NO:4), 4 amino acid residues (SEQ ID NO:5), 5 amino acid residues (SEQ ID NO:6), 6 amino acid residues (SEQ ID NO:7), 7 amino acid residues (SEQ ID NO:8), 8 amino acid residues (SEQ ID NO:9), 9 amino acid residues (SEQ ID NO:10), 10 amino acid residues (SEQ ID NO:11), 11 amino acid residues (SEQ ID NO:12), 12 amino acid residues (SEQ ID NO:13), 13 amino acid residues (SEQ ID NO:14), 14 amino acid residues (SEQ ID NO:15) or 15 amino acid residues (SEQ ID NO:16) and/or N-terminally truncated with 1–3 amino acid residues. A particular preferred fragment of [S99T]huIFNG is the fragment which is C-terminally truncated with 11 amino acid residues (shown in SEQ ID NO:12).

Specific examples of huIFNG fragments include huIFNG, which is C-terminally truncated with 1–15 amino acid residues, e.g. with 1 amino acid residue (SEQ ID NO:19), 2 amino acid residues (SEQ ID NO:10), 3 amino acid residues (SEQ ID NO:21), 4 amino acid residues (SEQ ID NO:22), 5 amino acid residues (SEQ ID NO:23), 6 amino acid residues (SEQ ID NO:24), 7 amino acid residues (SEQ ID NO:25), 8 amino acid residues (SEQ ID NO:26), 9 amino acid residues (SEQ ID NO:27), 10 amino acid residues (SEQ ID NO:28), 11 amino acid residues (SEQ ID NO:29), 12 amino acid residues (SEQ ID NO:30), 13 amino acid residues (SEQ ID NO:31), 14 amino acid residues (SEQ ID NO:32) or 15 amino acid residues (SEQ ID NO:33) and/or N-terminally truncated with 1–3 amino acid residues. A particular preferred fragment of huIFNG is the fragment which is C-terminally truncated with 11 amino acid residues (shown in SEQ ID NO:29).

As indicated above, the IFNG polypeptide variant may comprise at least one further modification in addition to the S99T substitution as long as said variant exhibits IFNG activity, i.e. the variant may be a variant of [S99T]huIFNG, or a variant of a fragment of [S99T]huIFNG, such as a variant of SEQ ID NO:12. Specific examples of such variants are variants having introduced and/or removed amino acid residues comprising an attachment group for a non-polypeptide moiety. Other examples of variants of [S99T] huIFNG (and fragments thereof, such as SEQ ID NO:12) are the variants described in the "Background of the invention" section above and include, e.g. [S99T]huIFNG with the N-terminal addition Cys-Tyr-Cys or with Met, and the cysteine-modified variants disclosed in U.S. Pat. No. 6,046,034.

Normally, the variant according to the invention is encoded by a nucleotide sequence, which, compared to the nucleotide sequence encoding the parent IFNG polypeptide, has been modified in accordance with the present invention. This may, however, not always be the case, since the variant polypeptide may be subjected to C- or N-terminal truncation during posttranslational processing, e.g. by C- or N-terminal cleavage by proteases in the cell, in the expression media, during purification, etc., so that the resulting variant polypeptide is a truncated version of the originally produced variant polypeptide (for example, although a full-length variant is initially produced, a C-terminally truncated variant polypeptide may be obtained due to posttranslational processing of the full-length variant polypeptide). In this case, the term "parent" should be construed as the truncated form to be modified in accordance with the invention.

The term "variant" is intended to cover a polypeptide, which differs in one or more amino acid residues from its parent polypeptide (normally SEQ ID NO:17 or any of the truncated forms thereof shown in SEQ ID NOS:19–33, in particular SEQ ID NO:29), typically in 1–15 amino acid residues (such as in 1, 2, 3, 4, 5, 6, 7, 8, 9, 10, 11, 12, 13, 14 or 15 amino acid residues), e.g. in 1–10 amino acid residues, in 1–5 amino acid residues or in 1–3 amino acid residues.

The term "functional site" is intended to indicate one or more amino acid residues which is/are essential for, or otherwise involved in, the function or performance of IFNG. Such amino acid residues are "located at" the functional site. The functional site may be determined by methods known in the art and is preferably identified by analysis of a structure of the polypeptide complexed to a relevant receptor, such as the IFNG receptor.

Interferon Gamma Polypeptide Variants of the Present Invention

IFNG Variants of the Invention with Optimised in vivo Glycosylation Sites

As indicated previously, it has surprisingly been found that glycosylation of the naturally occurring N-glycosylation site located in position 97 of huIFNG may be increased, i.e. an increased fraction of fully, or substantially fully, glycosylated IFNG molecules may be obtained, by substituting the serine residue located in position 99 of huIFNG (or fragments thereof, such as SEQ ID NO:29) with a threonine residue. Inspection of FIG. 1 reveals that a significant increase in the degree of fully glycosylated IFNG polypeptide can be achieved. For the [S99T]huIFNG (SEQ ID NO:1) polypeptide variant it can be seen that about 90% of the polypeptide variants present in the harvested medium utilized both N-glycosylation sites, whereas only about 60% of the rhuIFNG polypeptides present in the harvested medium were fully glycosylated.

Accordingly, in a first aspect the present invention relates to an IFNG polypeptide variant exhibiting IFNG activity and having the amino acid sequence shown in SEQ ID NO:1 (i.e. [S99T]huIFNG), or fragment thereof, such as SEQ ID NO:12, exhibiting IFNG activity.

As already discussed above, it is known that C-terminally truncated forms of huIFNG retain activity, and in some cases even have increased activity, compared to huIFNG. Thus, in an interesting embodiment of the invention the IFNG polypeptide variant of the invention is a fragment of SEQ ID NO:1, which is C-terminally truncated with 1–15 amino acid residues. Specific examples of such C-terminally truncated forms of SEQ ID NO:1 are disclosed in SEQ ID NOS:2–16. The IFNG polypeptide fragment according to this embodiment of the present invention exhibits IFNG activity. A particular preferred C-terminally truncated form of SEQ ID NO:1 is the fragment shown in SEQ ID NO:12.

It will be understood that the glycosylated IFNG polypeptide variants according to this aspect should be expressed recombinantly in a glycosylating host cell, preferably a mammalian host cell, such as any of those mentioned in the section entitled "Coupling to a sugar moiety".

As explained above, only about 50–60% of the total population of expressed IFNG polypeptides are fully glycosylated when rhuIFNG is expressed in CHO cells. Thus, one of the main advantages of the IFNG polypeptide variants of the present invention is the higher utilization of the position 97 in vivo N-glycosylation site, which in turn has the consequence that a more homogenous population is obtained compared to huIFNG. Due to the more homogenous population, compositions (e.g. the harvested medium) comprising such a population of IFNG polypeptide variants do not require the same cumbersome and time-consuming purification as rhuIFNG.

Thus, in a further aspect the present invention relates to a population of IFNG polypeptide variants, or to a composition comprising a population of IFNG polypeptide variants, wherein said population comprises at least about 70% of a glycosylated IFNG polypeptide variant of the invention. Preferably, the composition comprises at least 75%, more preferably at least 80%, even more preferably at least 85%, such as about 90% of a glycosylated IFNG polypeptide variant of the invention.

More particularly, the invention relates to a population of IFNG polypeptide variants, or to a composition comprising a population of IFNG polypeptide variants, wherein said population comprises at least 70%, preferably at least 75%, more preferably at least 80%, even more preferably at least 85%, such as about 90% of the glycosylated IFNG polypeptide variant having the amino acid sequence shown in SEQ ID NO:1.

Analogously, the invention also relates to a population of IFNG polypeptide variants, or to a composition comprising a population of IFNG polypeptide variants, wherein said population comprises at least 70%, preferably at least 75%, more preferably at least 80%, even more preferably at least 85%, such as about 90% of a glycosylated IFNG polypeptide variant fragment having an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16, preferably SEQ ID NO:12.

In addition to the already mentioned S99T mutation required for optimisation of the in vivo N-glycosylation site at position 97 in rhuIFNG, other in vivo glycosylation sites, which have been introduced into SEQ ID NO:1 or fragments thereof, such as SEQ ID NO:12 (e.g. in order to increase the serum half-life and/or to increase the $AUC_{sc}$) may be optimised. Normally, the in vivo glycosylation site is an N-glycosylation site, but also an O-glycosylation site is contemplated as relevant for the present invention. This optimisation may be achieved by performing a modification, preferably a substitution, in a position which is located close to a glycosylation site, in particular close to an in vivo N-glycosylation. Typically, such an in vivo N-glycoyslation site is an introduced in vivo N-glycosylation site. Specific examples of suitable positions to introduce in vivo N-glycosylation sites are disclosed in WO 01/36001 and further below.

An amino acid residue "located close to" a glycosylation site is usually located in position −4, −3, −2, −1, +1, +2, +3 or +4 relative to the amino acid residue of the glycosylation site to which the carbohydrate is attached, preferably in position −1, +1, or +3, in particular in position +1 or +3. Thus, the amino acid residue located close to an in vivo N-glycosylation site (having the sequence N-X-S/T/C) may be located in position −4, −3, −2, −1, +1, +2, +3 or +4 relative to the N-residue.

When position +2 relative to the N-residue is modified it will be understood that only a limited number of modifications are possible since in order to maintain/introduce an in vivo N-glycosylation site, the amino acid residue in said position must be either Ser, Thr or Cys.

In a particular preferred embodiment of the invention, the modification of the amino acid residue in position +2 relative to the in vivo N-glycosylation site is a substitution where the amino acid residue in question is replaced with a Thr residue. If, on the other hand, said amino acid residue is already a Thr residue it is normally not preferred or necessary to perform any substitutions in that position. When X is modified, X should not be Pro and preferably not Trp, Asp, Glu and Leu. Further, the amino acid residue to be introduced is preferably selected form the group consisting of Phe, Asn, Gln, Tyr, Val, Ala, Met, Ile, Lys, Gly, Arg, Thr, His, Cys and Ser, more preferably Ala, Met, Ile, Lys, Gly, Arg, Thr, His, Cys and Ser, in particular Ala or Ser.

When position +3 relative to the N-residue is modified, the amino acid residue to be introduced is preferably selected from the group consisting of His, Asp, Ala, Met, Asn, Thr, Arg, Ser and Cys, more preferably Thr, Arg, Ser and Cys. Such modifications are particularly relevant if the X residue is a Ser residue.

Thus, with respect to the naturally present in vivo N-glycosylation, it is contemplated that the N-glycosylation site at position 97 may be further optimised by performing a modification, such as a substitution, in a position selected from the group consisting of E93, K94, L95, T96, Y98, V100 and T101 (i.e. at position −4, −3, −2, −1, +1, +3 or +4 relative to N97). Specific examples of substitutions performed in position 98 of SEQ ID NO:1 (or fragments thereof, such as SEQ ID NO:12) include Y98F, Y98N, Y98Q, Y98V, Y98A, Y98M, Y98I, Y98K, Y98G, Y98R, Y98T, Y98H, Y98C and Y98S, preferably Y98A, Y98M, Y98I, Y98K, Y98G, Y98R, Y98T, Y98H, Y98C and Y98S, in particular Y98S. Specific examples of substitutions performed in position 100 of SEQ ID NO:1 (or fragments thereof, such as SEQ ID NO:12) include V100H, V100D, V100A, V100M, V100N, V100T, V100R, V100S, or V100C, in particular V100T, V100R, V100S or V100C.

In a similar way, with respect to the in vivo N-glycosylation site at position 25 it is contemplated that this site may be further optimised by performing a modification, such as a substitution, in a position selected from the group consisting of D21, V22, A23, D24, G26, L28 and F29 (i.e. at position −4, −3, −2, −1, +1, +3 or +4 relative to N25). Specific examples of substitutions performed in position 26 of SEQ ID NO:1 (or fragments thereof, such as SEQ ID NO:12) include G26F, G26N, G26Y, G26Q, G26V, G26A, G26M, G26I, G26K, G26R, G26T, G26H, G26C and G26S, preferably G26A, G26M, G26I, G26K, G26R, G26T, G26H, G26C and G26S, more preferably G26A and G26S, in particular G26A. Specific examples of substitutions performed in position 28 of SEQ ID NO:1 (or fragments thereof, such as SEQ ID NO:12) include G28H, G28D, G28A, G28M, G28N, G28T, G28R, G28S, or G28S, in particular G28A, G28T, G28R, G28S or G28C.

Obviously, any of the modifications mentioned in connection with optimisation of glycosylation at position 97 may be combined with any of the above-mentioned modifications performed in connection with optimisation of glycosylation at position 25.

IFNG Variants of the Invention with Increased $AUC_{sc}$ and/or Increased Serum Half-Life In a further aspect the present invention relates to a variant of the IFNG polypeptide having the amino acid sequence shown in SEQ ID NO:1, wherein said variant exhibits IFNG activity.

Moreover, the present invention also relates to a variant of an IFNG polypeptide fragment having an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16, wherein said variant exhibits IFNG activity. In a preferred embodiment, the fragment is a variant of SEQ ID NO:12.

Thus, such a variant comprises at least one further modification compared to SEQ ID NOS:1–16, such as at least one further modification compared to SEQ ID NO:12.

In order to avoid too much disruption of the structure and function of the [S99T]huIFNG polypeptide variant (or fragments thereof, such as SEQ ID NO:12) the total number of amino acid residues to be modified in accordance with the present invention typically does not exceed 15. Usually, the IFNG polypeptide variant comprises 1–10 modifications relative to the amino acid sequence shown in SEQ ID NO:1, such as 1–8, 2–8, 1–5, 1–3 or 2–5 modifications relative to the amino acid sequence shown in SEQ ID NO:1. Preferably, the modification(s) is/are a substitution(s). It will be understood that similar considerations hold true for variants of fragments of the IFNG polypeptide variant having the amino acid sequence shown in SEQ ID NO:1 (such as variants of SEQ ID NO:12). Thus, when the variant is a variant of any of the sequences disclosed in SEQ ID NOS:2–16, such a variant usually comprises less than 15 modifications, typically 1–10 modifications, relative to the relevant amino acid sequence shown in SEQ ID NOS:2–16, such as 1–8, 2–8, 1–5, 1–3 or 2–5 modifications relative to the relevant the amino acid sequence shown in SEQ ID NOS:2–16. Preferably, the modification(s) is/are a substitution(s).

Thus, normally such an IFNG polypeptide variant (i.e. a variant which comprises at least one further modification in addition to the S99T substitution) comprises an amino acid sequence which differs from the amino acid sequence shown in SEQ ID NO:1 (or fragments thereof, such as SEQ ID NO:12) in 1, 2, 3, 4, 5, 6, 7, 8, 9, 10, 11, 12, 13, 14 or 15 amino acid residues.

In a preferred embodiment of the invention, the IFNG variant (further) comprises at least one introduced and/or at least one removed amino acid residue comprising an attachment group for a non-polypeptide moiety.

By removing or introducing an amino acid residue comprising an attachment group for the non-polypeptide moiety it is possible to specifically adapt the polypeptide so as to make the molecule more susceptible to conjugation to the non-polypeptide moiety of choice, to optimse the conjugation pattern (e.g. to ensure an optimal distribution of non-polypeptide moieties on the surface of the IFNG polypeptide variant) and thereby obtain a new conjugate molecule, which exhibits IFNG activity and in addition one or more improved properties as compared to huIFNG- or rhuIFNG-based molecules available today. For instance, by introduction of attachment groups, the IFNG polypeptide variant is boosted or otherwise altered in the content of the specific amino acid residues to which the relevant non-polypeptide moiety binds, whereby a more efficient, specific and/or extensive conjugation is achieved. By removal of one or more attachment groups it is possible to avoid conjugation to the non-polypeptide moiety in parts of the polypeptide in which such conjugation is disadvantageous, e.g. to an amino acid residue located at or near a functional site of the polypeptide (since conjugation at such a site may result in inactivation or reduced IFNG activity of the resulting conjugated polypeptide due to impaired receptor recognition). Further, it may be advantageous to remove an attachment group located closely to another attachment group in order to avoid heterogeneous conjugation to such groups. In interesting embodiments more than one amino acid residue of the IFNG polypeptide is altered, e.g. the alteration embraces removal as well as introduction of amino acid residues comprising attachment sites for the non-polypeptide moiety of choice. This embodiment is considered of particular interest in that it is possible to specifically design the IFNG polypeptide variant so as to obtain an optimal conjugation to the non-polypeptide moiety.

In addition to the removal and/or introduction of amino acid residues the polypeptide variant may comprise other modifications, e.g. substitutions, that are not related to introduction and/or removal of amino acid residues comprising an attachment group for the non-polypeptide moiety. Examples of such modifications include conservative amino acid substitutions and/or introduction of Cys-Tyr-Cys or Met at the N-terminus.

The exact number of attachment groups available for conjugation and present in the IFNG polypeptide variant in dimeric form is dependent on the effect desired to be achieved by the conjugation. The effect to be obtained is, e.g. dependent on the nature and degree of conjugation (e.g. the identity of the non-polypeptide moiety, the number of non-polypeptide moieties desirable or possible to conjugate to the polypeptide, where they should be conjugated or where conjugation should be avoided, etc.).

It will be understood that the amino acid residue comprising an attachment group for a non-polypeptide moiety, either it be removed or introduced, is selected on the basis of the nature of the non-polypeptide moiety part of choice and, in most instances, on the basis of the conjugation method to be used. For instance, when the non-polypeptide moiety is a polymer molecule such as a polyethylene glycol- or polyalkylene oxide-derived molecule amino acid residues capable of functioning as an attachment group may be selected from the group consisting of cysteine, lysine, aspartic acid, glutamic acid and arginine. In particular, cysteine is preferred. When the non-polypeptide moiety is a sugar moiety the attachment group is, e.g. an in vivo glycosylation site, preferably an N-glycosylation site.

Whenever an attachment group for a non-polypeptide moiety is to be introduced into or removed from the IFNG polypeptide having the amino acid sequence shown as SEQ ID NO:1 (or fragments thereof, such as SEQ ID NO:12), the position of the polypeptide to be modified is conveniently selected as follows:

The position is preferably located at the surface of the IFNG polypeptide, and more preferably occupied by an amino acid residue that has more than 25% of its side chain exposed to the solvent, preferably more than 50% of its side chain exposed to the solvent, as determined on the basis of a 3D structure or model of IFNG in its dimeric form, the structure or model optionally further comprising one or two IFNG receptor molecules. Such positions are listed in Example 1 herein.

Also of interest is to modify any of the 23 C-terminal amino acid residues of the parent IFNG polypeptide (in particular by introduction of amino acid residues comprising an attachment group for the non-polypeptide moiety, such as Cys residues) since such residues are believed to be located at the surface of the IFNG polypeptide.

In addition, it may be of interest to modify one or more amino acid residues located in the loop regions of the IFNG polypeptide since most amino acid residues within these loop regions are exposed to the surface and located sufficiently far away from functional sites so that non-polypeptide moieties, such as polymer molecules, in particular PEG molecules, and/or N-glycosylation sites, may be introduced without impairing the function of the molecule. Such loops regions may be identified by inspection of the three-dimensional structure of huIFNG. The amino acid residues constituting said loop regions are residues N16-K37 (the "A–B loop"), F60-S65 (the "B–C loop"), N83-S84 (the "C–D loop") and Y98-L103 (the "D–E loop").

The amino acid residues constituting the IFNG receptor binding site are Q1, D2, Y4, V5, E9, K12, G18, H19, S20, D21, V22, A23, D24, N25, G26, T27, L30, K34, K37, K108, H111, E112, I114, Q115, A118, E119 (see also Example 2 herein). In general, it is preferred that attachment groups for a non-polypeptide moiety (such as additional N-glycosylation sites and/or cysteine residues) are not introduced into this site of the molecule.

In order to determine an optimal distribution of attachment groups, the distance between amino acid residues located at the surface of the IFNG polypeptide is calculated on the basis of a 3D structure of the IFNG dimeric polypeptide. More specifically, the distance between the CB's of the amino acid residues comprising such attachment groups, or the distance between the functional group (NZ for lysine, CG for aspartic acid, CD for glutamic acid, SG for cysteine) of one and the CB of another amino acid residue comprising an attachment group are determined. In case of glycine, CA is used instead of CB. In the IFNG polypeptide part of the invention any of said distances is preferably more than 8 Å, in particular more than 10 Å in order to avoid or reduce heterogeneous conjugation.

Also, the amino acid sequence of the IFNG polypeptide variant may differ from that of SEQ ID NO:1 (or fragments thereof, such as SEQ ID NO:12) in that one or more amino acid residues constituting part of an epitope has been removed, preferably by substitution to an amino acid residue comprising an attachment group for the non-polypeptide moiety, so as to destroy or inactivate the epitope. Epitopes of [S99T]huIFNG, huIFNG or rhuIFNG may be identified by use of methods known in the art, also known as epitope mapping, see, e.g. Romagnoli et al., Biol Chem, 1999, 380(5):553–9, DeLisser H M, Methods Mol Biol, 1999, 96:11–20, Van de Water et al., Clin Immunol Immunopathol, 1997, 85(3):229–35, Saint-Remy J M, Toxicology, 1997, 119(1):77–81, and Lane D P and Stephen C W, Curr Opin Immunol, 1993, 5(2):268–71. One method is to establish a phage display library expressing random oligopeptides of e.g. 9 amino acid residues. IgG1 antibodies from specific antisera towards [S99T]huIFNG, huIFNG or rhuIFNG are purified by immunoprecipitation and the reactive phages are identified by immunoblotting. By sequencing the DNA of the purified reactive phages, the sequence of the oligopeptide can be determined followed by localization of the sequence on the 3D-structure of the IFNG. The thereby identified region on the structure constitutes an epitope that then can be selected as a target region for introduction of an attachment group for the non-polypeptide moiety.

Functional in vivo half-life and serum half-life is e.g. dependent on the molecular weight of the polypeptide variant and the number of attachment groups needed for providing increased half-life may depend on the molecular weight of the non-polypeptide moiety in question. In one embodiment, the IFNG polypeptide variant of the invention has a molecular weight of at least 67 kDa, in particular at least 70 kDa as measured by SDS-PAGE according to Laemmli, U. K., Nature Vol 227 (1970), p680–85. IFNG has a Mw in the range of about 34–50 kDa, and therefore additional about 20–40 kDa is required to obtain the desired effect. This may, e.g., be provided by 2–4 10 kDa PEG molecules or by a combination of additional in vivo glycosylation sites and additional PEG molecules, or as otherwise described herein.

Preferably, a conjugated IFNG polypeptide variant according to the invention comprises 1–10 (additional) non-polypeptide moieties, such as 1–8, 2–8, 1–5, 1–3 or 2–5 (additional) non-polypeptide moieties. Typically, a conjugated variant comprises 1–3 (additional) non-polypeptide moieties, such as 1, 2 or 3 (additional) non-polypeptide moieties.

As mentioned above, under physiological conditions huIFNG exists as a dimeric polypeptide. The polypeptide is normally in homodimeric form (e.g. prepared by association of two IFNG polypeptide molecules prepared as described herein). However, if desired the IFNG polypeptide variant may be provided in single chain form, wherein two IFNG polypeptide monomers are linked via a peptide bond or a peptide linker. Providing the IFNG polypeptide variant in single chain form has the advantage that the two constituent IFNG polypeptides may be different which can be advantageous, e.g., to enable asymmetric mutagenesis of the polypeptides. For instance, PEGylation sites can be removed from the receptor-binding site from one of the monomers, but retained in the other. Thereby, after PEGylation one monomer has an intact receptor-binding site, whereas the other may be fully PEGylated (and thus provide significantly increased molecular weight).

As mentioned above, such variants have an $AUC_{sc}$ when administered subcutaneously, which is statistically significantly increased relative to that of a reference molecule, such as huIFNG (SEQ ID NO:17), [S99T]huIFNG (SEQ ID NO:1), huIFNG-132 (SEQ ID NO:29), [S99T]huIFNG-132 (SEQ ID NO:12), in their glycosylated forms, or ACTIMMUNE® (SEQ ID NO:34—produced in *E. coli*), determined under comparable conditions. Thus, preferred IFNG variants are such variants, which have an increased $AUC_{sc}$, as compared to any of the reference molecules mentioned above. Evidently, the same amount of IFNG activity should be administered for the IFNG variant of the invention and the reference molecule. Consequently, in order to make direct comparisons between different IFNG molecules, the $AUC_{sc}$ values may be normalized, i.e. they may be expressed as $AUC_{sc}$/dose administered.

Particular preferred IFNG variants are such variants where the ratio between the $AUC_{sc}$ of said variant and the $AUC_{sc}$ of huIFNG, [S99T]huIFNG, huIFNG-132 or [S99T]huIFNG-132, in their glycosylated forms, is at least 1.25, such as at least 1.5, e.g. at least 2, more preferably at least 3, such as at least 4, e.g. at least 5 or at least 6, even more preferably at least 7, such as at least 8, e.g. at least 9 or at least 10, most preferably at least 12, such as at least 14, e.g. at least 16, at least 18 or at least 20, in particular when administered (subcutaneously) in rats.

Other examples of particular preferred IFNG variants are such variants where the ratio between the $AUC_{sc}$ of said variant and the $AUC_{sc}$ of ACTIMMUNE® IFNG is at least 100, more preferably at least 150, such as at least 200, e.g. at least 250, even more preferably at least 300, such as at least 400 e.g. at least 500, most preferably at least 750, such as at least 1000, e.g. at least 1500 or at least 2000, in particular when administered (subcutaneously) in rats.

In addition, such variants preferably have an increased $T_{max,sc}$ as compared to huIFNG, [S99T]huIFNG, huIFNG-132 or [S99T]huIFNG-132, in their glycosylated forms, or ACTIMMUNE® IFNG. More particularly, such preferred variants have a $T_{max,sc}$ (when determined after subcutaneous administration in rats) of at least 200 min, such as at least 250 mm, e.g. at least 300 min, more preferably at least 350 min, such as at least 400 min.

Moreover, such variants preferably have a functional in vivo half-life or serum half-life which variant is statistically significantly increased relative to that of a reference molecule, such as huIFNG (SEQ ID NO:17), [S99T] huIFNG (SEQ ID NO:1), huIFNG-132 (SEQ ID NO:29), [S99T]huIFNG-132 (SEQ ID NO:12), in their glycosylated forms, or ACTIMMUNE® IFNG (SEQ ID NO:34—produced in E. coli), when administered intravenously and when determined under comparable conditions. Thus, interesting IFNG polypeptide variants are such variants, which have an increased functional in vivo half-life or an increased serum half-life as compared to any of the reference molecules mentioned above.

More particularly, interesting IFNG variants are such variants where the ratio between the serum half-life (or functional in vivo half-life) of said variant and the serum half-life (or functional in vivo half-life) of huIFNG, [S99T] huIFNG, huIFNG-132 or [S99T]huIFNG-132, in their glycosylated forms, is at least 1.25, more preferably at least 1.50, such as at least 1.75, e.g. at least 2, even more preferably at least 3, such as at least 4, e.g. at least 5, when administered intravenously, in particular when administered intravenously in rats.

Other examples of interesting IFNG variants are such variants where the ratio between the serum half-life (or functional in vivo half-life) of said variant and the serum half-life (or functional in vivo half-life) of ACTIMMUNE® IFNG (SEQ ID NO:34—produced in E. coli) is at least 2 more preferably at least 3, such as at least 4, e.g. at least 5, even more preferably at least 6, such as at least 7, e.g. at least 8, most preferably at least 9, such as at least 10, when administered intravenously, in particular when administered intravenously in rats.

Specific examples of variants possessing one or more of the above-mentioned characteristics are given in the below sections entitled "IFNG variants of the invention wherein the non-polypeptide moiety is a sugar moiety", "IFNG variants of the invention wherein the non-polypeptide moiety is a molecule, which has cysteine as an attachment group" and "IFNG variants of the invention wherein the first non-polypeptide moiety is a sugar moiety and the second non-polypeptide moiety is a molecule, which has cysteine as an attachment group".

IFNG Variants of the Invention Wherein the Non-polypeptide Moiety is a Sugar Moiety In a preferred embodiment of the invention the IFNG variant of SEQ ID NO:1 (or fragments thereof, such as SEQ ID NO:12) comprises at least one introduced glycosylation site and/or at least one removed glycosylation site. Preferably, the glycosylation site is an in vivo N-glycosylation site, i.e. the non-polypeptide moiety is a sugar moiety, e.g. an O-linked or N-linked sugar moiety, preferably an N-linked sugar moiety.

In one interesting embodiment of the invention said variant comprises at least one introduced glycosylation site, in particular an introduced in vivo N-glycosylation site. Preferably, the introduced glycosylation site is introduced by a substitution.

For instance, an in vivo N-glycosylation site may be introduced into a position of the IFNG polypeptide of SEQ ID NO:1 (of fragments thereof, such as SEQ ID NO:12) comprising an amino acid residue exposed to the surface. Preferably said surface-exposed amino acid residue has at least 25% of the side chain exposed to the surface, in particular at least 50% of its side chain exposed to the surface. Details regarding determination of such positions can be found in Example 1 herein.

The N-glycosylation site is introduced in such a way that the N-residue of said site is located in said position. Analogously, an O-glycosylation site is introduced so that the S or T residue making up such site is located in said position. It should be understood that when the term "at least 25% (or 50%) of its side chain exposed to the surface" is used in connection with introduction of an in vivo N-glycosylation site this term refers to the surface accessibility of the amino acid side chain in the position where the sugar moiety is actually attached. In many cases it will be necessary to introduce a serine or a threonine residue in position +2 relative to the asparagine residue to which the sugar moiety is actually attached and these positions, where the serine or threonine residues are introduced, are allowed to be buried, i.e. to have less than 25% (or 50%) of their side chains exposed to the surface of the molecule.

Furthermore, in order to ensure efficient glycosylation it is preferred that the in vivo glycosylation site, in particular the N residue of the N-glycosylation site or the S or T residue of the O-glycosylation site, is located within the 118 N-terminal amino acid residues of the IFNG polypeptide, more preferably within the 97 N-terminal amino acid residues. Still more preferably, the in vivo glycosylation site is introduced into a position wherein only one mutation is required to create the site (i.e. where any other amino acid residues required for creating a functional glycosylation site is already present in the molecule).

For instance, substitutions that lead to introduction of an additional N-glycosylation site at positions exposed at the surface of the IFNG polypeptide and occupied by amino acid residues having at least 25% of the side chain exposed to the surface (in a structure with receptor molecule) include:

Q1N+P3S/T, P3N+V5S/T, K6N+A8S/T, E9N+L11S/T, K12S/T, K13N+F15S/T, Y14N+N16S/T, G18S/T, G18N, G18N+S20T, H19N+D21S/T, D21N+A23S/T, G26N+L28S/T, G31N+L33S/T, K34N+W36S/T, K37S/T, K37N+E39S/T, E38N, E38N+S40T, E39N+D41S/T, S40N+R42S/T, K55N+F57S/T, K58N+F60S/T, K61S/T, K61N+D63S/T, D62N+Q64S/T, D63N, D63N+S65T, Q64N+I66S/T, S65N+Q67S/T, Q67N, Q67N+S69T, K68N+V70S/T, E71N+I73S/T, T72N+K74S/T, K74N+D76S/T, E75N+M77S/T, K80S/T, V79N+F81S/T, K80N+F82S/T, N85S/T, S84N+K86S/T, K87S/T, K86N+K88S/T, K87N+R89S/T, D90N+F92S/T, E93N+L95S/T, K94N, K94N+T96S, T101+L103S/T, D102N+N104S/T, L103N+V105S/T, Q106S/T, E119N, E119N+S121T, P122N+A124S/T, A123N+K125S/T,

A124N, A124N+T126S, K125N+G127S/T, T126N+K128S/ T, G127N+R129S/T, K128N+K130S/T, R129N+R131S/T, K130N, K130N+S132T, R131N+Q133S/T, S132N+M134S/ T, Q133N+L135S/T, M134N+F136S/T, L135N+R137S/T, F136N+G138S/T, R137N+R139S/T, G138N+R140S/T, R139N+A141S/T, R140N and R140N+S142T, the substitution being indicated relative to [S99T]huIFNG with the amino acid sequence shown in SEQ ID NO 1 (or relative to the relevant fragment thereof having the amino acid sequence shown in SEQ ID NOS:2–16, e.g. SEQ ID NO:12). S/T indicates a substitution to a serine or threonine residue, preferably a threonine residue.

Substitutions that lead to introduction of an additional N-glycosylation site at positions exposed at the surface of the IFNG polypeptide having at least 50% of the side chain exposed to the surface (in a structure with receptor molecule) include:
P3N+V5S/T, K6N+A8S/T, K12S/T, K13N+F15S/T, G18S/ T, D21N+A23S/T, G26N+L28S/T, G31N+L33S/T, K34N+ W36S/T, K37N+E39S/T, E38N, E38N+S40S/T, E39N+ D41S/T, K55N+F57S/T, K58N+F60S/T, K61S/T, D62N+ Q64S/T, Q64N+I66S/T, S65N+Q67S/T, K68N+V70S/T, E71N+I73S/T, E75N+M77S/T, N85S/T, S84N+K86S/T, K86N+K88S/T, K87N+R89S/T, K94N, K94N+T96S, T101N+L103S/T, D102N+N104S/T, L103N+V105S/T, Q106S/T, P122N+A124S/T, A123N+K125S/T, A124N, A124N+T126S, K125N+G127S/T, T126N+K128S/T, G127N+R129S/T, K128N+K130S/T, R129N+R131S/T, K130N, K130N+S132T, R131N+Q133S/T, S132N+M134S/ T, Q133N+L135S/T, M134N+F136S/T, L135N+R137S/T, F136N+G138S/T, R137N+R139S/T, G138N+R140S/T, R139N+A141S/T, R140N and R140N+S142T, the substitution being indicated relative to [S99T]huIFNG with the amino acid sequence shown in SEQ ID NO 1 (or relative to the relevant fragment thereof having the amino acid sequence shown in SEQ ID NOS:2–16, e.g. SEQ ID NO:12). S/T indicates a substitution to a serine or threonine residue, preferably a threonine residue.

Substitutions where only one amino acid substitution is required to introduce an N-glycosylation site include K12S/ T, G18S/T, G18N, K37S/T, E38N, M45N, I49N, K61S/T, D63N, Q67N, V70N, K80S/T, F82N,N85S/T, K87S/T, K94N, Q106S/T, E119N, A124N, K130N and R140N, in particular K12S/T, G18N, G18S/T, K37S/T, E38N, K61S/T, D63N, Q67N, K80S/T, N85S/T, K94N, Q106S/T, A124N, K130N, and R140N (positions with more than 25% of its site chain exposed to the surface (in a structure without receptor molecule)), or more preferably G18N, E38N, D63N, Q67N, K94N, S99N, A124N, K130N and R140N (positions with more than 50% of its side chain exposed to the surface in a structure without receptor molecule).

Usually, it is not preferred to introduce N-glycosylation sites in the region constituting the receptor binding site (except in special cases, cf. the section entitled "Variants with a reduced receptor affinity"). Accordingly, the mutations Q1N+P3S/T, E9N+L11S/T, G18N, G18N+S20T, H19N+D21S/T, D21N+A23S/T, G26N+L28S/T, K34N+ W36S/T, K37N+E39S/T, E119N and E119N+S121T should normally not be performed, unless a reduced receptor affinity is desired.

Particular preferred variants of the present invention include a variant of SEQ ID NO:1 (or fragments thereof having the amino acid sequence shown in SEQ ID NOS:2–16, in particular SEQ ID NO:12), wherein said variant exhibits IFNG activity and which comprises at least one substitution selected from the group consisting of K12S, K12T, G18S, G18T, E38N, E38N+S40T, K61S, K61T, S65N+Q67S, S65N+Q67T, N85S, N85T, K94N, Q106S and Q106T, more preferably selected from the group consisting of K12T, G18T, E38N+S40T, K61T, S65N+Q67T, N85T, K94N and Q106T, even more preferably selected from the group consisting of K12T, G18T, E38N+S40T, K61T, S65N+Q67T and N85T, in particular E38N+S40T.

In another interesting embodiment of the invention, the variant of SEQ ID NO:1 (or fragments thereof having the amino acid sequence shown in SEQ ID NOS:2–16, in particular SEQ ID NO:12) comprises at least two introduced glycosylation sites, in particular at least two introduced N-glycosylation sites. The at least two modifications, in particular substitutions, leading to the introduction of the at least two introduced N-glycosylation sites may preferably be selected from the group consisting of K12S, K12T, G18S, G18T, E38N, E38N+S40T, K61S, K61T, S65N+Q67S, S65N+Q67T, N85S, N85T, K94N, Q106S and Q106T, more preferably selected from the group consisting of K12T, G18T, E38N+S40T, K61T, S65N+Q67T, N85T, K94N and Q106T, even more preferably selected from the group consisting of K12T, G18T, E38N+S40T, K61T, S65N+Q67T and N85T. Specific examples of such substitutions giving rise to a variant comprising at least two additional N-glycosylation sites include: K12T+G18T, K12T+E38N+ S40T, K12T+K61T, K12T+S65N+Q67T, K12T+N85T, G18T+E38N+S40T, G18T+K61T, G18T+S65N+Q67T, G18T+N85T, E38N+S40T+K61 T, E38N+S40T+S65N+ Q67T, E38N+S40T+N85T, K61T+S67N+Q67T, K61T+ N85T and S65N+Q67T+N85T From the above lists of substitutions, it is preferable to select substitutions located within the 118 N-terminal amino acid residues, in particular within the 97 N-terminal amino acid residues.

The IFNG polypeptide variant of the invention may contain a single additional in vivo glycosylation site per monomer (as compared to SEQ ID NO:1 or fragments thereof, such as SEQ ID NO:12). However, in order to become of a sufficient size to increase the serum half-life it is often desirable that the polypeptide comprises more than one additional in vivo N-glycosylation site, in particular 2–7 or 2–5 additional in vivo N-glycosylation sites, such as 2, 3, 4 or 5 in vivo N-glycosylation sites. Such in vivo N-glycosylation sites are preferably introduced by one or more substitutions described in any of the above lists.

In another embodiment of the invention, the N-glycosylation site present in position 25 has been removed, preferably by substitution. This may be achieved by performing a substitution of the N25 residue with any other amino acid residue, such as N25G or N25C. In a preferred embodiment, the N-glycosylation site is removed by the substitution N25G. Alternatively, the N-glycosylation site may be removed by performing a substitution of the T27 residue with any other amino acid residue, except serine, such as T27P or T27C. In a preferred embodiment, the N-glycosylation site is removed by performing the substitution T27P. In another embodiment the N-glycosylation site in position 25 is removed by performing substitutions in both of the positions N25 and T27, such as N25G+T27P.

In addition to the removal of the N-glycosylation site at position 25, the variant may comprise at least one introduced N-glycosylation site, which is introduced at a position different from position 25. As will be understood, this additional N-glycosylation site is preferably introduced in the positions discussed above, in particular by the substitutions E38N+S40T.

Furthermore, it will be understood that any of the above-mentioned modifications may be combined with any of the modifications disclosed in the section entitled "IFNG variant of the invention with optimised in vivo glycosylation sites" as well as with any of the modifications disclosed in the section entitled "IFNG variant of the invention wherein the non-polypeptide moiety is a molecule, which has cysteine as an attachment group"

IFNG Variants of the Invention Wherein the Non-polypeptide Moiety is a Molecule, which has Cysteine as an Attachment Group In another preferred embodiment of the invention the IFNG variant of SEQ ID NO:1 (or fragments thereof, such as SEQ ID NO:12) comprises at least one introduced cysteine residue. For instance, a cysteine residue may be introduced into a position of the IFNG polypeptide of SEQ ID NO:1 (or fragments thereof, such as SEQ ID NO:12) comprising an amino acid residue exposed to the surface. Preferably said surface-exposed amino acid residue has at least 25% of the side chain exposed to the surface, in particular at least 50% of its side chain exposed to the surface. Details regarding determination of such positions can be found in Example 1 herein.

For instance, substitutions that lead to introduction of a cysteine residue at positions exposed at the surface of the IFNG polypeptide and occupied by amino acid residue having at least 25% of the side chain exposed to the surface (in a structure with receptor molecule) include: Q1C, D2C, P3C, K6C, E9C, N10C, K13C, Y14C, N16C, G18C, H19C, D21C, N25C, G26C, G30C, K34C, N35C, K37C, E38C, E39C, S40C, K55C, K58C, N59C, K61C, D62C, D63C, Q64C, S65C, Q67C, K68C, E71C, T72C, K74C, E75C, N78C, V79C, K80C, N83C, S84C, N85C, K86C, K87C, D90C, E93C, K94C, T101C, D102C, L103C, N104C and E119C, the substitution being indicated relative to [S99T] huIFNG with the amino acid sequence shown in SEQ ID NO 1 (or relative to the relevant fragment thereof having the amino acid sequence shown in SEQ ID NOS:2–16, in particular SEQ ID NO:12).

Substitutions that lead to introduction of a cysteine residue at positions exposed at the surface of the IFNG polypeptide and occupied by amino acid residue having at least 50% of the side chain exposed to the surface (in a structure with receptor molecule) include: P3C, K6C, N10C, K13C, N16C, D21C, N25C, G26C, G31C, K34C, K37C, E38C, E39C, K55C, K58C, N59C, D62C, Q64C, S65C, K68C, E71C, E75C, N83C, S84C, K86C, K87C, K94C, T101C, D102C, L103C and N104C, the substitution being indicated relative to [S99T]huIFNG with the amino acid sequence shown in SEQ ID NO 1 (or relative to the relevant fragment thereof having the amino acid sequence shown in SEQ ID NOS:2–16, in particular SEQ ID NO:12).

Usually, it is not preferred to introduce a cysteine residue (and subsequently attaching the cysteine residue to a non-polypeptide moiety) in the region constituting the receptor binding site (except in special cases, cf. the section entitled "Variants with a reduced receptor affinity"). Accordingly, the mutations Q1C, E9C, G18C, H19C, D21C, G26C, K34C, K37C and E119C should normally not be performed, unless a reduced receptor affinity is desired.

More preferably, said cysteine residue is introduced by a substitution selected from the group consisting of N10C, N16C, E38C, N59C, S65C, N83C, K94C, N104C and A124C.

In another interesting embodiment of the invention, the variant of SEQ ID NO:1 (or fragments thereof having the amino acid sequence shown in SEQ ID NOS:2–16, in particular SEQ ID NO:12) comprises at least two introduced cysteine residues. The at least two modifications, in particular substitutions, leading to the introduction of the at least two cysteine residues may preferably be selected from the group consisting of N10C, N16C, E38C, N59C, S65C, N83C, K94C, N104C and A124C. Specific examples of such substitutions giving rise to a variant comprising at least two introduced cysteine residues include: N10C+N16C, N10C+E38C, N10C+N59C, N10C+S65C, N10C+N83C, N10C+K94C, N10C+N104C, N10C+A124C, N16C+E38C, N16C+N59C, N16C+S65C, N16C+N83C, N16C+K94C, N16C+N104C, N16C+A124C, E38C+N59C, E38C+S65C, E38C+N83C, E38C+K94C, E38C+N104C, E38N+A124C, N59C+S65C, N59C+N83C, N59C+K94C, N59C+N104C, N59C+A124C, S65C+N83C, S65C+K94C, S65C+N104C, S65C+A124C, N83C+K94C, N83C+K94C, N83C+N104C, N83C+A124C, K94C+N104C, K94C+A124C and N104C+A124C.

As will be understood the introduced cysteine residue(s) may preferably be conjugated to a non-polypeptide moiety, such as PEG or more preferably mPEG. The conjugation between the cysteine-containing polypeptide variant and the polymer molecule may be achieved in any suitable manner, e.g. as described in the section entitled "Conjugation to a polymer molecule", e.g. in using a one step method or in the stepwise manner referred to in said section. The preferred method for PEGylating the IFNG polypeptide variant is to covalently attach PEG to cysteine residues using cysteine-reactive PEGs. A number of highly specific, cysteine-reactive PEGs with different groups (e.g. orthopyridyl-disulfide, maleimide and vinylsulfone) and different size PEGs (2–20 kDa, such as 5 kDa, 10 kDa, 12 kDa or 15 kDa) are commercially available, e.g. from Shearwater Polymers Inc., Huntsville, Ala., USA).

It will be understood that any of the above-mentioned modifications may be combined with any of the modifications disclosed in the section entitled "IFNG variants of the invention with optimised in vivo glycosylation sites" as well as with any of the modifications disclosed in the section entitled "IFNG variants of the invention wherein the non-polypeptide moiety is a sugar moiety".

IFNG Variants of the Invention Wherein the First Non-polypeptide Moiety is a Sugar Moiety and the Second Non-polypeptide Moiety is a Molecule, which has Cysteine as an Attachment Group In a further preferred embodiment of the invention the IFNG variant of SEQ ID NO:1 (or fragments thereof, such as SEQ ID NO:12) comprises at least one introduced N-glycosylation site and at least one introduced cysteine residue. Such variants may be prepared by selecting the residues described in the two preceding sections describing suitable positions for introducing N-glycosylation sites and cysteine residues, respectively. However, in a preferred embodiment of the invention said variant comprises substitutions selected from the group consisting of K12T+N16C, K12T+E38C, K12T+N59C, K12T+S65C, K12T+N83C, K12T+K94C, K12T+N104C, K12T+A124C, G18T+N10C, G18T+E38C, G18T+N59C, G18T+S65C, G18T+N83C, G18T+K94C, G18T+N104C, G18T+A124C, G18N+S20T+N10C, G18N+S20T+N16C, G18N+S20T+E38C, G18N+S20T+N59C, G18N+S20T+S65C, G18N+S20T+N83C, G18N+S20T+K94C, G18N+S20T+N104C, G18N+S20T+A124C, E38N+S40T+N10C, E38N+S40T+N16C, E38N+S40T+N59C, E38N+S40T+S65C, E38N+S40T+N83C, E38N+S40T+K94C, E38N+S40T+N104C, E38N+S40T+A124C, K61T+N10C, K61T+N16C, K61T+E38C, K61T+S65C, K61T+N83C, K61T+K94C, K61T+N104C, K61T+A124C, S65N+Q67T+N10C, S65N+Q67T+N16C, S65N+Q67T+E38C, S65N+Q67T+S65C, S65N+Q67T+N83C, S65N+Q67T+K94C, S65N+Q67T+N104C, S65N+Q67T+ A124C, N85T+N10C, N85T+N16C, N85T+E38C, N85T+ N59C, N85T+S65C, N85T+K94C, N85T+N104C, N85T+ A124C, K94N+N10C, K94N+N16C, K94N+E38C, K94N+ N59C, K94N+S65C, K94N+N83C, K94N+N104C, K94N+ A124C, Q106T+N10C, Q106T+N16C, Q106T+E38C, Q106T+N59C, Q106T+S65C, Q106T+N83C, Q106T+ K94C and Q106T+A124C, more preferably from the group consisting of E38N+S40T+N10C, E38N+S40T+N16C, E38N+S40T+N59C, E38N+S40T+S65C, E38N+S40T+ N83C, E38N+S40T+K94C, E38N+S40T+N104C and E38N+S40T+A124C.

As will be understood the introduced cysteine residue may preferably be conjugated to a non-polypeptide moiety, such as PEG or more preferably mPEG. The conjugation between the cysteine-containing polypeptide variant and the polymer may be achieved in any suitable manner, e.g. as described in the section entitled "Conjugation to a polymer molecule", e.g. in using a one step method or in the stepwise manner referred to in said section. A suitable polymer is VS-mPEG or OPSS-mPEG.

In a similar way as described above (see the section entitled "IFNG variants of the invention wherein the non-polypeptide moiety is a sugar moiety") the N-glycosylation site present in position 25 may be removed, preferably by a substitution. Thus, in a further embodiment of the invention, the N-glycosylation site at position 25 has been removed, preferably by substitution, such as by the substitution N25G, N25C, T27P or N25G+T27P, and the at least one cysteine residue has been introduced. As will be understood, this additional cysteine residue is preferably introduced in the positions discussed above.

Moreover, the N-glycosylation site at position 25 may be removed, preferably by substitution, such as by the substitution N25G, N25C, T27P or N25G+T27P, and at least one N-glycosylation site may be introduced in a position different from position 25 and at least one cysteine residue may be introduced. As will be understood, this additional cysteine residue and the additional N-glycosylation site are preferably introduced in the positions discussed above.

Furthermore, it will be understood that any of the above-mentioned modifications may be combined with any of the modifications disclosed in the section entitled "IFNG variant of the invention with optimised in vivo glycosylation sites".

IFNG Variants with a Reduced Receptor Affinity

One way to increase the serum half-life of an IFNG polypeptide would be to decrease the receptor-mediated internalisation and thereby decrease the receptor-mediated clearance.

The receptor-mediated internalisation is dependent upon the affinity of the IFNG dimer for the IFNG receptor complex and, accordingly, an IFNG variant with a decreased affinity to the IFNG receptor complex is expected to be internalised, and hence cleared, to a lesser extent.

The affinity of the IFNG dimmer to its receptor complex may be decreased by performing one or more modifications, in particular substitutions, in the receptor binding site of the IFNG polypeptide. The amino acid residues which constitute the receptor binding site is defined in Example 2 herein. One class of substitutions that may be performed is conservative amino acid substitutions. In another embodiment, the modification performed gives rise to the introduction of an N-glycosylation site.

Thus, in a further particular preferred embodiment of the invention the IFNG variant of SEQ ID NO:1 (or fragments thereof, such as SEQ ID NO:12) comprises at least one modification, such as a substitution, in the receptor binding site (as defined herein). More particularly, the IFNG polypeptide comprises at least one modification, preferably a substitution, which creates an in vivo N-glycosylation site, in said receptor binding site. For instance, such substitutions may be selected from the group consisting of Q1N+P3S/T, D2N+Y4S/T, Y4N+K6S/T, V5N+E7S/T, E9N+L11S/T, K12N+Y14S/T, G18N, G18N+S20T, H19N+D21S/T, S20N+V22S/T, D21N+A23S/T, V22N+D24S/T, D24N+ G26S/T, G26N+L28S/T, L30N+I32S/T, K34N+W36S/T, K37N+E39S/T, K108N+I110S/T, H111N+L113S/T, E112N+I114S/T, I114N+V116S/T, Q115N+M117S/T, A118N+L120S/T, E119N and E119N+S121T, preferably from the group consisting of Q1N+P3S/T, D2N+Y4S/T, E9N+L11S/T, K12N+Y14S/T, G18N, G18N+S20T, H19N+ D21S/T, S20N+V22S/T, D21N+A23S/T, K34N+W36S/T, K37N+E39S/T, H111N+L113S/T, Q115N+M117S/T, A118N+L120S/T, E119N and E119N+S121T (introduction of N-glycosylation sites in positions comprising an amino acid residue having at least 25% of its side chain exposed to the surface), more preferably from the group consisting of Q1N+P3S/T, D2N+Y4S/T, E9N+L11S/T, G18N, G18N+ S20T, H19N+D21S/T, S20N+V22S/T, D21N+A23S/T, K34N+W36S/T, K37N+E39S/T, Q115N+M117S/T, A118N+L120S/T, E119N and E119N+S121T (introduction of N-glycosylation sites in positions comprising an amino acid residue having at least 50% of its side chain exposed to the surface), even more preferably from the group consisting of Q1N+P3T, D2N+Y4T, E9N+L11T, G18N+S20T, H19N+ D21T, S20N+V22T, D21N+A23T, K34N+W36T, K37N+ E39T, Q115N+M117T, A118N+L120T and E119N+S121T, most preferably from the group consisting of G18N+S20T, H19N+D21T, D21N+A23T and E119N+S121T, in particular D21N+A23T.

Such variants are contemplated to exhibit a reduced receptor affinity as compared to huIFNG, [S99T]huIFNG, huIFNG-132 or [S99T]huIFNG-132, in their glycosylated forms, or ACTIMMUNE® IFNG. The receptor affinity may be measured by any suitable assay and will be known to the person skilled in the art. One example of a suitable assay for determining the receptor binding affinity is the BIACORE® assay described in Michiels et al. Int. J. Biochem. Cell Biol. 30:505–516 (1998). Using the above-identified assay, IFNG variants considered useful for the purposes described herein are such IFNG variants, wherein the binding affinity ($K_d$) is 1–95% of the $K_d$-value of huIFNG, [S99T]huIFNG, huIFNG-132 or [S99T]huIFNG-132, in their glycosylated forms, or ACTIMMUNE® IFNG. For example the $K_d$-value of the IFNG polypeptide may be 1–75% or 1–50%, such as 1–25%, e.g. 1–20% or even as low as 1–15%, 1–10% or 1–5% of the $K_d$-value of huIFNG, [S99T]huIFNG, huIFNG-132 or [S99T]huIFNG-132, in their glycosylated forms, or ACTIMMUNE® IFNG.

Typically, such IFNG variants having reduced receptor affinity will exhibit a reduced IFNG activity, e.g. when tested in the "Primary Assay" described herein. For example, the IFNG polypeptide variant may exhibit 1–95% of the specific activity of huIFNG, [S99T]huIFNG, huIFNG-132 or [S99T]huIFNG-132, in their glycosylated forms, or ACTIMMUNE® IFNG, e.g. 1–75%, such as 1–50%, e.g. 1–20%, 1–10% or 1–5% of the specific activity of huIFNG, [S99T]huIFNG, huIFNG-132 or [S99T]huIFNG-132, in their glycosylated forms, or ACTIMMUNE® IFNG.

As mentioned above, such IFNG variants are contemplated to possess an increased serum-half due to the reduced receptor-mediated clearance. Therefore, the IFNG polypeptide variants according to the aspect of the invention are contemplated to fulfil the requirements with respect to increased serum-half described previously herein in connection with the definition of increased serum half-life.

Evidently, any of the above-mentioned modifications giving rise to a reduced receptor binding affinity may be combined with any of the other modifications disclosed herein, in particular the modifications mentioned in the sections entitled "IFNG variants of the invention with optimised N-glycosylation sites", "IFNG variants of the invention wherein the non-polypeptide moiety is a sugar moiety", "IFNG variants of the invention wherein the non-polypeptide moiety is a molecule, which has cysteine as an attachment group" and "IFNG variants of the invention wherein the first non-polypeptide moiety is a sugar moiety and the second non-polypeptide moiety is a molecule, which has cysteine as an attachment group", such as E38N+S40T.

[S99T]huIFNG-132 (SEQ ID NO:12), huIFNG-132 (SEQ ID NO:29) and Variants Thereof

It is known that when IFNG is produced in mammalian cell lines a heterogenous population of IFNG polypeptides is obtained due to C-terminal truncation of the IFNG polypeptide (reviewed in Lundell et al. *Pharmac. Ther.* 64, 1–21, 1994). Clearly, this constitutes a severe problem in that valuable polypeptide material is lost and, further, it is necessary to carry out time-consuming and cumbersome purification in order to obtain a homogenous population of active IFNG polypeptides having the desired length. Most likely, this truncation is effected by endo- and/or exoprotease activity produced by the host cell.

As will be evident from the examples provided herein, C-terminal truncation is not only a phenomena related to the full-length IFNG molecule. It has been found that if the "genetically truncated" IFNG molecules are expressed in a eukaryotic host cell, for example a "genetically truncated" IFNG polypeptide comprising 135 amino acids, such fragments are further truncated during production. However, it has now surprisingly been found that a "genetically truncated" IFNG fragment comprising 132 amino acid residues does not undergo C-terminal truncation or, at least is, not significantly C-terminally truncated. Furthermore, as the IFNG fragment containing 132 amino acid residues is active, this opens up the possibility of producing a homogenous active IFNG polypeptide in eukaryotic host cells, such as mammalian host cells, such as CHO cells, in particular CHO-K1 cells. When used herein the term "genetically truncated" means truncation at the nucleotide level by introduction of a stop codon.

Thus, it is also an object of the present invention to provide IFNG fragments and variants thereof, which are not prone to C-terminal truncation during production, purification or storage.

Accordingly, in a very interesting aspect the present invention relates to an IFNG polypeptide variant exhibiting IFNG activity and having the amino acid sequence shown in SEQ ID NO:12 ([S99T]huIFNG-132). In a highly preferred embodiment of the invention, the variant comprises at least one further modification, such as 1–10 further modifications, relative to the amino acid sequence shown in SEQ ID NO:12. A particular preferred further modification is E38N+S40T.

Another aspect of the present invention relates to a nucleotide sequence encoding an IFNG polypeptide variant exhibiting IFNG activity and having the amino acid sequence shown in SEQ ID NO:12. In a still further aspect the present invention relates to a nucleotide sequence encoding an IFNG polypeptide variant exhibiting IFNG activity, wherein said variant comprises at least one modification, such as 1–10 modifications, relative to the amino acid sequence shown in SEQ ID NO:12. Thus, in the above aspects the present invention relates to a nucleotide sequence encoding a mature IFNG polypeptide variant exhibiting IFNG activity, wherein said variant is C-terminally truncated with 11 amino acid residues relative to the full-length of the mature IFNG polypeptide and wherein said nucleotide sequence comprises a stop-codon immediately downstream of codon 132 of the mature form of the IFNG polypeptide variant. A preferred example of an IFNG variant, which is C-terminally truncated with 11 amino acid residues include SEQ ID NO:12 ([S99T] huIFNG-132) as well as SEQ ID NO:12 further comprising the substitutions E38N+S40T ([E38N+S40T+S99T] huIFNG-132). Examples of stop codons include TAA, TGA and TAG.

An additional aspect of the present invention relates to a nucleotide sequence encoding a polypeptide having the amino acid sequence shown in SEQ ID NO:29. It will be understood that SEQ ID NO:29 further contains a stop-codon immediately downstream of the codon encoding the C-terminal amino acid residue of the IFNG polypeptide.

In a still further aspect the present invention relates a population of IFNG polypeptide variants, or to a composition comprising a population of IFNG polypeptide variants, wherein said population comprises at least 70%, preferably at least 75%, more preferably at least 80%, even more preferably at least 85%, such as about 90% of the IFNG polypeptide variant having the amino acid sequence shown in SEQ ID NO:12.

In an even further aspect the present invention relates a population of IFNG polypeptide variants, or to a composition comprising a population of IFNG polypeptide variants, wherein said population comprises at least 70%, preferably at least 75%, more preferably at least 80%, even more preferably at least 85%, such as about 90% of the IFNG polypeptide variant comprising 1–10 modifications relative to the amino acid sequence relative to the amino acid sequence shown in SEQ ID NO:12.

In a further aspect the present invention relates to a method for reducing or avoiding C-terminal heterogeneity of an IFNG polypeptide variant during its production, said method comprising:

(a) introducing a stop-codon immediately downstream of codon 132 in the nucleotide sequence of the mature form of the IFNG polypeptide variant; and (b) culturing a eukaryotic host cell comprising said nucleotide sequence under conditions conducive for expression of the polypeptide variant.

In another aspect the present invention relates to a method for reducing or avoiding C-terminal heterogeneity of an IFNG polypeptide during its production, said method comprising:

(a) introducing a stop-codon immediately downstream of codon 132 in the nucleotide sequence shown in SEQ ID NO:29; and (b) culturing a eukaryotic host cell comprising said nucleotide sequence under conditions conducive for expression of the polypeptide.

The eukaryotic host cell is preferably a mammalian cell, such as a CHO cell, in particular a CHO-K1 cell. Examples of stop codons include TAA, TGA and TAG.

It will be understood that all details and particulars concerning the full-length variants of the invention (such as, for example, preferred modifications, number of modifications, administration, indications for which the full-length variant may be used, etc.) will be the same or analogous to the IFNG variants being C-terminally truncated with 11 amino acid residues relative to the full-length IFNG polypeptide, whenever appropriate. Thus, statements and details concerning the "full-length variants" of the invention will apply mutatis mutandis to the variant fragments huIFNG-132 and [S99T]huIFNG-132, whenever appropriate.

It is known that the basic cluster K-R-K-R in positions 128–131 is required for activity and hence this region should normally not be altered. It is contemplated, however, that the C-terminal S132 residue may be substituted without significantly impairing the activity of the fragment. Thus, in a further embodiment the variant of the invention comprises a substitution in position S132. In particular, it is contemplated that the substitution S132C may be useful, in particular if the introduced cysteine residue is subsequently covalently attached to a non-polypeptide moiety, in particular mPEG.

Analysis of Truncation of IFNG Variants

Determination of C-terminal truncation of purified samples of IFNG variants can be carried out in a number of ways.

One way of elucidating C-terminal truncations of IFNG polypeptides relies on accurate mass determinations by mass spectrometry. Unfortunately, the glycosylation of IFNG is heterogeneous thus making it extremely difficult to determine an accurate mass directly on the glycoprotein. Therefore, different levels of enzymatic deglycosylation are typically used in combination with mass spectrometry.

In one method, the entire glycan part of the IFNG polypeptide is cleaved of using the endo-glycosidase PNGase F followed by accurate mass determination using either ESI mass spectrometry or MALDI-TOF mass spectrometry. Comparing the experimental masses to the known amino acid sequence of IFNG makes it possible to determine the sites of C-terminal truncation.

In another related method, only the sialic acid of the glycan part of the IFNG polypeptide is cleaved off instead of the entire glycan. In some cases this is sufficient to reduce the heterogeneity of the sample to a level where the sites of C-terminal truncations can be deduced following accurate mass determination using either ESI mass spectrometry or MALDI-TOF mass spectrometry.

A more traditional way of elucidating C-terminal truncations of IFNG polypeptides employs peptide mapping in combination with mass spectrometry and chemical amino acid sequencing. In brief, the IFNG polypeptide is degraded with a protease of known specificity (e.g. Asp-N protease) followed by peptide separation using RP-HPLC. Fractions can then by mass analysed either on-line using ESI mass spectrometry or off-line using MALDI-TOF mass spectrometry. Comparing the masses obtained for peptides with the known amino acid sequence of IFNG makes it possible to determine the likely sites of C-terminal truncation. Verification can then be obtained through amino acid sequencing.

Conjugation Methods

The Non-polypeptide Moiety

As indicated further above the non-polypeptide moiety is preferably selected from the group consisting of a polymer molecule, a lipophilic compound, a sugar moiety (e.g. by way of in vivo N-glycosylation) and an organic derivatizing agent. All of these agents may confer desirable properties to the IFNG polypeptide variant, in particular increased $AUC_{sc}$, increased serum half-life and/or reduced immunogenicity. The polypeptide variant is normally conjugated to only one type of non-polypeptide moiety, but may also be conjugated to two or more different types of non-polypeptide moieties, e.g. to a polymer molecule and a sugar moiety, to a lipophilic group and a sugar moiety, to an organic derivating agent and a sugar moiety, to a lipophilic group and a polymer molecule, etc. When conjugated to two different types of non-polypeptide moieties these are preferably a sugar moiety and a polymer moiety. The conjugation to two or more different non-polypeptide moieties may be done simultaneous or sequentially. In the following sections "Conjugation to a lipophilic compound", "Conjugation to a polymer molecule", "Conjugation to a sugar moiety" and "Conjugation to an organic derivatizing agent" conjugation to specific types of non-polypeptide moieties is described.

Conjugation to a Lipophilic Compound

The polypeptide variant and the lipophilic compound may be conjugated to each other, either directly or by use of a linker. The lipophilic compound may be a natural compound such as a saturated or unsaturated fatty acid, a fatty acid diketone, a terpene, a prostaglandin, a vitamine, a carotenoide or steroide, or a synthetic compound such as a carbon acid, an alcohol, an amine and sulphonic acid with one or more alkyl-, aryl-, alkenyl- or other multiple unsaturated compounds. The conjugation between the polypeptide variant and the lipophilic compound, optionally through a linker may be done according to methods known in the art, e.g. as described by Bodanszky in Peptide Synthesis, John Wiley, New York, 1976 and in WO 96/12505.

Conjugation to a Polymer Molecule

The polymer molecule to be coupled to the polypeptide variant may be any suitable polymer molecule, such as a natural or synthetic homo-polymer or heteropolymer, typically with a molecular weight in the range of 300–100,000 Da or 1000–50,000 Da, such as in the range of 2000–40,000 Da or 2000–30,000 Da, e.g. in the range of 2000–20,000 Da, 2000–10,000 or 1000–5000 Da. More particularly, the polymer molecule, such as PEG, in particular mPEG, will typically have a molecular weight of about 1, 2, 5, 10, 12, 15, 20, 30, 40 or 50 kDa, in particular a molecular weight of about 1 kDa, about 2 kDa, about 5 kDa, about 10 kDa, about 12 kDa, about 15 kDa or 20 about kDa.

When used about polymer molecules herein, the word "about" indicates an approximate average molecular weight and reflects the fact that there will normally be a certain molecular weight distribution in a given polymer preparation.

Examples of homo-polymers include a polyol (i.e. poly-OH), a polyamine (i.e. poly-$NH_2$) and a polycarboxylic acid (i.e. poly-COOH). A hetero-polymer is a polymer, which comprises one or more different coupling groups, such as, e.g., a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), polycarboxylate, poly-(vinylpyrolidone), polyethylene-co-maleic acid anhydride, polystyrene-co-malic acid anhydride, dextran including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule to be used, since it has only few reactive groups capable of cross-linking compared, e.g., to polysaccharides such as dextran, and the like. In particular, monofunctional PEG, such as, monomethoxypolyethylene glycol (mPEG), is of interest since its coupling chemistry is relatively simple (only one reactive group is available for conjugating with attachment groups on the polypeptide). Consequently, the risk of cross-linking is eliminated, the resulting conjugated polypeptide variantss are more homogeneous and the reaction of the polymer molecules with the polypeptide is easier to control.

To effect covalent attachment of the polymer molecule(s) to the polypeptide variant, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidy carboxymethylate (SCM), benzotriazole carbonate (BTC), N-hydroxysuccinimide (NHS), aldehyde, nitrophenylcarbonate (NPC), and tresylate (TRES)). Suitably activated polymer molecules are commercially available, e.g. from Shearwater Polymers, Inc., Huntsville, Ala., USA. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogue (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. Nos. 5,932,462 and 5,643,575, both of which references are incorporated herein by reference. Furthermore, the following publications, incorporated herein by reference, disclose useful polymer molecules and/or PEGylation chemistries: U.S. Pat. Nos. 5,824,778, 5,476,653, WO 97/32607, EP 229,108, EP 402,378, U.S. Pat. No. 4,902,502, 5,281,698, 5,122,614, 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. Nos. 5,473,034, 5,516,673, EP 605 963, U.S. Pat. No. 5,382,657, EP 510 356, EP 400 472, EP 183 503 and EP 154 316.

Specific examples of activated PEG polymers particularly preferred for coupling to cysteine residues, include the following linear PEGs: vinylsulfone-PEG (VS-PEG), preferably vinylsulfone-mPEG (VS-mPEG); maleimide-PEG (MAL-PEG), preferably maleimide-mPEG (MAL-mPEG) and orthopyridyl-disulfide-PEG (OPSS-PEG), preferably orthopyridyl-disulfide-mPEG (OPSS-mPEG). Typically, such PEG or mPEG polymers will have a size of about 1 kDa, about 2 kDa, about 5 kDa, about 10 kD, about 12 kDa or about 20 kDa.

The conjugation of the polypeptide variant and the activated polymer molecules is conducted by use of any conventional method, e.g. as described in the following references (which also describe suitable methods for activation of polymer molecules): Harris and Zalipsky, eds., Poly (ethylene glycol) Chemistry and Biological Applications, AZC, Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). For PEGylation to cysteine residues (see above) the IFNG variant is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6–9 at temperatures varying from 4° C. to 25° C. for periods up to 16 hours.

The skilled person will be aware that the activation method and/or conjugation chemistry to be used depends on the attachment group(s) of the polypeptide variant as well as the functional groups of the polymer (e.g. being amino, hydroxyl, carboxyl, aldehyde or sulfydryl). The PEGylation may be directed towards conjugation to all available attachment groups on the polypeptide variant (i.e. such attachment groups that are exposed at the surface of the polypeptide) or may be directed towards specific attachment groups, e.g. the N-terminal amino group (U.S. Pat. No. 5,985,265). Furthermore, the conjugation may be achieved in one step or in a stepwise manner (e.g. as described in WO 99/55377).

It will be understood that the PEGylation is designed so as to produce the optimal molecule with respect to the number of PEG molecules attached, the size and form (e.g. whether they are linear or branched) of such molecules, and where in the polypeptide variant such molecules are attached. For instance, the molecular weight of the polymer to be used may be chosen on the basis of the desired effect to be achieved. For instance, if the primary purpose of the conjugation is to achieve a conjugate having a high molecular weight (e.g. to reduce renal clearance) it is usually desirable to conjugate as few high molecular weight-polymer molecules as possible to obtain the desired molecular weight. When a high degree of epitope shielding is desirable this may be obtained by use of a sufficiently high number of low molecular weight polymer (e.g. with a molecular weight of about 5,000 Da) to effectively shield all or most epitopes of the polypeptide. For instance, 2–8, such as 3–6, of such polymers may be used.

In connection with conjugation to only a single attachment group on the protein (as described in U.S. Pat. No. 5,985,265), it may be advantageous that the polymer molecule, which may be linear or branched, has a high molecular weight, e.g. about 20 kDa.

Normally, the polymer conjugation is performed under conditions aiming at reacting all available polymer attachment groups with polymer molecules. Typically, the molar ratio of activated polymer molecules to polypeptide variant is 1000-1, in particular 200-1, e.g. 100-1, such as 10–1 or 5–1 in order to obtain optimal reaction. However, also equimolar ratios may be used.

It is also contemplated according to the invention to couple the polymer molecules to the polypeptide variant through a linker. Suitable linkers are well known to the skilled person. A preferred example is cyanuric chloride (Abuchowski et al., (1977), J. Biol. Chem., 252, 3578–3581; U.S. Pat. No. 4,179,337; Shafer et al., (1986), J. Polym. Sci. Polym. Chem. Ed., 24, 375–378.

Subsequent to the conjugation residual activated polymer molecules are blocked according to methods known in the art, e.g. by addition of primary amine to the reaction mixture, and the resulting inactivated polymer molecules removed by a suitable method.

Coupling to a Sugar Moiety

The coupling of a sugar moiety may take place in vivo or in vitro. In order to achieve in vivo glycosylation of a polypeptide with IFNG activity, which have been modified so as to introduce one or more in vivo glycosylation sites (see the section "IFNG variants of the invention wherein the non-polypeptide moiety is a sugar moiety), the nucleotide sequence encoding the polypeptide must be inserted in a glycosylating, eukaryotic expression host. The expression host cell may be selected from fungal (filamentous fungal or yeast), insect or animal cells or from transgenic plant cells. Furthermore, the glycosylation may be achieved in the human body when using a nucleotide sequence encoding the polypeptide variant of the invention in gene therapy. In one embodiment the host cell is a mammalian cell, such as an CHO cell, BHK or HEK cell, e.g. HEK293, or an insect cell, such as an SF9 cell, or a yeast cell, e.g. *Saccharomyces cerevisiae, Pichia pastoris* or any other suitable glycosylating host, e.g. as described further below. Optionally, sugar moieties attached to the IFNG polypeptide variant by in vivo glycosylation are further modified by use of glycosyltransferases, e.g. using the glycoAdvance™ technology marketed by Neose, Horsham, Pa., USA. Thereby, it is possible to, e.g., increase the sialyation of the glycosylated IFNG polypeptide variant following expression and in vivo glycosylation by CHO cells.

Covalent in vitro coupling of glycosides to amino acid residues of IFNG polypepeptides may be used to modify or increase the number or profile of carbohydrate substituents. Depending on the coupling mode used, the sugar(s) may be attached to a) arginine and histidine, b) free carboxyl groups, c) free sulfhydryl groups such as those of cysteine, d) free hydroxyl groups such as those of serine, threonine, tyrosine or hydroxyproline, e) aromatic residues such as those of phenylalanine or tryptophan or f) the amide group of glutamine. These amino acid residues constitute examples of attachment groups for a sugar moiety, which may be introduced and/or removed in the IFNG polypeptide. Suitable methods of in vitro coupling are described, for example, in WO 87/05330 and in Aplin et al., CRC Crit Rev. Biochem., pp. 259–306, 1981. The in vitro coupling of sugar moieties or PEG to protein- and peptide-bound Gln-residues can also be carried out by transglutaminases (TGases), e.g. as described by Sato et al., 1996 Biochemistry 35, 13072–13080 or in EP 725145.

Coupling to an Organic Derivatizing Agent

Covalent modification of the IFNG polypeptide variant may be performed by reacting (an) attachment group(s) of the polypeptide variant with an organic derivatizing agent. Suitable derivatizing agents and methods are well known in the art. For example, cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonateat pH 5.5–7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group. Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Blocking of Functional Site

It has been reported that excessive polymer conjugation can lead to a loss of activity of the polypeptide to which the polymer is conjugated. This problem can be eliminated, e.g., by removal of attachment groups located at the functional site or by blocking the functional site prior to conjugation. These latter strategies constitute further embodiments of the invention, the first strategy being exemplified further above, e.g. by removal of lysine residues which may be located close to the functional site and/or by introducing cysteine residues and/or in vivo glycosylation sites at positions not interfering with functional sites.

More specifically, according to the second strategy the conjugation between the polypeptide variant and the non-polypeptide moiety is conducted under conditions where the functional site of the IFNG polypeptide variant is blocked by a helper molecule capable of binding to the functional site of the polypeptide variant. Preferably, the helper molecule is one, which specifically recognizes a functional site of the polypeptide variant, such as a receptor. Alternatively, the helper molecule may be an antibody, in particular a monoclonal antibody recognizing the polypeptide variant. In particular, the helper molecule may be a neutralizing monoclonal antibody.

The polypeptide variant is then allowed to interact with the helper molecule before effecting conjugation. This ensures that the functional site of the polypeptide variant is shielded or protected and consequently unavailable for derivatization by the non-polypeptide moiety such, as a polymer. Following its elution from the helper molecule, the conjugate between the non-polypeptide moiety and the polypeptide variant can be recovered with at least a partially preserved functional site.

The subsequent conjugation of the polypeptide variant having a blocked functional site to a polymer, a lipophilic compound, a sugar moiety, an organic derivatizing agent or any other compound is conducted in the normal way, e.g. as described in the sections above entitled "Conjugation to . . . ".

In a further embodiment the helper molecule is first covalently linked to a solid phase such as column packing materials, for instance Sephadex or agarose beads, or a surface, e.g. reaction vessel. Subsequently, the polypeptide variant is loaded onto the column material carrying the helper molecule and conjugation carried out according to methods known in the art, e.g. as described in the sections above entitled "Conjugation to . . . ". This procedure allows the conjugated polypeptide variant to be separated from the helper molecule by elution. The conjugated polypeptide variant is eluted by conventional techniques under physicochemical conditions that do not lead to a substantive degradation of the conjugated polypeptide variant. The fluid phase containing the conjugated polypeptide variant is separated from the solid phase to which the helper molecule remains covalently linked. The separation can be achieved in other ways: For instance, the helper molecule may be derivatized with a second molecule (e.g. biotin) that can be recognized by a specific binder (e.g. streptavidin). The specific binder may be linked to a solid phase thereby allowing the separation of the conjugated polypeptide variant from the helper molecule-second molecule complex through passage over a second helper-solid phase column which will retain, upon subsequent elution, the helper molecule-second molecule complex, but not the conjugated polypeptide variant. The conjugated polypeptide variant may be released from the helper molecule in any appropriate fashion. De-protection may be achieved by providing conditions in which the helper molecule dissociates from the functional site of the polypeptide variant to which it is bound. For instance, a complex between an antibody to which a polymer is conjugated and an anti-idiotypic antibody can be dissociated by adjusting the pH to an acid or alkaline pH.

Conjugation of a Tagged Polypeptide Variant

In an alternative embodiment the IFNG polypeptide variant is expressed, as a fusion protein, with a tag, i.e. an amino acid sequence or peptide stretch made up of typically 1–30, such as 1–20 amino acid residues. Besides allowing for fast and easy purification, the tag is a convenient tool for achieving conjugation between the tagged IFNG polypeptide variant and the non-polypeptide moiety. In particular, the tag may be used for achieving conjugation in microtiter plates or other carriers, such as paramagnetic beads, to which the tagged polypeptide can be immobilised via the tag. The conjugation to the tagged IFNG polypeptide variantin, e.g., microtiter plates has the advantage that the tagged polypeptide variant can be immobilised in the microtiter plates directly from the culture broth (in principle without any purification) and subjected to conjugation. Thereby, the total number of process steps (from expression to conjugation) can be reduced. Furthermore, the tag may function as a spacer molecule ensuring an improved accessibility to the immobilised polypeptide variant to be conjugated. The conjugation using a tagged polypeptide variant may be to any of the non-polypeptide moieties disclosed herein, e.g. to a polymer molecule such as PEG.

The identity of the specific tag to be used is not critical as long as the tag is capable of being expressed with the polypeptide variant and is capable of being immobilised on a suitable surface or carrier material. A number of suitable tags are commercially available, e.g. from Unizyme Laboratories, Denmark. For instance, the tag may any of the following sequences:
His-His-His-His-His-His (SEQ ID NO:35),
Met-Lys-His-His-His-His-His-His (SEQ ID NO:36),
Met-Lys-His-His-Ala-His-His-Gln-His-His (SEQ ID NO:37),
Met-Lys-Gln-His-Gln-His-Gln-His-Gln-His-Gln-His-Gln (SEQ ID NO:38,
(all available from Unizyme Laboratories, Denmark)
or any of the following:
EQKLI SEEDL (SEQ ID NO:39) (a C-terminal tag described in Mol. Cell. Biol. 5:3610–16, 1985),
DYKDDDDK (SEQ ID NO:40) (a C- or N-terminal tag),
YPYDVPDYA (SEQ ID NO:41)

Antibodies against the above tags are commercially available, e.g. from ADI, Aves Lab and Research Diagnostics.

The subsequent cleavage of the tag from the polypeptide may be achieved by use of commercially available enzymes.

Methods of Preparing an IFNG Polypeptide Variant of the Invention

The IFNG polypeptide variant may be produced by any suitable method known in the art. Such methods include constructing a nucleotide sequence encoding the polypeptide variant and expressing the sequence in a suitable transformed or transfected host. However, polypeptide variants of the invention may be produced, albeit less efficiently, by chemical synthesis or a combination of chemical synthesis or a combination of chemical synthesis and recombinant DNA technology.

The nucleotide sequence of the invention encoding an IFNG polypeptide variant (in monomer or single chain form) may be constructed by isolating or synthesizing a nucleotide sequence encoding the parent IFNG, such as huIFNG with the amino acid sequence SEQ ID NO:17 and then changing the nucleotide sequence so as to effect introduction (i.e. insertion or substitution) or deletion (i.e. removal or substitution) of the relevant amino acid residue(s).

In case a truncated variant of the invention is desired, the nucleotide sequence encoding an IFNG polypeptide variant fragment may be constructed by synthesizing a nucleotide sequence encoding the parent IFNG fragment, such as fragments of huIFNG with the amino acid sequences shown in SEQ ID NOS:19–33, and then changing the nucleotide sequence so as to effect introduction (i.e. insertion or substitution) or deletion (i.e. removal or substitution) of the relevant amino acid residue(s). It will be understood that in such cases a stop-codon is introduced immediately downstream of the codon encoding the desired C-terminal amino acid residue. For example, in case a variant, which is C-terminally truncated with 11 amino acid residues (as compared to full-length IFNG gamma, i.e. a variant of SEQ ID NO:29) is desired, a suitable stop codon, such as TAA, TGA or TAG, is introduced immediately downstream of the codon encoding the 132th amino acid residue of the mature form of the IFNG polypeptide.

Thus, in an interesting aspect, the present invention relates to a nucleotide sequence encoding an IFNG polypeptide variant exhibiting IFNG activity, wherein said variant is C-terminally truncated with 1–15 amino acid residues and wherein said nucleotide sequence comprises a stop-codon immediately downstream of the codon encoding the C-terminal amino acid residue of the variant.

The nucleotide sequence is conveniently modified by site-directed mutagenesis in accordance with well-known methods, see, e.g., Mark et al., "Site-specific Mutagenesis of the Human Fibroblast Interferon Gene", Proc. Natl. Acad. Sci. USA, 81, pp. 5662–66 (1984); and U.S. Pat. No. 4,588,585.

Alternatively, the nucleotide sequence is prepared by chemical synthesis, e.g. by using an oligonucleotide synthesizer, wherein oligonucleotides are designed based on the amino acid sequence of the desired polypeptide variant, and preferably selecting those codons that are favored in the host cell in which the recombinant polypeptide variant will be produced. For example, several small oligonucleotides coding for portions of the desired polypeptide variant may be synthesized and assembled by PCR, ligation or ligation chain reaction (LCR). The individual oligonucleotides typically contain 5' or 3' overhangs for complementary assembly.

Once assembled (by synthesis, site-directed mutagenesis or another method), the nucleotide sequence encoding the polypeptide variant is inserted into a recombinant vector and operably linked to control sequences necessary for expression of the IFNG polypeptide variant in the desired transformed host cell.

It should of course be understood that not all vectors and expression control sequences function equally well to express the nucleotide sequence encoding an IFNG polypeptide variant described herein. Neither will all hosts function equally well with the same expression system. However, one of skill in the art may make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequence encoding the polypeptide variant, particularly as regards potential secondary structures. Hosts should be selected by consideration of their compatibility with the chosen vector, the toxicity of the product coded for by the nucleotide sequence, their secretion characteristics, their ability to fold the polypeptide correctly, their fermentation or culture requirements, and the ease of purification of the products coded for by the nucleotide sequence.

The recombinant vector may be an autonomously replicating vector, i.e. a vector, which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector, in which the nucleotide sequence encoding the IFNG polypeptide variant is operably linked to additional segments required for transcription of the nucleotide sequence. The vector is typically derived from plasmid or viral DNA. A number of suitable expression vectors for expression in the host cells mentioned herein are commercially available or described in the literature. Useful expression vectors for eukaryotic hosts, include, for example, vectors comprising expression control sequences from SV40, bovine papilloma virus, adenovirus and cytomegalovirus. Specific vectors are, e.g., pcDNA3.1 (+)\Hyg (Invitrogen, Carlsbad, Calif., USA) and pCI-neo (Stratagene, La Jola, Calif., USA). Useful expression vectors for bacterial hosts include known bacterial plasmids, such as plasmids from *E. coli*, including pBR322, pET3a and pET12a (both from Novagen Inc., Wis., USA), wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2$\mu$ plasmid and derivatives thereof, the POT1 vector (U.S. Pat. No. 4,931,373), the pJSO37 vector described in (Okkels, Ann. New York Acad. Sci. 782, 202–207, 1996) and pPICZ A, B or C (Invitrogen). Useful vectors for insect cells include pVL941, pBG311 (Cate et al., "Isolation of the Bovine and Human Genes for Mullerian Inhibiting Substance And Expression of the Human Gene In Animal Cells", Cell, 45, pp. 685–98 (1986), pBluebac 4.5 and pMelbac (both available from Invitrogen).

Other vectors for use in this invention include those that allow the nucleotide sequence encoding the IFNG polypeptide variant to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304–19 (1982)) and glutamine synthetase ("GS") amplification (see, e.g., U.S. Pat. No. 5,122,464 and EP 338,841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2$\mu$ replication genes REP 1–3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130), or one which confers resistance to a drug, e.g. ampicillin, kanamycin, tetracyclin, chloramphenicol, neomycin, hygromycin or methotrexate. For filamentous fungi, selectable markers include amdS, pyrG, arcB, niaD, sC.

The term "control sequences" is defined herein to include all components, which are necessary or advantageous for the expression of the IFNG polypeptide variant. Each control sequence may be native or foreign to the nucleic acid sequence encoding the polypeptide variant. Such control sequences include, but are not limited to, a leader, polyadenylation sequence, propeptide sequence, promoter, enhancer or upstream activating sequence, signal peptide sequence, and transcription terminator. At a minimum, the control sequences include a promoter.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g. the adenovirus 2 major late promoter, the MT-1 (metallothionein gene) promoter, the human cytomegalovirus immediate-early gene promoter (CMV), the human elongation factor 1$\alpha$ (EF-1$\alpha$) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, M. *J Mol Biol* Aug. 20, 1987;196(4):947–50).

In order to improve expression in mammalian cells a synthetic intron may be inserted in the 5' untranslated region of the nucleotide sequence encoding the IFNG polypeptide variant. An example of a synthetic intron is the synthetic intron from the plasmid pCI-Neo (available from Promega Corporation, Wis., USA).

Examples of suitable control sequences for directing transcription in insect cells include the polyhedrin promoter, the P10 promoter, the *Autographa californica* polyhedrosis virus basic protein promoter, the baculovirus immediate early gene 1 promoter and the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulans* glucoamylase, *A. nidulans* acetamidase, *Rhizomucor miehei* aspartic proteinase or lipase, the TPI1 terminator and the ADH3 terminator.

Examples of suitable control sequences for use in bacterial host cells include promoters of the lac system, the trp system, the TAC or TRC system and the major promoter regions of phage lambda.

The nucleotide sequence of the invention, whether prepared by site-directed mutagenesis, synthesis or other methods, may or may not also include a nucleotide sequence that encode a signal peptide. The signal peptide is present when the polypeptide is to be secreted from the cells in which it is expressed. Such signal peptide, if present, should be one recognized by the cell chosen for expression of the polypeptide variant. The signal peptide may be homologous (e.g. be that normally associated with huIFNG) or heterologous (i.e. originating from another source than huIFNG) to the polypeptide or may be homologous or heterologous to the host cell, i.e. be a signal peptide normally expressed from the host cell or one which is not normally expressed from the host cell. Accordingly, the signal peptide may be prokaryotic, e.g. derived from a bacterium such as *E. coli*, or eukaryotic, e.g. derived from a mammalian, or insect or yeast cell.

The presence or absence of a signal peptide will, e.g., depend on the expression host cell used for the production of the polypeptide variant, the protein to be expressed (whether it is an intracellular or intracellular protein) and whether it is desirable to obtain secretion. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in insect cells, the signal peptide may conveniently be derived from an insect gene (cf. WO 90/05783), such as the lepidopteran *Manduca sexta* adipokinetic hormone precursor, (cf. U.S. Pat. No. 5,023,328), the honeybee melittin (Invitrogen), ecdysteroid UDPglucosyltransferase (egt) (Murphy et al., Protein Expression and Purification 4, 349–357 (1993) or human pancreatic lipase (hpl) (Methods in Enzymology 284, pp. 262–272, 1997).

A preferred signal peptide for use in mammalian cells is that of huIFNG or the murine Ig kappa light chain signal peptide (Coloma, M (1992) J. Imm. Methods 152:89–104). For use in yeast cells suitable signal peptides have been found to be the α-factor signal peptide from *S. cereviciae*. (cf. U.S. Pat. No. 4,870,008), the signal peptide of mouse salivary amylase (cf. O. Hagenbuchle et al., Nature 289, 1981, pp. 643–646), a modified carboxypeptidase signal peptide (cf. L. A. Valls et al., Cell 48, 1987, pp. 887–897), the yeast BAR1 signal peptide (cf. WO 87/02670), and the yeast aspartic protease 3 (YAP3) signal peptide (cf. M. Egel-Mitani et al., Yeast 6, 1990, pp. 127–137).

Any suitable host may be used to produce the IFNG polypeptide variant, including bacteria, fungi (including yeasts), plant, insect, mammal, or other appropriate animal cells or cell lines, as well as transgenic animals or plants. Examples of bacterial host cells include grampositive bacteria such as strains of *Bacillus*, e.g. *B. brevis* or *B. subtilis*, *Pseudomonas* or *Streptomyces*, or gramnegative bacteria, such as strains of *E. coli* . The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizen, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

Examples of suitable filamentous fungal host cells include strains of *Aspergillus*, e.g. *A. oryzae*, *A. niger*, or *A. nidulans*, *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Examples of suitable yeast host cells include strains of *Saccharomyces*, e.g. *S. cerevisiae, Schizosaccharomyces, Kluyveromyces, Pichia,* such as *P. pastoris* or *P. methanolica, Hansenula,* such as *H. Polymorpha* or *Yarrowia*. Methods for transforming yeast cells with heterologous DNA and producing heterologous polypeptides therefrom are disclosed by Clontech Laboratories, Inc, Palo Alto, Calif., USA (in the product protocol for the Yeastmaker™ Yeast Tranformation System Kit), and by Reeves et al., FEMS Microbiology Letters 99 (1992) 193–198, Manivasakam and Schiestl, Nucleic Acids Research, 1993, Vol. 21, No. 18, pp. 4414–4415 and Ganeva et al., FEMS Microbiology Letters 121 (1994) 159–164.

Examples of suitable insect host cells include a *Lepidoptora* cell line, such as *Spodoptera frugiperda* (Sf9 or Sf21) or *Trichoplusioa ni* cells (High Five) (U.S. Pat. No. 5,077, 214). Transformation of insect cells and production of heterologous polypeptides therein may be performed as described by Invitrogen.

Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. Additional suitable cell lines are known in the art and available from public depositories such as the American Type Culture Collection, Rockville, Md. Also, the mammalian cell, such as a CHO cell, may be modified to express sialyltransferase, e.g. 1,6-sialyltransferase, e.g. as described in U.S. Pat. No. 5,047,335, in order to provide improved glycosylation of the IFNG polypeptide variant. As far as the production of huIFNG-132, [S99T]huIFNG-132 and variants thereof are concerned, it is preferred to produce these fragments in CHO cells, in particular CHO-K1 cells, e.g. in a serum-free media.

Methods for introducing exogenous DNA into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamin 2000. These methods are well known in the art and e.g. described by Ausbel et al. (eds.), 1996, Current Protocols in Molecular Biology, John Wiley & Sons, New York, USA. The cultivation of mammalian cells are conducted according to established methods, e.g. as disclosed in (Animal Cell Biotechnology, Methods and Protocols, Edited by Nigel Jenkins, 1999, Human Press Inc, Totowa, N.J., USA and Harrison Mass. and Rae I F, General Techniques of Cell Culture, Cambridge University Press 1997).

In order to produce a glycosylated polypeptide a eukaryotic host cell, e.g. of the type mentioned above, is used.

In the production methods of the present invention, the cells are cultivated in a nutrient medium suitable for production of the polypeptide variant using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide variant is secreted into the nutrient medium, the polypeptide variant can be recovered directly from the medium. If the polypeptide variant is not secreted, it can be recovered from cell lysates. In an interesting embodiment of the invention, the cells are cultivated in a serum-free medium.

The resulting polypeptide variant may be recovered by methods known in the art. For example, the polypeptide variant may be recovered from the nutrient medium by conventional procedures including, but not limited to, centrifugation, filtration, extraction, spray drying, evaporation, or precipitation.

The polypeptide variants may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), HPLC, or extraction (see, e.g., *Protein Purification,* J.-C. Janson and Lars Ryden, editors, VCH Publishers, New York, 1989). Specific methods for purifying polypeptides exhibiting IFNG activity are disclosed in EP 0 110 044 and unexamined Japanese patent application No. 186995/84.

The activity of the IFNG polypeptide variant can be assayed by any suitable method known in the art. Such assays include antibody neutralization of antiviral activity, induction of protein kinase, oligoadenylate 2,5-A synthetase or phosphodiesterase activities, as described in EP 0 041 313 B1. Such assays also include immunomodulatory assays (see, e.g., U.S. Pat. No. 4,753,795), growth inhibition assays, and measurement of binding to cells that express interferon receptors. Specific assays are described in the Materials and Methods section herein.

Pharmaceutical Compositions and Uses Thereof

Furthermore, the present invention relates to improved methods of treating or preventing, in particular, inflammatory diseases, e.g. interstitial lung diseases, such as idiopathic pulmonary fibrosis, but also granulomatous diseases; cancer, in particular ovarian cancer; infections such as pulmonary a typical mycobacterial infections; bone disorders (e.g. a bone metabolism disorder so as malignant osteopetrosis); autoimmune diseases such as rheumatoid arthritis; as well as other diseases such as multiresistent tuberculosis; cryptococcal meningitis; cystic fibrosis and liver fibrosis, in particular liver fibrosis secondary to hepatitis C, said method comprising administering to a mammal, in particular a human being, in need thereof an effective amount of a polypeptide variant of the invention or a composition of the invention; the key advantages being less frequent and/or less intrusive administration of more efficient therapy, and optionally a lower risk of immune reactions with the therapeutically active compound(s).

The molecule of the invention is preferably administered in a composition including a pharmaceutically acceptable carrier or excipient. "Pharmaceutically acceptable" means a carrier or excipient that does not cause any untoward effects in patients to whom it is administered. Such pharmaceutically acceptable carriers and excipients are well known in the art (Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

The molecules of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

The variant of the invention is administered at a dose approximately paralleling that employed in therapy with known commercial preparations of IFNG such as ACTIMMUNE® IFNG or as specified in EP 0 795 332. The exact dose to be administered depends on the circumstances. Normally, the dose should be capable of preventing or lessening the severity or spread of the condition or indication being treated. It will be apparent to those of skill in the art that an effective amount of variant or composition of the invention depends, inter alia, upon the disease, the dose, the administration schedule, whether the polypeptide variant or composition is administered alone or in conjunction with other therapeutic agents, the serum half-life of the compositions, and the general health of the patient.

The present invention also relates to an IFNG polypeptide variant according to the present invention, or a pharmaceutical composition according to the present invention, for use as a medicament.

Furthermore, the invention also relates to the use of i) an IFNG variant according to the present invention, or ii) a pharmaceutical composition of the invention, for the manufacture of a medicament, a pharmaceutical composition or a kit-of-parts for the treatment of diseases selected from the group consisting of inflammatory diseases, such as interstitial lung diseases, in particular idiopathic pulmonary fibrosis; cancer, in particular ovarian cancer; infections, such as pulmonary a typical mycobacterial infections; bone disorders (e.g. a bone metabolism disorder so as malignant osteopetrosis); granulomatous diseases; autoimmune diseases such as rheumatoid arthritis; multiresistent tuberculosis; cryptococcal meningitis; cystic fibrosis and liver fibrosis, in particular liver fibrosis secondary to hepatitis C. Most preferably the disease is an interstitial lung disease, in particular idiopathic pulmonary fibrosis.

Also disclosed are improved means of delivering the molecules or preparations, optionally additionally comprising glucocorticoids.

The preferred dosing is 1–4, more preferably 2–3, micrograms/kg patient weight of the polypeptide component per dose. The preferred dosing is 100–350, more preferably 100–150 micrograms glucocorticoid/kg patient weight per dose.

The invention also relates to a kit of parts suitable for the treatment of interstitial lung diseases comprising a first pharmaceutical composition comprising the active components i) or ii) mentioned above and a second pharmaceutical composition comprising at least one glucocorticoid, each optionally together with a pharmaceutically acceptable carrier and/or excipient.

The variant of the invention can be formulated into pharmaceutical compositions by well-known methods. Suitable formulations are described by Remington's Pharmaceutical Sciences by E. W. Martin and U.S. Pat. No. 5,183, 746.

The pharmaceutical composition may be formulated in a variety of forms, including liquid, gel, lyophilized, powder, compressed solid, or any other suitable form. The preferred form will depend upon the particular indication being treated and will be apparent to one of skill in the art.

The pharmaceutical composition may be administered orally, subcutaneously, intravenously, intracerebrally, intranasally, transdermally, intraperitoneally, intramuscularly, intrapulmonary, vaginally, rectally, intraocularly, or in any other acceptable manner, e.g. using PowderJect or ProLease technology. The formulations can be administered continuously by infusion, although bolus injection is acceptable, using techniques well known in the art, such as pumps or implantation. In some instances the formulations may be directly applied as a solution or spray. The preferred mode of administration will depend upon the particular indication being treated and will be apparent to one of skill in the art.

The pharmaceutical composition of the invention may be administered in conjunction with other therapeutic agents. These agents may be incorporated as part of the same pharmaceutical composition or may be administered separately from the polypeptide variant of the invention, either concurrently or in accordance with any other acceptable treatment schedule. In addition, the polypeptide variant or pharmaceutical composition of the invention may be used as an adjunct to other therapies. In particular, combinations with glucocorticoids as described in EP 0 795 332 are considered.

In a further aspect the invention relates to a method of treating a mammal having circulating antibodies against huIFNG or rhuIFNG, which method comprises administering an IFNG variant which has the bioactivity of IFNG and which does not react with said antibodies. The compound is preferably a variant as described herein and the mammal is preferably a human being. The mammals to be treated may suffer from any of the diseases listed above for which IFNG is a useful treatment. Furthermore, the invention relates to a method of making a pharmaceutical product for use in treatment of mammals having circulating antibodies against huIFNG or rhuIFNG, wherein an IFNG variant which has the bioactivity of IFNG and which does not react with such is formulated into an injectable or otherwise suitable formulation. The term "circulating antibodies" is intended to indicate autoantibodies formed in a mammal in response to having been treated with any of the commercially available IFNG preparations.

Also contemplated is use of a nucleotide sequence encoding an IFNG polypeptide variant of the invention in gene therapy applications. In particular, it may be of interest to use a nucleotide sequence encoding an IFNG polypeptide variant described in the section above entitled "IFNG variants of the invention wherein the non-polypeptide moiety is a sugar moiety". The glycosylation of the polypeptide variant is thus achieved during the course of the gene therapy, i.e. after expression of the nucleotide sequence in the human body.

Gene therapy applications contemplated include treatment of those diseases in which the polypeptide variant is expected to provide an effective therapy.

Local delivery of IFNG variant using gene therapy may provide the therapeutic agent to the target area while avoiding potential toxicity problems associated with non-specific administration.

Both in vitro and in vivo gene therapy methodologies are contemplated.

Several methods for transferring potentially therapeutic genes to defined cell populations are known. For further reference see, e.g., Mulligan, "The Basic Science Of Gene Therapy", Science, 260, pp. 926–31 (1993). These methods include:

Direct gene transfer, e.g., as disclosed by Wolff et al., "Direct Gene transfer Into Mouse Muscle In vivo", Science 247, pp. 1465–68 (1990);

Liposome-mediated DNA transfer, e.g., as disclosed by Caplen et al., "Liposome-mediated CFTR Gene Transfer to the Nasal Epithelium Of Patients With Cystic Fibrosis" Nature Med., 3, pp. 39–46 (1995); Crystal, "The Gene As A Drug", Nature Med., 1, pp.- 15-17 (1995); Gao and Huang, "A Novel Cationic Liposome Reagent For Efficient Transfection of Mammalian Cells", Biochem. Biophys Res. Comm., 179, pp. 280–85 (1991);

Retrovirus-mediated DNA transfer, e.g., as disclosed by Kay et al., "In vivo Gene Therapy of Hemophilia B: Sustained Partial Correction In Factor IX-Deficient Dogs", Science, 262, pp. 117–19 (1993); Anderson, "Human Gene Therapy", Science, 256, pp.808–13(1992);

DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses as Vectors for Gene Therapy", Gene Therapy, 1, pp. 367–84 (1994); U.S. Pat. No. 4,797,368, and 5,139,941.

Parenterals

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide variant having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives may be added to retard microbial growth, and are typically added in amounts of about 0.2%–1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers may be added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients, which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), PLURONIC® polyols, polyoxyethylene sorbitan monoethers TWEEN®-20, TWEEN®-80, etc.).

Additional miscellaneous excipients include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

Parenteral formulations to be used for in vivo administration must be sterile. This is readily accomplished, for example, by filtration through sterile filtration membranes.

In a preferred embodiment of the invention said pharmaceutical composition comprises the i) IFNG variant of the invention, ii) a buffering agent, in particular a salt of an organic acid, capable of maintaining the pH between 5.0–6.5, iii) a stabilizer, in particular an organic sugar or sugar alcohol, iv) a non-ionic surfactant, and v) sterile water. More particularly, the buffering agent is selected from the group consisting of acetate, succinate and citrate, the stabilizer is mannitol or sorbitol, the non-ionic surfactant is TWEEN®-20, or TWEEN®-80 polyoxyethylene sorbitan monoether. Preferably, the pharmaceutical composition does not include any preservatives.

In a highly preferred embodiment of the invention, the pharmaceutical composition comprises an sulfoalkyl ether cyclodextrin derivative, such as any of the derivatives described in U.S. Pat. Nos. 5,874,418, 5,376,645 and 5,134,127, the contents of which are incorporated herein by reference. In one embodiment of the invention the sulfoalkyl ether cyclodextrin is a compound of the Formula (I):

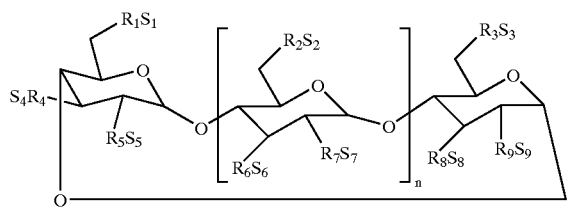

wherein
n is 4, 5 or 6,
$R_1$, $R_2$, $R_3$, $R_4$, $R_5$, $R_6$, $R_7$, $R_8$, and $R_9$ are each, independently, —O— or a —O—$(C_2-C_6$ alkylene$)$-$SO_3$— group, wherein at least one of $R_1$ and $R_2$ is independently a —O—$(C_2-C_6$ alkylene$)$-$SO_3$-group, and
$S_1$, $S_2$, $S_3$, $S_4$, $S_5$, $S_6$, $S_7$, $S_8$, and $S_9$ are each, independently, a pharmaceutically acceptable cation.

In a further embodiment n is 5. In a still further embodiment n is 6.

In a further embodiment at least one of $R_1$ and $R_2$ is —O—$(CH_2)_m$—$SO_3$—, and m is 2, 3, 4, 5 or 6. In a further embodiment $R_1$ and $R_2$ is independently selected from —$OCH_2CH_2CH_2SO_3$— or —$OCH_2CH_2CH_2CH_2SO_3$—.

In a further embodiment at least one of $R_4$, $R_6$, and $R_8$, is independently, —O—$(C_2-C_6$ alkylene$)$-$SO_3$—; and $R_5$, $R_7$, and $R_9$ are all —O—.

In a further embodiment $S_1$, $S_2$, $S_3$, $S_4$, $S_5$, $S_6$, $S_7$, $S_8$, and $S_9$ are each, independently, a pharmaceutically acceptable cation selected from $H^+$, alkali metals (e.g. $Li^+$, $Na^+$, $K^+$), alkaline earth metals (e.g., $Ca^{+2}$, $Mg^{+2}$), ammonium ions and amine cations such as the cations of $(C_1-C_6)$ alkylamines, piperidine, pyrazine, $(C_1-C_6)$ alkanolamine and $(C_4-C_8)$cycloalkanolamine.

In a further embodiment $S_1$, $S_2$, $S_3$, $S_4$, $S_5$, $S_6$, $S_7$, $S_8$, and $S_9$ are independently selected from alkaline metal cation, alkaline earth metal cation, quaternary ammonium cation, tertiary ammonium cation, and secondary ammonium cation.

In a further embodiment at least one of $R_4$, $R_6$, and $R_8$, is independently, —O—$(C_2-C_6$ alkylene$)$-$SO_3$—; and $R_5$, $R_7$, and $R_9$ are all —O—.

The terms "alkylene" and "alkyl," as used herein (e.g., in the —O—$(C_2-C_6$-alkylene$)SO_3$— group or in the alkylamines), include linear, cyclic, and branched, saturated and unsaturated (i.e., containing a double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

The presently preferred sulfoalkyl ether cyclodextrin derivative is a salt of beta cyclodextrin sulfobutyl ether (in particular the sodium salt thereof also termed SBE7-β-CD which is available as CAPTISOL®) (Cydex, Overland Park, Kans. 66213, US).

Sustained Release Preparations

Suitable examples of sustained-release preparations include semi-permeable matrices of solid hydrophobic polymers containing the variant, the matrices having a suitable form such as a film or microcapsules. Examples of sustained-release matrices include polyesters, hydrogels (for example, poly(2-hydroxyethyl-methacrylate) or poly (vinylalcohol)), polylactides, copolymers of L-glutamic acid and ethyl-L-glutamate, non-degradable ethylene-vinyl acetate, degradable lactic acid-glycolic acid copolymers such as the PROLEASE® injectable sustained-release technology or LUPRON DEPOT® injectable microspheres composed of lactic acid-glycolic acid copolymer and leuprolide acetate, and poly-D-(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S——S bond formation through thio-disulfide interchange, stabilization may be achieved by modifying sulfhydryl residues, lyophilizing from acidic solutions, controlling moisture content, using appropriate additives, and developing specific polymer matrix compositions.

Oral Administration

For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The variants may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilization and/or may contain conventional adjuvants such as preservatives, stabilizers, wetting agents, emulsifiers, buffers, fillers, etc., e.g. as disclosed elsewhere herein.

Liquid dosage forms for oral administration may include pharmaceutically acceptable emulsions, solutions, suspensions, syrups and elixirs containing inert diluents commonly used in the art, such as water. Such compositions may also comprise adjuvants such as wetting agents, sweeteners, flavoring agents and perfuming agents.

Topical Administration

Formulations suitable for topical administration include liquid or semi-liquid preparations suitable for penetration through the skin (e.g., liniments, lotions, ointments, creams, or pastes) and drops suitable for administration to the eye, ear, or nose.

Pulmonary Delivery

Formulations suitable for use with a nebulizer, either jet or ultrasonic, will typically comprise the polypeptide variant dissolved in water at a concentration of, e.g., about 0.01 to 25 mg of variant per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer will have a composition and molarity suitable to adjust the solution to a pH in the range of 3 to 9. Generally, buffer molarities of from 1 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in WO 94/20069, U.S. Pat. Nos. 5,915,378, 5,960,792, 5,957,124, 5,934,272, 5,915,378, 5,855,564, 5,826,570 and 5,522,385 which are hereby incorporated by reference.

Formulations for use with a metered dose inhaler device will generally comprise a finely divided powder. This powder may be produced by lyophilizing and then milling a liquid variant formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the variant present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. This mixture is then loaded into the delivery device. An example of a commercially available metered dose inhaler suitable for use in the present invention is the VENTOLIN™ metered dose inhaler, manufactured by Glaxo Inc., Research Triangle Park, N.C.

Formulations for powder inhalers will comprise a finely divided dry powder containing variant and may also include a bulking agent, such as lactose, sorbitol, sucrose, or mannitol in amounts which facilitate dispersal of the powder from the device, e.g., 50% to 90% by weight of the formulation. The particles of the powder shall have aerodynamic properties in the lung corresponding to particles with a density of about 1 g/cm$^2$ having a median diameter less than 10 micrometers, preferably between 0.5 and 5 micrometers, most preferably of between 1.5 and 3.5 micrometers. An example of a powder inhaler suitable for use in accordance with the teachings herein is the SPINHALER™ powder inhaler, manufactured by Fisons Corp., Bedford, Mass.

The powders for these devices may be generated and/or delivered by methods disclosed in U.S. Pat. Nos. 5,997,848, 5,993,783, 5,985,248, 5,976574, 5,922,354, 5,785,049 and 5,654,007.

Mechanical devices designed for pulmonary delivery of therapeutic products, include but are not limited to nebulizers, metered dose inhalers, and powder inhalers, all of which are familiar to those of skill in the art. Specific examples of commercially available devices suitable for the practice of this invention are the ULTRAVENT™ nebulizer, manufactured by Mallinckrodt, Inc., St. Louis, Mo.; the ACORN™ II nebulizer, manufactured by Marquest Medical Products, Englewood, Colo.; the VENTOLIN™ metered dose inhaler, manufactured by Glaxo Inc., Research Triangle Park, N.C.; the SPINHALER™ powder inhaler, manufactured by Fisons Corp., Bedford, Mass.; the STANDING CLOUD™ device of Inhale Therapeutic Systems, Inc., San Carlos, Calif.; the AIR™ inhaler manufactured by Alkermes, Cambridge, Mass.; and the AERX™ pulmonary drug delivery system manufactured by Aradigm Corporation, Hayward, Calif.

The invention is further described in the following examples. The examples should not, in any manner, be understood as limiting the generality of the present specification and claims.

Materials and Methods

Materials

CHO-K1 cells (available from American Type Culture Collection (ATCC #CCL-61)).

HeLa cells (available from American Type Culture Collection (ATCC #CCL-2)).

ISRE-Luc was obtained from Stratagene, La Jolla USA.

pCDNA 3.1/hygro was obtained from Invitrogen, Carlsbad USA.

Restricion enzymes and polymerases were obtained from New England Biolabs Inc., Beverly, USA.

DMEM medium: Dulbecco's Modified Eagle Media (DMEM), 10% fetal bovine serum and Hygromycin B were obtained from Life Technologies A/S, Copenhagen, Denmark.

LucLite substrate was obtained from Packard Bioscience, Groningen, The Netherlands.

TopCount luminometer was obtained from Packard Bioscience, Groningen, The Netherlands.

Biotinylated polyclonal anti-human IFNG antibody, BAF285, was obtained available from R&D Systems Inc., Minneapolis, USA.

Horse Radish Peroxidase-conjugated streptavidin, P0397, was obtained from DAKO, Copenhagen, Denmark.

TMB blotting reagent was obtained from KEM-EN-TEC, Copenhagen, Denmark.

Methods

Interferon Assay Outline

It has previously been published that IFNG interacts with and activates IFNG receptors on HeLa cells. Consequently, transcription is activated at promoters containing an Interferon Stimulated Response Element (ISRE). It is thus possible to screen for agonists of interferon receptors by use of an ISRE coupled luciferase reporter gene (ISRE-luc) placed in HeLa cells.

Primary Assay

HeLa cells are co-transfected with ISRE-Luc and pcDNA 3.1/hygro and foci (cell clones) are created by selection in DMEM media containing Hygromycin B. Cell clones are screened for luciferase activity in the presence or absence of IFNG. Those clones showing the highest ratio of stimulated to unstimulated luciferase activity are used in further assays.

To screen polypeptide variants, 15,000 cells/well are seeded in 96 well culture plates and incubated overnight in DMEM media. The next day the polypeptide variants as well as a known standard are added to the cells in various concentrations. ACTIMMUNE® IFNG was used as "known standard"; A vial of ACTIMMUNE® IFNG was diluted to 300 IU/ml in DMEM, 5% FBS and stored at −80° C. until use.

The plates are incubated for 6 hours at 37 C in a 5% $CO_2$ air atmosphere LucLite substrate (Packard Bioscience, Groningen, The Netherlands) is subsequently added to each well. Plates are sealed and luminescence measured on a TopCount luminometer (Packard) in SPC (single photon counting) mode.

Each individual plate contains wells incubated with IFNG as a stimulated control and other wells containing normal media as an unstimulated control. The ratio between stimulated and unstimulated luciferase activity serves as an internal standard for both IFNG activity and experiment-to-experiment variation. For each IFNG sample, the amount of units were calculated relative to the ACTIMMUNE® IFNG standard and given as AU.

Determination of Increased Degree of Glycosylation

To determine the various degrees of glycosylation of IFNG variant monomers, a SDS-PAGE gel is run under standard conditions and transferred to a nitrocellulose membrane. Western blotting is done according to standard procedures using a biotinylated polyclonal anti-human IFNG antibody (BAF285 from R & D Systems) as primary antibody and Horse Radish Peroxidase-conjugated streptavidin (P0397from DAKO) as secondary antibody followed by staining with TMB blotting reagent (KEM-EN-TEC, Copenhagen, Denmark). The distribution of IFNG variant monomers having varying degrees of glycosylation is made by visual inspection of the stained membrane.

Determination of $AUC_{sc}$

The $AUC_{sc}$ is determined by one 200 µl bolus subcutaneous administration of equal amount (on an activity basis) of the IFNG polypeptide variant of the invention in rats.

For these experiments, female Sprag-Dawley rats, weighing between 220–260 grams, are used. The IFNG polypeptide is formulated in sodium succinate (720 mg/l), mannitol 40 g/l), polysorbat 20 (100 mg/l) at pH 6.0.

Before subcutaneous administration, one blood sample is drawn in the tail-vein to ensure that no background IFNG activity can be detected. After administration, blood samples are withdrawn from the tail vein after 10 min, 20 min, 40 min, 60 min, 120 min, 240 min, 480 min, 720 min, 1440 min, 1620 min, 1920 min and 2880 min (sometimes also 3600 min). Serum is prepared by letting the blood sample coagulate for 20 min at room temperature followed by centrifugation at 5000 g, 20 min at room temperature. The serum is then isolated and stored at −80° C. until determination of IFNG activity using the "Primary Assay" described above. It should be noted that when the amount of units were determined in serum samples from PK studies in rats, the ACTIMMUNE® IFNG standard was diluted in DMEM, 5% FBS and 5% rat serum.

The amount of units in serum (AU/ml) against time (min) is then plotted and the $AUC_{sc}$ is calculated using the GRAPHPAD PRISM™ 3.01 program.

Similar experiments are performed on huIFNG in its glycosylated form and/or ACTIMMUNE® IFNG in order to assess the increase in $AUC_{sc}$ of the IFNG polypeptide variant of the invention as compared to huIFNG in its glycosylated form and/or ACTIMMUNE® IFNG.

Serum Half-life

The serum half-life is determined by one 200 µl bolus intravenous administration of equal amount (on an activity basis) of the IFNG polypeptide variant of the invention in rats.

For these experiments, female Sprag-Dawley rats, weighing between 220–260 grams, are used. The IFNG polypeptide variant is formulated in sodium succinate (720 mg/l), mannitol 40 g/l), polysorbat 20 (100 mg/l) at pH 6.0.

Before intravenous administration, one blood sample is drawn in the tail-vein to ensure that no background IFNG activity can be detected. After administration in one tail vein, blood samples are withdrawn from the other tail vein after 5 min, 10 min, 20 min, 40 min, 60 min, 120 min, 240 min, 480 min, 720 min, 1440 min, 1620 min, 1920 min and 2880 min. Serum is prepared by letting the blood sample coagulate for 20 min at room temperature followed by centrifugation at 5000 g, 20 min at room temperature. The serum is then isolated and stored at −80° C. until determination of IFNG activity using the "Primary Assay" described above. It should be noted that when the amount of units were determined in serum samples from PK studies in rats, the ACTIMMUNE® IFNG standard was diluted in DMEM, 5% FBS and 5% rat serum.

The amount of units in serum (AU/ml) against time (min) is then plotted and the serum half-life is calculated using the WINNONLIN PRO™ 33 program.

Similar experiments are performed on huIFNG in its glycosylated form, and/or ACTIMMUNE® IFNG in order to assess the increase in serum half-life of the IFNG polypeptide variant of the invention as compared to huIFNG in its glycosylated form and/or ACTIMMUNE® IFNG.

Identification of Surface Exposed Amino Acid Residues

Structures

Experimental 3D structures of huIFNG determined by X-ray crystallography have been reported by: Ealick et.al. Science 252:698–702 (1991) reporting on the C-alpha trace of an IFNG homodimer. Walter et.al. Nature 376:230–235 (1995) reporting on the structure of an IFNG homodimer in complex with two molecules of a soluble form of the IFNG receptor. The coordinates of this structure have never been made publicly available. Thiel et. al. Structure 8:927–936 (2000) reporting on the structure of an IFNG homodimer in complex with two molecules of a soluble form of the IFNG receptor having a third molecule of the receptor in the structure not making interactions with the IFNG homodimer.

Accessible Surface Area (ASA)

The computer program Access (B. Lee and F. M. Richards, J. Mol. Biol. 55: 379–400 (1971)) version 2 (Copyright (c) 1983 Yale University) was used to compute the accessible surface area (ASA) of the individual atoms in the structure. This method typically uses a probe-size of 1.4 Å and defines the Accessible Surface Area (ASA) as the area formed by the centre of the probe. Prior to this calculation all water molecules, hydrogen atoms and other atoms not directly related to the protein are removed from the coordinate set.

Fractional ASA of Side Chain

The fractional ASA of the side chain atoms is computed by division of the sum of the ASA of the atoms in the side chain with a value representing the ASA of the side chain atoms of that residue type in an extended ALA-x-ALA tripeptide. See Hubbard, Campbell & Thornton (1991) J. Mol. Biol.: 220,507–530. For this example the CA atom is regarded as a part of the side chain of Glycine residues but not for the remaining residues. The following table are used as standard 100% ASA for the side chain:

| | |
|---|---|
| Ala | 69.23 Å² |
| Arg | 200.35 Å² |
| Asn | 106.25 Å² |
| Asp | 102.06 Å² |
| Cys | 96.69 Å² |
| Gln | 140.58 Å² |
| Glu | 134.61 Å² |
| Gly | 32.28 Å² |
| His | 147.00 Å² |
| Ile | 137.91 Å² |
| Leu | 140.76 Å² |
| Lys | 162.50 Å² |
| Met | 156.08 Å² |
| Phe | 163.90 Å² |
| Pro | 119.65 Å² |
| Ser | 78.16 Å² |
| Thr | 101.67 Å² |
| Trp | 210.89 Å² |
| Tyr | 176.61 Å² |
| Val | 114.14 Å² |

Residues not detected in the structure are defined as having 100% exposure as they are thought to reside in flexible regions.

Determining Distances between Atoms:

The distance between atoms was determined using molecular graphics software e.g. InsightII v. 98.0, MSI INC.

Determination of Receptor Binding Site:

The receptor-binding site is defined as comprising of all residues having their accessible surface area changed upon receptor binding. This is determined by at least two ASA calculations; one on the isolated ligand(s) in the ligand(s)/receptor(s) complex and one on the complete ligand(s)/receptor(s) complex.

EXAMPLES

Example 1

Determination of Surface-exposed Amino Acid Residues

The X-ray structure used was of an IFNG homo-dimer in complex with two molecules of a soluble form of the IFNG receptor having a third molecule of the IFNG receptor in the structure not making interactions with the IFNG homodimer reported by Thiel et.al. Structure 8:927–936 (2000). The structure consists of the IFNG homodimer wherein the two molecules are labeled A and B. For construction purposes there is an additional methionine placed before the IFNG sequence labeled M0 and the sequence is C-terminally truancuted with ten residues (Q133 being the last residue in the constructed molecules). The M0 is removed from the structure in all the calculations of this example. The structure of the two IFNG monomers has very weak electron density after residue 120 and residues were only modeled until residue T126. Therefore, residues S121–T126 were removed from the structure prior to the calculations in this example. The two receptor fragments labeled C and D make direct interactions with the IFNG homodimer and a third receptor molecule labeled E makes no contact with the IFNG homodimer and are not included in these calculations.

Surface Exposure:

Performing fractional ASA calculations on the homodimer of molecules A and B excluding M0 and S121–T126 in both molecules resulted in the following residues having more than 25% of their side chain exposed to the surface in at least one of the monomers: Q1, D2, P3, K6, E9, N10, K12, K13, Y14, N16, G18, H19, S20, D21, A23, D24, N25, G26, T27, G31, K34, N35, K37, E38, E39, S40, K55, K58, N59, K61, D62, D63, Q64, S65, Q67, K68, E71, T72, K74, E75, N78, V79, K80, N83, S84, N85, K86, K87, D90, E93, K94, N97, S99, T101, D102, L103, N104, H111, Q115, A118 and E119.

The following residues had more than 50% of their side chain exposed to the surface in at least one of the monomers: Q1, D2, P3, K6, E9, N10, K13, N16, G18, H19, S20, D21, A23, D24, N25, G26, T27, G31, K34, K37, E38, E39, K55, K58, N59, D62, Q64, S65, K68, E71, E75, N83, S84, K86, K87, K94, N97, S99, T101, D102, L103, N104, Q115, A118, E119.

Performing fractional ASA calculations on the homodimer of molecules A and B excluding M0 and S121–T126 in both molecules and including the receptor molecules C and D resulted in the following residues had more than 25% of their side chain exposed to the surface in at least one of the monomers: Q1, D2, P3, K6, E9, N10, K13, Y14, N16, G18, H19, D21, N25, G26, G31, K34, N35, K37, E38, E39, S40, K55, K58, N59, K61, D62, D63, Q64, S65, Q67, K68, E71, T72, K74, E75, N78, V79, K80, N83, S84, N85, K86, K87, D90, E93, K94, N97, S99, T101, D102, L103, N104, E119.

The following residues had more than 50% of their side chain exposed to the surface in at least one of the monomers: P3, K6, N10, K13, N16, D21, N25, G26, G31, K34, K37, E38, E39, K55, K58, N59, D62, Q64, S65, K68, E71, E75, N83, S84, K86, K87, K94, N97, S99, T101, D102, L103 and N104.

All of the above positions are targets for modification in accordance with the present invention.

Comparing the two lists, results in K12, S20, A23, D24, T27, H111, Q115 and A118 being removed from the more than 25% side chain ASA list upon receptor binding, and Q1, D2, E9, G18, H19, S20, A23, D24, T27, Q115, A118 and E119 being removed from the more than 50% side chain ASA list upon receptor binding.

Residues not determined in the structure are treated as fully surface exposed, i.e. residues S121, P122, A123, A124, K125, T126, G127, K128, R129, K130, R131, S132, Q133, M134, L135, F136, R137, G138, R139, R140, A141, S142, Q143. These residues also constitute separate targets for introduction of attachment groups in accordance with the present invention (or may be viewed as belonging to the group of surface exposed amino acid residues, e.g. having more than 25% or more than 50% exposed side chains).

Example 2

Determination of the Receptor Binding Site

Performing ASA calculations as described above results in the following residues of the IFNG molecule having reduced ASA in at least one of the monomers in the complex as compared to the calculation on the isolated dimer: Q1, D2, Y4, V5, E9, K12, G18, H19, S20, D21, V22, A23, D24, N25, G26, T27, L30, K34, K37, K108, H111, E112, I114, Q115, A118, E119.

Example 3

Design of a Cassette for Expression of IFNG with Optimised Codon Usage

The DNA sequence, GenBank accession number X13274, encompassing a full-length cDNA encoding mature huIFNG with its native signal peptide, was modified in order to facilitate high expression in CHO cells. Codons of the huIFNG nucleotide sequence were modified by making a bias in the codon usage towards the codons frequently used in *homo sapiens*. Subsequently, certain nucleotides in the sequence were substituted with others in order to introduce recognition sites for DNA restriction endonucleases. Primers were designed such that the gene could be synthesised.

The primers were assembled to the synthetic gene by one-step PCR using the PLATINUM™ Pfr DNA polymerase kit (Invitrogen Life Technologies) and standard three-step PCR cycling parameters. The assembled gene was amplified by PCR using the same conditions and the coding sequence is shown in SEQ ID NO:42. The synthesized gene was cloned into pcDNA3.1/hygro (In Vitrogen) between the BamHI and the XbaI sites, resulting in pIGY-22.

pIGY-22 was transfected into CHO K1 cells by use of LIPOFECTAMINE™ 2000 (Invitrogen Life Technologies) as transfection agent. 24 hours later the culture medium was harvested and assayed for IFNG activity and concentration by ELISA (enzyme-linked immunosorbant assay). Using the Primary assay described herein, an activity of $1.4 \times 10^7$ AU/ml was obtained.

Example 4

Site Directed Mutagenesis
Generation of Glycosylation Variants

To introduce mutations in IFNG, oligonucleotides were designed in such a way that PCR-generated changes could be introduced in the expression plasmid (pIGY-22) by classical two-step PCR.

Two vector primers were used together with specific mutation primers: ADJ013: 5'-GATGGCTGGCAACTAGA AG-3' (antisense downstream vector primer) (SEQ ID NO:43) and ADJ014: 5'-TGTACGGTGGGAGGTCTAT-3' (SEQ ID NO:44) (sense upstream vector primer)

The S99T variant was generated by classical two-step PCR, using ADJ013 and ADJ014 as vector primers, ADJ093 (5'-GTTCAGGTCTGTCACGGTGTAATTGGTCAGCTT-3') (SEQ ID NO:45) and ADJ094 (5'-AAGCTGACCAATTACACCGTGACAGACCTGAAC-3') (SEQ ID NO:46) as mutation primers, and pIGY-22 as template. The 447 bp PCR product was subcloned into pcDNA3.1/Hygro (InVitrogen) using BamHI and XbaI, leading to plasmid pIGY-48.

pIGY-48 was transfected into CHO K1 cells by use of LIPOFECTAMINE™ 2000 (Invitrogen Life Technologies) as transfection agent. 24 hours later the culture medium was harvested and assayed for IFNG activity. Using the Primary assay described herein, the following activity was obtained: $5.1 \times 10^6$ AU/ml.

The E38N+S40T+S99T variant was generated by classical two-step PCR, using ADJ013 and ADJ014 as vector primers, ADJ091 (5'-CATGATCTTCCGATCGGT-CTCGTTCTTCCAATT-3') (SEQ ID NO:47) and ADJ092 (5'-AATTGGAAGAACGAGACCGATCGGAAGATCA-TG-3') (SEQ ID NO:48) as mutation primers, and pIGY-48 as template. The 447 bp PCR product was subcloned into pcDNA3.1/Hygro (InVitrogen) using BamHI and XbaI, leading to plasmid pIGY-54.

pIGY-54 was transfected into CHO KI cells by use of LIPOFECTAMINE™ 2000 (Invitrogen Life Technologies) as transfection agent. 24 hours later the culture medium was harvested and assayed for IFNG activity. Using the Primary assay described herein, an activity of $1.3 \times 10^7$ AU/ml was obtained.

Using similar standard techniques as described above, a number of full-length IFNG glycosylation variants were prepared. These variants are compiled in Table 1 below.

Generation of C-terminally Truncated IFNG Variants

C-terminally truncated IFNG variants, containing a stop codon immediately downstream of the codon for Leu135, were generated by one-step PCR using pIGY-22, pIGY-48 and pIGY-54 as templates, followed by subcloning of the PCR products into pcDNA3.1/Hygro (InVitrogen) using BamHI and XbaI. The primers used for construction of these variants were: ADJ014 (see above, upstream) and: 5'-GAGTCTAGATTACAGCATCTGGCTTCTCTT-3' (SEQ ID NO:49) (downstream). The resulting plasmids were termed pIGY-72 (wild-type IFNG truncated after Leu135), pIGY-73 (S99T variant truncated after Leu135) and pIGY-74 (E38N+S40T+S99T truncated after Leu135).

Similarly, a C-terminally truncated IFNG variant, containing a stop codon immediately downstream of the codon for Ser132, was generated by one-step PCR using pIGY-54 as template and CACGGATCCGCCGCCACCATGAAG-TACACAAGCTATATCCTG (SEQ ID NO:50) and TCATCTAGATTAGCTTCTCTTTCTCTTGCCGG (SEQ ID NO:51) as primers. The resulting plasmid was termed pIGY-126 (encoding E38N+S40T+S99T truncated after Ser 132).

Generation of Cysteine-containing IFNG Variants

INFG variants containing cysteine residues were generated using Stratagene's QUIKCHANGE™ XL site-directed mutagenesis kit, according to the manufacturer's specifications. Seven IFNG variants, each containing one introduced cysteine, were generated using pIGY-48 as template: N10C+ S99T, N16C+S99T, E38C+S99T, N59C+S99T, N83C+ S99T, K94C+S99T and S99T+N104C. Similarly, six IFNG variants, each containing one introduced cysteine, were generated using pIGY-54 as a template: N10C+E38N+ S40T+S99T, N16C+E38N+S40T+S99T, E38N+S40T+ N59C+S99T, E38N+S40T+N83C+S99T, E38N+S40T+ K94C+S99T and E38N+S40T+S99T+N104C.

Example 5

PEGylation of Cysteine-containing Variants

All buffers were de-oxidized prior to use. Protein concentrations were estimated by measuring A280.

PEGylation Using the OPSS Coupling Chemistry 7.2 ml of 1.3 mg/ml of the IFNG variant N16C+S99T (full-length) in 5 mM sodium succinate, 4% mannitol, 0.01% TWEEN®-20 polyoxyethylene sorbitan monoether, pH 6.0 was reduced by incubation with 300 µl 0.5 M DTT for 30 minutes at room temperature. The IFNG variant was desalted by running 3 aliquots of 2.5 ml on a NAP25 gel filtration column (Pharmacia) in buffer A (50 mM sodium phosphate, 1 mM EDTA, pH 8.1). Each aliquot eluted in 3.5 ml.

mPEG-OPSS (10 KDa) was dissolved in buffer A to a concentration of 2 mg/ml and added in equal volume to the reduced and desalted IFNG variant and incubated for 60 min with gentle shaking at room temperature.

11 ml of the reaction mixture was concentrated to 1–6 ml using a VIVASPIN™ 20 column (VivaScience) and remaining mPEG was removed by gel filtration using a SEPHACRYL® S-100 column (Pharmacia) equilibrated in buffer A.

The PEGylated IFNG variant was diafiltered into 5 mM sodium succinate, 4% mannitol, pH 6.0 using a VIVASPIN™ 6 column (VivaScience) and TWEEN®-20 polyoxyethylene sorbitan monoether was added to 0.01%. The purified PEGylated IFNG variant had a specific activity of $1.3 \times 10^6$ AU/mg as measured in the Primary Assay described herein (15% of the specific activity of the corresponding non-PEGylated IFNG variant).

PEGylation Using the MAL Coupling Chemistry 1.6 ml of 1.5 mg/ml of the IFNG variant N59C+S99T (full-length) in 5 mM sodium succinate, 4% mannitol, 0.01% TWEEN®-20 polyoxyethylene sorbitan monoether, pH 6.0 was reduced by incubation with 64 μl 0.5 M DTT for 30 minutes at room temperature. The IFNG variant was desalted on a NAP25 gel filtration column (Pharmacia) in buffer A (50 mM sodium phosphate, 1 mM EDTA, pH 8.1). The INFG variant eluted in 3.5 ml.

mPEG-MAL (5 kDa) was dissolved in buffer A to a concentration of 0.5 mg/ml and added in equal volume to reduced and desalted IFNG variant and incubated for 120 minutes with gentle shaking at room temperature.

Ammonium sulphate was added to a concentration of 0.9 M and the PEGylated IFNG variant was applied onto a 1 ml RESOURCE™ phenyl column (Pharmacia) equilibrated in buffer B (20 mM sodium phosphate, 0.9 M ammonium sulphate, pH 6.6). The column was washed with 5 column volumes of buffer B before elution of the bound PEGylated IFNG variant in a linear gradient from 0–50% buffer C (20 mM sodium phosphate, pH 6.6) over 30 column volumes. The PEGylated IFNG variant eluted around 0.6 M ammonium sulphate.

Fractions containing PEGylated IFNG variant were pooled and diafiltered into 5 mM sodium succinate, 4% mannitol, pH 6.0 using a VIVASPIN™ 6 column (VivaScience) and TWEEN®-20 polyoxyethylene sorbitan monoether was added to 0.01%. The purified PEGylated IFNG variant had a specific activity of $2.4 \times 10^6$ AU/mg as measured in the Primary Assay described herein (15% of the specific activity of the corresponding non-PEGylated IFNG variant).

Example 6

Expression of IFNG and IFNG Variants in Mammalian Cells

For transient expression of IFNG, cells were grown to 95% confluency in media (Dulbecco's MEM/Nut.-mix F-12 (Ham) L-glutamine, 15 mM Hepes, pyridoxine-HCl (Life Technologies Cat #31330-038)) containing 1:10 fetal bovine serum (BioWhittaker Cat #02-701F) and 1:100 penicillin and streptomycin (BioWhittaker Cat #17-602E). IFNG-encoding plasmids were transfected into the cells using LIPOFECTAMINE™ 2000 transfecting reagent (Invitrogen Life Technologies) according to the manufacturer's specifications, 24 hrs after transfection, culture media were collected and assayed for IFNG activity. Furthermore, in order to quantify the relative number of glycosylation sites utilized, Western blotting was performed using harvested culture medium.

Stable clones expressing IFNG were generated by transfection of CHO K1 cells with IFNG-encoding plasmids followed by incubation of the cells in media containing 0.36 mg/ml hygromycin. Stably transfected cells were isolated and sub-cloned by limited dilution. Clones producing high levels of IFNG were identified by ELISA.

Example 7

Large-scale Production

Stable cell lines expressing IFNG or variants were grown in Dulbecco's MEM/Nut.-mix F-12 (Ham) L-glutamine, 15 mM Hepes, pyridoxine-HCl (Life Technologies Cat #31330-038), 1:10 fetal bovine serum (BioWhittaker Cat #02-701F), 1:100 penicillin and streptomycin (BioWhittaker Cat #17-602E) in 1700 cm2 roller bottles (Corning, #431200) until confluence. The media was then changed to 300 ml Ultra-CHO™ serum free medium for CHO cell line with L-glutamine (BioWhittaker Cat #12-724Q) with the addition of 1:500 EX-CYTE VLE™ fatty acid growth supplement derived from the lipid fraction of adult bovine sera (Serological Proteins Inc. #81-129) and 1:100 penicillin and streptomycin (BioWhittaker Cat #17-602E). After 48 hours of growth, the media was replaced with fresh UltraCHO™ medium with the same additives. After another 48 hours of growth, the media was replaced with Dulbecco's MEM/Nut.-mix F-12 (Ham) L-glutamine, pyridoxine-HCl (Life Technologies Cat #21041-025) with the addition of 1:100 ITS-A (Gibco/BRL #51300-044), 1:500 EX-CYTE VLE™ fatty acid growth supplement (Serological Proteins Inc. #81-129) and 1:100 penicillin and streptomycin (BioWhittaker Cat #17-602E). Subsequently, every 24 h, culture media were harvested and replaced with 300 ml of fresh serum-free media with the same additives, The collected media were filtered through 0.22 μm filters to remove cells.

Example 8

Purification

The filtrate was microfiltrated (0.22 μm) before ultrafiltration to approximately ⅟15 volume using a Millipore TFF system. On the same system the concentrate was diafiltrated using 10 mM Tris, pH 7.6. Ammonium sulphate was added to a concentration of 1.7 M and after stirring the precipitate was removed by centrifugation at 8000 rpm for 25 minutes in a Sorvall centrifuge using a GS3 rotor.

The supernatant was applied onto a 25 ml Phenyl High Performance (Pharmacia) column previously equilibrated in 10 mM Tris, 1.7 M ammonium sulphate, pH 7.6. After application, the column was washed with 3 column volumes of 10 mM Tris, 1.7 M ammonium sulphate, pH 7.6 and the bound IFNG variant was then eluted in a linear gradient over 10 column volumes to 100% 10 mM Tris, pH 7.6. The flow-through as well as the eluted IFNG variant was fractionated. Fractions enriched in the IFNG variant were pooled and buffer exchanged by diafiltration into 10 mM Tris, pH 9.0, using a VIVAFLOW™ 200 system (VivaScience) with a molecular weight cut-off of 10,000 Da.

The IFNG variant was then applied onto a 18 ml Q-SEPHAROSE® Fast Flow (Pharmacia) column previously equilibrated in 10 mM Tris, pH 9.0. After application the column was washed with 3 column volumes of 10 mM Tris, pH 9.0 before eluting the bound IFNG variant in a gradient from 0–100% 10 mM Tris, 0.5 M NaCl, pH 9.0, over 15 column volumes. The flow-through as well as the eluted IFNG variant was fractionated. Fractions enriched in the IFNG variant were pooled and buffer exchanged into 10 mM sodium phosphate, pH 7.0, by diafiltration using a VIVASPIN™ 20 (VivaScience) column with a molecular weight cut-off of 10,000 Da.

Then, the IFNG variant was applied onto an 8 ml CHT ceramic hydroxyapatite column (Biorad) previously equilibrated in 10 mM sodium phosphate, pH 7.0. After application, the column was washed with 5 column volumes of 10 mM sodium phosphate, pH 7.0, before elution of the bound IFNG variant in a gradient from 0–60% 500 mM sodium phosphate, pH 7.0, over 30 column volumes. The flow-through as well as the eluted IFNG variant was fractionated. Fractions containing the IFNG variant were pooled and buffer exchanged into 5 mM sodium succinate, 4% mannitol, pH 6.0, using a VIVASPIN™ 20 column (VivaScience) and TWEEN®-20 polyoxyethylene sorbitan monoether was subsequently added to a concentration of 0.01%. The IFNG variant was sterile filtered and stored at −80° C.

Alternatively, the IFNG variants may be purified according to the below purification scheme:

The filtrate is microfiltrated (0.22 μm) before ultrafiltration to approximately ⅟15 volume using a Millipore TFF system. On the same system the concentrate is diafiltrated using 10 mM Tris, pH 7.6, after which pH is adjusted to 9.0 and precipitate is removed by microfiltration.

The sample is applied onto a Q-SEPHAROSE® Fast Flow (Pharmacia) column previously equilibrated in 10 mM Tris, pH 9.0. After application, the column is washed with 3 column volumes of 10 mM Tris, pH 9.0 before eluting the bound IFNG variant in a gradient from 0–100% 10 mM Tris, 0.5 M NaCl, pH 9.0 over 15 column volumes. The flow-through as well as the eluted IFNG variant is fractionated. Fractions enriched in the IFNG variant are pooled, and pH is adjusted to 7.6. Ammonium sulphate is added to 1.5 M and after stirring the precipitate is removed by centrifugation.

The IFNG variant is then applied onto a Phenyl SEPHAROSE® High Performance column (Pharmacia) previously equilibrated in 10 mM Tris, 1.5 M ammonium sulphate, pH 7.6. After application, the column is washed with 3 column volumes of 10 mM Tris, 1.5 M ammonium sulphate, pH 7.6, and the bound IFNG variant is then eluted in a linear gradient over 10 column volumes to 100% 10 mM Tris, pH 7.6. The flow-through as well as the eluted IFNG variant is fractionated. Fractions enriched in the INFG variant are pooled and ammonium sulphate is adjusted to 1.7 M.

Then, the IFNG variant is applied onto a Butyl SEPHAROSE® column previously equilibrated in 10 mM sodium phosphate, 1.7 M ammonium sulphate, pH 7.6. After application, the column is washed with 10 mM sodium phosphate, 1.7 M ammonium sulphate, pH 7.6, before eluting the bound IFNG variant in a step using 10 mM sodium phosphate, pH 6.5. The flow-through as well as the eluted IFNG variant is fractionated.

Fractions enriched in the IFNG variant are then pooled and applied onto a hydroxyapatite column previously equilibrated in 10 mM sodium phosphate, pH 6.5. After application the column is washed with 5 column volumes of 10 mM sodium phosphate, pH 6.5, before eluting the bound IFNG variant in a linear gradient from 0–100% 500 mM sodium phosphate, pH 6.5, over 30 column volumes. The flow-through as well as the eluted IFNG variant is fractionated.

Fractions containing the IFNG variant are pooled and, buffer exchanged into a buffer containing 5 mM sodium succinate, 4% mannitol, pH 6.0. TWEEN200-20 polyoxyethylene sorbitan monoether is subsequently added to a concentration of 0.01%. The IFNG variant is sterile filtered and stored at −80° C.

Example 9

Activity of Variants and PEGylated Variants

Using the "primary Assay" described above, the following activity data (after transient transfection) were obtained:

TABLE 1

Activity of variants of full-length and truncated rhuIFNG polypeptides after transient transfection

| Mutations | Activity (AU/ml) | % activity of full-length wt |
|---|---|---|
| Wild-type (full-length) | $1.4 \times 10^7$ | — |
| S99T (full-length) | $5.1 \times 10^6$ | 36% |
| E38N (full-length) | $1.4 \times 10^7$ | 100% |
| E38N + S40T (full-length) | $9.9 \times 10^6$ | 71% |
| E38N + S40T + S99T (full-length) | $1.3 \times 10^7$ | 93% |
| E38N + K61T (full-length) | $1.2 \times 10^7$ | 86% |
| E38N + K61T + S99T (full-length) | $1.4 \times 10^6$ | 10% |
| N10C + S99T (full-length) | $2.5 \times 10^6$ | 18% |
| N16C + S99T (full-length) | $1.1 \times 10^7$ | 79% |

TABLE 1-continued

Activity of variants of full-length and truncated rhuIFNG polypeptides after transient transfection

| Mutations | Activity (AU/ml) | % activity of full-length wt |
|---|---|---|
| E38C + S99T (full-length) | $1.0 \times 10^7$ | 71% |
| S99T + N104C (full-length) | $5.0 \times 10^6$ | 36% |
| N10C + E38N + S40T + S99T (full-length) | $1.5 \times 10^6$ | 11% |
| N16C + E38N + S40T + S99T (full-length) | $3.7 \times 10^6$ | 26% |
| E38N + S40T + N59C + S99T (full-length) | $1.1 \times 10^7$ | 79% |
| E38N + S40T + N83C + S99T (full-length) | $7.2 \times 10^5$ | 5% |
| E38N + S40T + K94C + S99T (full-length) | $9.4 \times 10^5$ | 7% |
| E38N + S40T + S99T + N104C (full-length) | $2.3 \times 10^6$ | 16% |
| Wild-type (truncated after Leu135) | $6.3 \times 10^6$ | 45% |
| S99T (truncated after Leu135) | $3.5 \times 10^6$ | 25% |
| E38N + S40T + S99T (truncated after Leu135) | $4.0 \times 10^6$ | 29% |

Using the "primary Assay" described above, the following specific activity data (after purification) were obtained:

TABLE 2

Activity of variants of full-length rhuIFNG polypeptides after purification

| Mutations | Specific activity (AU/mg) | % activity of full-length wt |
|---|---|---|
| Wild-type (full-length) | $2.1 \times 10^7$ | — |
| S99T (full-length) | $2.2 \times 10^7$ | 105% |
| E38N + S40T + S99T (full-length) | $1.4 \times 10^7$ | 67% |
| N10C + S99T (full-length) | $3.8 \times 10^6$ | 18% |
| N16C + S99T (full-length) | $2.3 \times 10^6$ | 11% |
| N16C + S99T (full-length + 10 kDa mPEG) | $1.3 \times 10^6$ | 6% |
| E38C + S99T (full-length) | $3.4 \times 10^6$ | 16% |
| N59C + S99T (full-length) | $6.3 \times 10^6$ | 30% |
| N59C + S99T (full-length + 5 kDa mPEG) | $2.4 \times 10^6$ | 11% |
| S99T + N104C (full-length) | $3.5 \times 10^6$ | 17% |

The activity of a number of the PEGylated variants were measured by comparing the activity of the PEGylation products by samples which have been subjected to the same PEGylation procedure (see Example 5 above), but without actually adding PEG to the reaction medium. The results are compiled in Table 3 below:

TABLE 3

Activity of PEGylated variants of full-length rhuIFNG polypeptides

| Mutations | Activity relative to non-PEGylated product subjected to "PEGylation procedure" (%) |
|---|---|
| N10C + S99T (full-length + 5 kDa mPEG) | 23 |
| N16C + S99T (full-length + 5 kDa mPEG) | 59 |
| E38C + S99T (full-length + 10 kDa mPEG)[1] | 41 |
| S99T + N104C (full-length + 5 kDa mPEG) | 42 |

[1]ODSS coupling chemistry employed. MAL coupling chemistry employed for all other PEGylated variants It should be emphasized that the activity data shown in Table 1, reflect a combination of specific activity and expression level in CHO-K1 cells. It can therefore be concluded that all variants show a comparable expression level/specific activity to relative to rhuIFNG.

As can be seen in Table 2, all cysteine variants show a decreased specific activity compared to rhuIFNG while variants containing the E38N, S40T and/or S99T mutations retained a specific activity comparable to rhuIFNG. When the cysteine variants were PEGylated with either 5 or 10 kDa a further 2–3 fold drop in specific activity was observed (Table 3). Without being limited to any specific theory, it could be speculated that the decrease in specific activity could be due to decreased receptor binding caused by steric hindrance of the conjugated PEG group.

Example 10

Assessment of Utilization of N-glycosylation Sites

Figure 1:
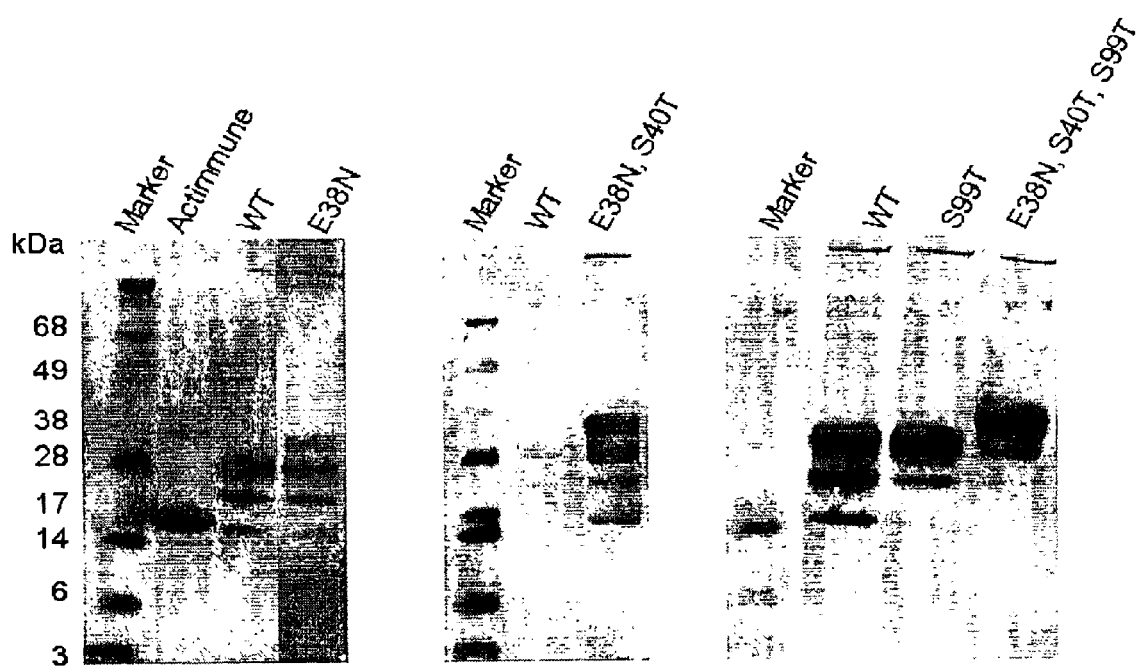
FIG. 1 is a Western blot of optimized glycosylation variants of rhuIFNG. Left side Western blot: Lane 1: standard, Lane 2: ACTIMMUNE® brand human recombinant IFNG-1h that is C-terminally truncated by 4 amino acid residues and that includes one N-terminal Met residue), as disclosed in SEQ ID NO:34), Lane 3: rhuIFNG, Lane 4: [E38N]rhuIFNG. Middle Western blot: Lane 1: standard, Lane 2: rhuIFNG, Lane 3: [E38N+S40T]rhuIFNG. Right side Western blot: Lane 1: standard, Lane 2: rhuIFNG Lane 3: [S99T]rhuIFNG, Lane 4: [E38N+S40T+S99T]rhuIFNG.

In order to quantify the relative number of glycosylation sites utilized, western blotting was performed using harvested culture medium (see FIG. 1). For the wild-type rhuIFNG (full-length), it was estimated that about 50% utilized both glycosylation sites (2N), about 40% utilized one glycosylation site (1N), and about 10% was not glycosylated (0N). These data are in agreement with previously published data by Hooker et al., 1998, J. Interferon and Cytokine Res. 18, 287–295 and Sarenva et al., 1995, Biochem J., 308, 9–14.

As it appears from FIG. 1, the S99T variant (full-length) utilizes its two glycosylation sites significantly more efficiently than the corresponding wild-type. For the S99T variant, it was estimated that about 90% utilized both glycosylation sites (2N), about 7% utilized one glycosylation site (1N), and about 3% was not glycosylated (0N).

Moreover, it is apparent from FIG. 1 that the introduced glycosylation site at position 38 is significantly better utilized for the variant E38N+S40T (full-length) compared to the non-optimised variant E38N (full-length).

These data clearly demonstrate that better utilization of glycosylation sites, independently of whether these sites are naturally occurring or introduced, can be achieved by introducing a threonine residue rather than a serine residue in position +2 relative to the asparagine residue.

Example 11

Pharmacokinetic Studies

The AUC for subcutaneous administration ($AUC_{sc}$) in rats was determined as described hereinbefore for a number of IFNG variants. The results are compiled in Table 4 and in FIGS. 2 and 3.

Figure 3:
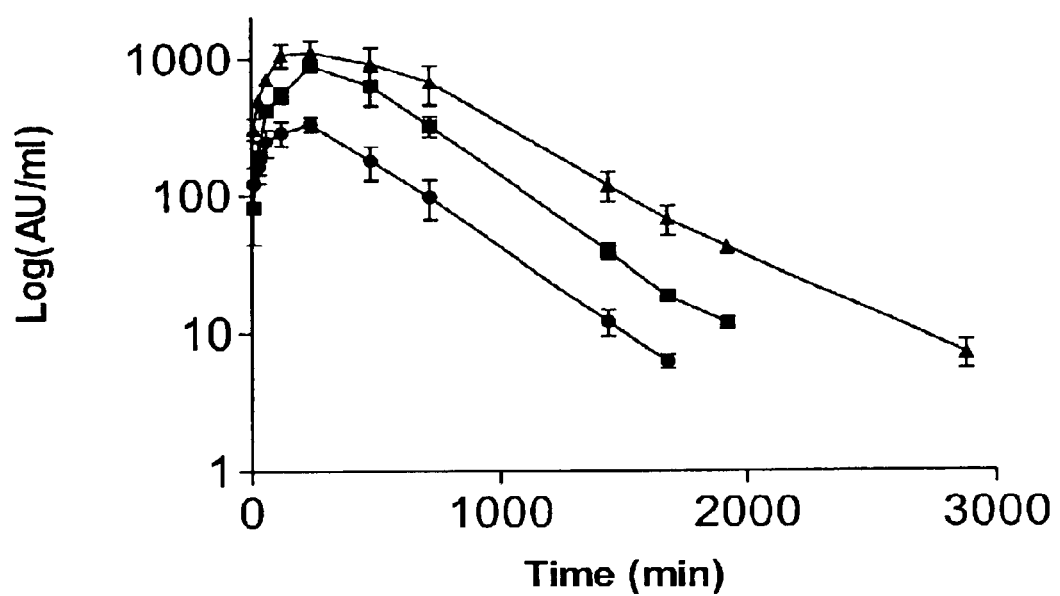
FIG. 3 shows the IFNG activity in serum-time curve after subcutaneous administration in rats. ●: [N16C+S99T] rhuIFNG (5 kDa mPEG attached), ■:[N16C+S99T] rhuIFNG (10 kDa mPEG attached), ▲: [E38N+S40T+S99T]

ID NO:34 from *E. coli*). Referring to FIG. 3, it should be noted that the administered dose of the two PEGylated variants were reduced 2.5 fold compared to the administered dose of the [E38N+S40T+S99T] variant.

Evidently, this opens up the possibility of administering lower doses, thereby obtaining fewer side effects, and/or administering the active principle less frequently than today thereby obtaining an improved patient compliance.

Example 12

Analysis of C-terminal Truncation

The variants [E38N+S40T+S99T]huIFNG, [E38N+S40T+S99T]huIFNG-135 and [E38N+S40T+S99T]huIFNG-132 were constructed to study the C-terminal truncation in more detail. The variants were purified from serum-free media as described in Example 6, except that stabile clones from pooled clones were used instead of selected high-expressing single clones. In general, 2500 to 5000 ml media was used to purify the individual variants. The sterile-filtered media (0.22 μm) were concentrated to approx. 1/15 volume and subsequently diafiltered (to a conductivity <2 mS/cm) using 5 mM sodium phosphate, pH 6.2, on a PALL FILTRON™ tangential flow diafiltration system (Pall Corporation). The concentrated/diafiltered media was filtered (0.22 μm) to clear the sample from any precipitated material prior to further purification. The pH in the filtrate was adjusted to 6.2 before application onto a 2 ml CM-SEPHAROSE® Fast Flow column (Pharmacia) previously equilibrated in 10 mM sodium phosphate, pH 6.2. The column was washed with 10–15 column volumes 10 mM sodium phosphate, pH 6.2, before step-eluting bound variants with 2–3 column volumes of 100 mM sodium phosphate, 500 mM NaCl, pH 7.0. The step-eluted variants were filtered (0.45 μm) before being immunoprecipitated with an IFNG antibody affinity column. The antibody affinity column was prepared according to the manufacture's instructions by coupling 10 mg monoclonal mouse anti-human IFNG antibody (catalog no. MD-2, U-CyTech, Holland) onto approx. 1.3 ml activated CNBr SEPHAROSE® chromatography medium (Pharmacia). The filtered sample from the CM-SEPHAROSE® column was applied onto the antibody affinity column previously equilibrated with phosphate-buffered saline. The column was then washed with 5 column volumes of phosphate buffered saline and the variant was subsequently eluted into a vial already

TABLE 4

Pharmacokinetic data for subtunaceous administration in rats

| Variant | $AUC_{sc}$/dose (min × g)/ml | $\dfrac{AUC_{sc,\,variant}}{AUC_{sc,\,Actimmune\,®}}$ | $\dfrac{AUC_{sc,variant}}{AUC_{sc,full\text{-}length,wt}}$ | $T_{max,sc}$ (min) |
|---|---|---|---|---|
| Actimmune ® | 0.3–0.4 | — | 0.013–0.027 | 43 |
| rhuIFNG (full-length) | 15–24 | 37–80 | — | 362–446 |
| E38N + S40T + S99T[1] | 111–192 | 277–640 | 4.6–13 | 308–374 |
| N16C + S99T[2] | 37 | 92–123 | 1.5–2.5 | 247 |
| N16C + S99T[3] | 114 | 285–380 | 4.8–7.6 | 249 |

Figure 2:
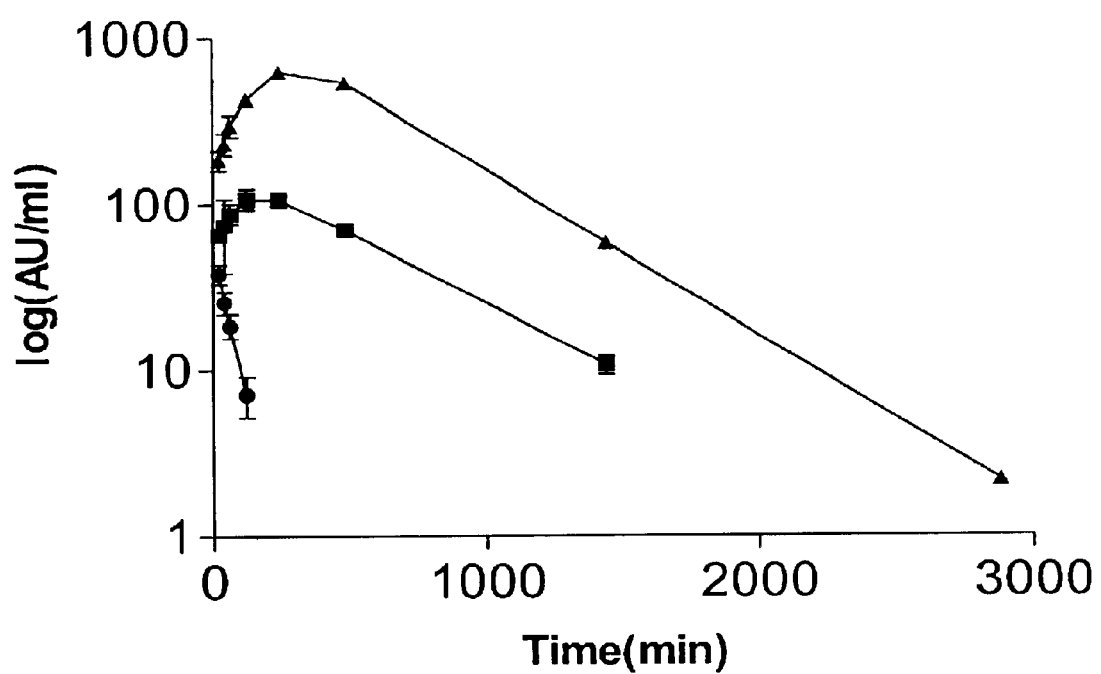
FIG. 2 shows the IFNG activity in serum-time curve after subcutaneous administration in rats. ●:ACTIMMUNE® IFNG, ■:rhuIFNG, ▲:[E38N+S40T+S99T]rhuIFNG. The same dose was administered for all compounds ($1.15 \times 10^7$ AU/kg).

[1]full-length
[2]full-length, 5 kDa mPEG attached to the introduced cysteine residue
[3]full-length, 10 kDa mPEG attached to the introduced cysteine residue Referring to FIGS. 2 and 3 and Table 4, it is evident that the variants (including PEGylated variants) have a significantly higher AUC, when administered subcutaneously, as compared to rhuIFNG and, in particular, when compared to the commercially available ACTIMMUNE® IFNG (SEQ containing 0.15 ml 500 mM sodium phosphate, pH 7.2, using 2 column volumes 100 mM glycine, pH 3.5.

Analysis of C-terminal truncation was done by MALDI-TOF mass spectrometry following enzymatic deglycosylation using the following procedure:

N-linked carbohydrate moieties attached to Asn-residues were removed by treatment of 30 µl of the affinity-purified variant with 1 mU PNGase F (Roche) at 37° C. for 16 h. A 1 µl sample aliquot was mixed with 1 µl matrix solution (saturated α-cyano-4-hydroxy cinnamic acid in 50% acetonitril, 0.1% TFA). Half of the mixture was spotted onto a Thin-Layer of α-cyano-4-hydroxy cinnamic acid on the target plate and air-dried. (The Thin-Layer coating was preformed on the target plate by crystallisation of α-cyano-4-hydroxy cinnamic acid from the Thin-Layer matrix solution (saturated α-cyano-4-hydroxy cinnamic acid in 100% acetone)). The sample spot was washed twice with 1 µl HPLC grade water and air-dried. The sample spot was added 0.2 µl matrix solution and air-dried. Following introduction of the target plate into the mass spectrometer, spectra were recorded at threshold laser power.

MALDI-TOF mass spectrometry was carried out in an Applied Biosystems Voyager-DE Pro mass spectrometer in linear mode using positive ionisation. C-terminal truncation was evaluated by comparing recorded spectra with the expected mass of the purified variant.

Using the above approach, the following IFNG variants were analysed:

[E38N+S40T+S99T]huIFNG (see FIG. 4),
[E38N+S40T+S99T]huIFNG-135 (see FIG. 5), and
[E38N+S40T+S99T]huIFNG-132 (see FIG. 6)

In FIGS. 4–6, the amino acid residues indicated above each peak correspond to the C-terminal amino acid residues of the variants.

In FIG. 4 a significant C-terminal processing is clearly seen for the variant [E38N+S40T+S99T]huIFNG.

In FIG. 5 it can be seen that the genetically truncated variant [E38N+S40T+S99T]huIFNG-135 is still C-terminally processed.

However, it is evident from FIG. 6 that the genetically truncated variant [E38N+S40T+S99T]huIFNG-132 is only C-terminally processed to a very small extent.

What is claimed is:

1. A carboxy-truncated interferon gamma (IFNG) polypeptide variant exhibiting IFNG receptor-binding activity and comprising (i) the amino acid sequence shown in SEQ ID NO: 12; or (ii) an amino acid sequence with 1 to 10 residue modifications relative to the amino acid sequence shown in SEQ ID NO: 12.

2. The variant according to claim 1, wherein said variant is glycosylated.

3. The variant according to claim 1, wherein said variant has an amino acid sequence with one residue modification relative to the amino acid sequence shown in SEQ ID NO: 12.

4. The variant according to claim 1, wherein said variant comprises an amino acid sequence with 1 to 10 residue modifications relative to the amino acid sequence shown in SEQ ID NO: 12.

5. The variant according to claim 4, wherein said 1 to 10 residue modifications comprises at least one introduced and/or at least one removed amino acid residue comprising an attachment group for a non-polypeptide moiety.

6. The variant according to claim 4, wherein said 1 to 10 residue modifications comprises at least one introduced glycosylation site.

7. The variant according to claim 6, wherein said glycosylation site is an N-glycosylation site.

8. The variant according to claim 7, wherein said N-glycosylation site is introduced in a position comprising an amino acid residue having at least 25% of its side chain exposed to the surface.

9. The variant according to claim 8, wherein said N-glycosylation site is introduced in a position comprising an amino acid residue having at least 50% of its side chain exposed to the surface.

10. The variant according to claim 9, wherein said N-glycosylation site is introduced by substitution of an amino acid residue.

11. The variant according to claim 10, wherein said substitution is selected from the group consisting of K12S, K12T, G18S, G18T, E38N, E38N+S40T, K61S, K61T, S65N+Q67S, S65N+Q67T, N85S, N85T, K94N, Q106S and Q106T.

12. The variant according to claim 11, wherein said substitution is selected from the group consisting of K12T, G18T, E38N+S40T, K61T, S65N+Q67T, N85T, K94N and Q106T.

13. The variant according to claim 12, wherein said substitution is E38N+S40T.

14. The variant according to claim 13, wherein said variant further comprises one introduced cysteine residue.

15. The variant according to claim 14, wherein said cysteine residue is introduced in a position comprising an amino acid residue having at least 25% of its side chain exposed to the surface.

16. The variant according to claim 15, wherein said cysteine residue is introduced in a position comprising an amino acid residue having at least 50% of its side chain exposed to the surface.

17. The variant according to claim 16, wherein said cysteine residue is introduced by substitution.

18. The variant according to claim 17, wherein said substitution is selected from the group consisting of N10C, N16C, E38C, N59C, S65C, N83C, K94C, N104C and A124C.

19. The variant according to claim 14, wherein said cysteine residue is covalently attached to a non-polypeptide moiety.

20. The variant according to claim 19, wherein said non-polypeptide moiety is a polymer molecule.

21. The variant according to claim 20, wherein said polymer molecule is a linear or branched polyethylene glycol.

22. The variant according to claim 5, wherein said variant comprises at least one introduced N-glycosylation site and at least one introduced cysteine residue.

23. The variant according to claim 22, wherein said variant comprises substitutions selected from the group consisting of K12T+N16C, K12T+E38C, K12T+N59C, K12T+S65C, K12T+N83C, K12T+K94C, K12T+N104C, K12T+A124C, G18T+N10C, G18T+E38C, G18T+N59C, G18T+S65C, G18T+N83C, G18T+K94C, G18T+N104C, G18T+A124C, G18N+S20T+N10C, G18N+S20T+N16C, G18N+S20T+E38C, G18N+S20T+N59C, G18N+S20T+ S65C, G18N+S20T+N83C, G18N+S20T+K94C, G18N+ S20T+N104C, G18N+S20T+A124C, E38N+S40T+N10C, E38N+S40T+N16C, E38N+S40T+N59C, E38N+S40T+ S65C, E38N+S40T+N83C, E38N+S40T+K94C, E38N+ S40T+N104C, E38N+S40T+A124C, K61T+N10C, K61T+ N16C, K61T+E38C, K61T+S65C, K61T+N83C, K61T+ K94C, K61T+N104C, K61T+A124C, S65N+Q67T+N10C, S65N+Q67T+N 16C, S65N+Q67T+E38C, S65N+Q67T+ S65C, S65N+Q67T+N83C, S65N+Q67T+K94C, S65N+ Q67T+N104C, S65N+Q67T+A124C, N85T+N10C, N85T+ N16C, N85T+E38C, N85T+N59C, N85T+S65C, N85T+ K94C, N85T+N104C, N85T+A124C, K94N+N10C, K94N+N16C, K94N+E38C, K94N+N59C, K94N+S65C, K94N+N83C, K94N+N104C, K94N+A124C, Q106T+ N10C, Q106T+N16C, Q106T+E38C, Q106T+N59C, Q106T+S65C, Q106T+N83C, Q106T+K94C and Q106T+ A124C.

24. The variant according to claim 23, wherein said variant comprises substitutions selected from the group consisting of E38N+S40T+N10C, E38N+S40T+N16C, E38N+S40T+N59C, E38N+S40T+S65C, E38N+S40T+ N83C, E38N+S40T+K94C, E38N+S40T+N104C and E38N+S40T+A124C.

25. The variant according to claim 22, wherein said cysteine residue is covalently attached to a non-polypeptide moiety.

26. The variant according to claim 25, wherein said non-polypeptide moiety is a polymer molecule.

27. The variant according to claim 26, wherein said polymer molecule is a linear or branched polyethylene glycol.

28. A pharmaceutical composition comprising a polypeptide variant as defined in claim 1 or 3 and a pharmaceutically acceptable diluent, carrier or excipient.

29. An S99T interferon gamma (IFNG) polypeptide variant having an amino acid sequence that is the sequence of SEQ ID NO: 12.

30. An S99T interferon gamma (IFNG) polypeptide variant exhibiting IFNG receptor-biding activity and having an amino acid sequence consisting of the sequence of SEQ ID NO: 12 with 1 to 10 residue modifications therein.

31. The S99T interferon gamma (IFNG) polypeptide variant of claim 30, wherein said 1 to 10 modifications comprises at least one introduced and/or at least one removed amino acid residue comprising an attachment group for a non-polypeptide moiety.

32. The variant according to claim 31, wherein said 1 to 10 modifications comprises at least one introduced glycosylation site.

33. The variant according to claim 32, wherein said glycosylation site is an N-glycosylation site.

34. The variant according to claim 33, wherein said N-glycosylation site is introduced in a position comprising an amino acid residue having at least 25% of its side chain exposed to the surface.

35. The variant according to claim 34, wherein said N-glycosylation site is introduced in a position comprising an amino acid residue having at least 50% of its side chain exposed to the surface.

36. The variant according to claim 35, wherein said N-glycosylation site is introduced by substitution of amino acid residues.

37. The variant according to claim 36, wherein said substitution is selected from the group consisting of K12S, K12T, G18S, G18T, E38N, E38N+S40T, K61S, K61T, S65N+Q67S, S65N+Q67T, N85S, N85T, K94N, Q106S and Q106T.

38. The variant according to claim 37, wherein said substitution is selected from the group consisting of K12T, G18T, E38N+S40T, K61T, S65N+Q67T, N85T, K94N and Q106T.

39. The variant according to wherein said claim 38, wherein said substitution is E38N+S40T.

40. The variant according to claim 39, wherein said variant comprises one introduced cysteine residue.

41. The variant according to claim 40, wherein said cysteine residue is introduced in a position comprising an amino acid residue having at least 25% of its side chain exposed to the surface.

42. The variant according to claims 41, wherein said cysteine residue is introduced in a position comprising an amino acid residue having at least 50% of its side chain exposed to the surface.

43. The variant according to claim 42, wherein said cysteine residue is introduced by substitution.

44. The variant according to claim 43, wherein said substitution is selected from the group consisting of N10C, N16C, N59C, S65C, N83C, K94C, N104C and A124C.

45. The variant according to claim 40, wherein said cysteine residue is covalently attached to a non-polypeptide moiety.

46. The variant according to claim 45, wherein said non-polypeptide moiety is a polymer molecule.

47. The variant according to claim 46, wherein said polymer molecule is a linear or branched polyethylene glycol.

48. The variant according to claim 32, wherein said variant comprises at least one introduced N-glycosylation site and at least one introduced cysteine residue.

49. The variant according to claim 48, wherein said variant comprises substitutions selected from the group consisting of K12T+N16C, K12T+E38C, K12T+N59C, K12T+S65C, K12T+N83C, K12T+K94C, K12T+N104C, K12T+A124C, G18T+N10C, G18T+E38C, G18T+N59C, G18T+S65C, G18T+N83C, G18T+K94C, G18T+N104C, G18T+A124C, G18N+S20T+N10C, G18N+S20T+N16C, G18N+S20T+E38C, G18N+S20T+N59C, G18N+S20T+S65C, G18N+S20T+N83C, G18N+S20T+K94C, G18N+S20T+N104C, G18N+S20T+A124C, E38N+S40T+N10C, E38N+S40T+N16C, E38N+S40T+N59C, E38N+S40T+S65C, E38N+S40T+N83C, E38N+S40T+K94C, E38N+

S40T+N104C, E38N+S40T+A124C, K61T+N10C, K61T+ N16C, K61T+E38C, K61T+S65C, K61T+N83C, K61T+ K94C, K61T+N104C, K61T+A124C, S65N+Q67T+N10C, S65N+Q67T+N16C, S65N+Q67T+E38C, S65N+Q67T+ S65C, S65N+Q67T+N83C, S65N+Q67T+K94C, S65N+ Q67T+N104C, S65N+Q67T+A124C, N85T+N10C, N85T+ N16C, N85T+E38C, N85T+N59C, N85T+S65C, N85T+ K94C, N85T+N104C, N85T+A124C, K94N+N10C, K94N+N16C, K94N+E38C, K94N+N59C, K94N+S65C, K94N+N83C, K94N+N104C, K94N+A 124C, Q106T+ N10C, Q106T+N16C, Q106T+E38C, Q106T+N59C, Q106T+S65C, Q106T+N83C, Q106T+K94C and Q106T+ A124C.

50. The variant according to claim 49, wherein said variant comprises substitutions selected from the group consisting of E38N+S40T+N10C, E38N+S40T+N16C, E38N+S40T+N59C, E38N+S40T+S65C, E38N+S40T+ N83C, E38N+S40T+K94C, E38N+S40T+N104C and E38N+S40T+A124C.

51. The variant according to claim 49, wherein said cysteine residue is covalently attached to a non-polypeptide moiety.

52. The variant according to claim 51, wherein said non-polypeptide moiety is a polymer molecule.

53. The variant according to claim 52, wherein said polymer molecule is a linear polyethylene glycol or a branched polyethylene glycol.

54. A pharmaceutical composition comprising a polypeptide of SEQ ID NO: 12 and a pharmaceutically acceptable carrier, excipient or diluent.

55. A pharmaceutical composition comprising the variant of claim 39, and a pharmaceutically acceptable carrier, excipient or diluent.

56. A pharmaceutical composition comprising the variant of claim 53, and a pharmaceutically acceptable carrier, excipient or diluent.

57. The variant of claim 1 having an amino acid sequence consisting of (i) the amino acid sequence shown in SEQ ID NO: 12; or (ii) an amino acid sequence with 1 to 10 residue modifications relative to the amino acid sequence shown in SEQ ID NO: 12.

* * * * *

UNITED STATES PATENT AND TRADEMARK OFFICE
CERTIFICATE OF CORRECTION

PATENT NO. : 6,958,388 B2  Page 1 of 1
APPLICATION NO. : 10/195707
DATED : October 25, 2005
INVENTOR(S) : Van Den Hazel et al.

It is certified that error appears in the above-identified patent and that said Letters Patent is hereby corrected as shown below:

Cover Page, item [73] Assignee,

"Maxygen ApS, Horsholm (DK)" should be changed to -- Maxygen Holdings, Ltd., Grand Cayman (KY) --

Signed and Sealed this

Twenty-third Day of September, 2008

JON W. DUDAS
*Director of the United States Patent and Trademark Office*

SEQUENCE LISTING

<160> NUMBER OF SEQ ID NOS: 51

<210> SEQ ID NO 1
<211> LENGTH: 143
<212> TYPE: PRT
<213> ORGANISM: Artificial Sequence
<220> FEATURE:
<223> OTHER INFORMATION: Description of Artificial Sequence:
      [S99T]huIFNG

<400> SEQUENCE: 1

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
        50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                85                  90                  95

Asn Tyr Thr Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala Ser Gln
        130                 135                 140

<210> SEQ ID NO 2
<211> LENGTH: 142
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 2

Gln Asp Pro Tyr Val Lys Glu Ala Glu Asn Leu Lys Lys Tyr Phe Asn

```
          1               5                  10                 15
Ala Gly His Ser Asp Val Ala Asp Asn Gly Thr Leu Phe Leu Gly Ile
              20                  25                  30

Leu Lys Asn Trp Lys Glu Glu Ser Asp Arg Lys Ile Met Gln Ser Gln
              35                  40                  45

Ile Val Ser Phe Tyr Phe Lys Leu Phe Lys Asn Phe Lys Asp Asp Gln
         50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Thr Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
             115                 120                 125

Arg Lys Arg Ser Gln Met Leu Phe Arg Gly Arg Arg Ala Ser
       130                 135                 140
```

<210> SEQ ID NO 3
<211> LENGTH: 141
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 3

```
Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
              20                  25                  30

Leu Lys Asn Trp Lys Glu Glu Ser Asp Arg Lys Ile Met Gln Ser Gln
              35                  40                  45

Ile Val Ser Phe Tyr Phe Lys Leu Phe Lys Asn Phe Lys Asp Asp Gln
         50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Thr Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
             115                 120                 125

Arg Lys Arg Ser Gln Met Leu Phe Arg Gly Arg Arg Ala
       130                 135                 140
```

<210> SEQ ID NO 4
<211> LENGTH: 140
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 4

```
Gln Asp Pro Tyr Val Lys Glu Ala Glu Asn Leu Lys Lys Tyr Phe Asn
 1               5                  10                  15

Ala Gly His Ser

```
                    20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Thr Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg
    130                 135                 140

<210> SEQ ID NO 5
<211> LENGTH: 139
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 5

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln

```
                35                  40                  45
Ile Val Ser Phe Tyr Phe Lys Leu Phe Lys Asn Phe Lys Asp Asp Gln
         50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Thr Val Thr Asp Leu Asn Val Gln Arg Lys Ala Ile His Glu
             100                 105                 110

Leu Ile Gln Val Met Ala Glu Leu Ser Pro Ala Ala Lys Thr Gly Lys
         115                 120                 125

Arg Lys Arg Ser Gln Met Leu Phe Arg Gly
 130                 135

<210> SEQ ID NO 7
<211> LENGTH: 137
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 7

Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
     50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Thr Val Thr Asp Leu Asn Val Gln Arg Lys Ala Ile His Glu
             100                 105                 110

Leu Ile Gln Val Met Ala Glu Leu Ser Pro Ala Ala Lys Thr Gly Lys
         115                 120                 125

Arg Lys Arg Ser Gln Met Leu Phe Arg
 130                 135

<210> SEQ ID NO 8
<211> LENGTH: 136
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 8

Gln Asp Pro Tyr Val L

```
                50                   55                   60
Ser Ile Gln Lys Ser Val Glu Thr Ile Lys Glu Asp Met Asn Val Lys
 65                  70                   75                   80

Phe Phe Asn Ser Asn Lys Lys Lys Arg Asp Asp Phe Glu Lys Leu Thr
                 85                   90                   95

Asn Tyr Thr Val Thr Asp Leu Asn Val Gln Arg Lys Ala Ile His Glu
                100                  105                  110

Leu Ile Gln Val Met Ala Glu Leu Ser Pro Ala Ala Lys Thr Gly Lys
            115                  120                  125

Arg Lys Arg Ser Gln Met Leu Phe
        130                 135

<210> SEQ ID NO 9
<211> LENGTH: 135
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 9

Gln Asp Pro Tyr Val Lys Glu Ala Glu Asn Leu Lys Lys Tyr Phe Asn
 1               5                   10                  15

Ala Gly His Ser Asp Val Ala Asp Asn Gly Thr Leu Phe Leu Gly Ile
                20                   25                  30

Leu Lys Asn Trp Lys Glu Glu Ser Asp Arg Lys Ile Met Gln Ser Gln
            35                   40                  45

Ile Val Ser Phe Tyr Phe Lys Leu Phe Lys Asn Phe Lys Asp Asp Gln
        50                   55                  60

Ser Ile Gln Lys Ser Val Glu Thr Ile Lys Glu Asp Met Asn Val Lys
 65                  70                   75                   80

Phe Phe Asn Ser Asn Lys Lys Lys Arg Asp Asp Phe Glu Lys Leu Thr
                 85                   90                   95

Asn Tyr Thr Val Thr Asp Leu Asn Val Gln Arg Lys Ala Ile His Glu
                100                  105                  110

Leu Ile Gln Val Met Ala Glu Leu Ser Pro Ala Ala Lys Thr Gly Lys
            115                  120                  125

Arg Lys Arg Ser Gln Met Leu
        130                 135

<210> SEQ ID NO 10
<211> LENGTH: 134
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 10

Gln Asp Pro Tyr Val Lys Glu Ala Glu Asn Leu Lys Lys Tyr Phe Asn
 1               5

```
                65                  70                  75                  80
Phe Phe Asn Ser Asn Lys Lys Arg Asp Asp Phe Glu Lys Leu Thr
                    85                  90                  95
Asn Tyr Thr Val Thr Asp Leu Asn Val Gln Arg Lys Ala Ile His Glu
                100                 105                 110
Leu Ile Gln Val Met Ala Glu Leu Ser Pro Ala Ala Lys Thr Gly Lys
            115                 120                 125
Arg Lys Arg Ser Gln Met
    130

<210> SEQ ID NO 11
<211> LENGTH: 133
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 11

Gln Asp Pro Tyr Val Lys Glu Ala Glu Asn Leu Lys Lys Tyr Phe Asn
  1               5                  10                  15
Ala Gly His Ser Asp Val Ala Asp Asn Gly Thr Leu Phe Leu Gly Ile
                 20                  25                  30
Leu Lys Asn Trp Lys Glu Glu Ser Asp Arg Lys

```
                    85                  90                  95
Asn Tyr Thr Val Thr Asp Leu Asn Val Gln Arg Lys Ala Ile His Glu
                100                 105                 110
Leu Ile Gln Val Met Ala Glu Leu Ser Pro Ala Ala Lys Thr Gly Lys
            115                 120                 125
Arg Lys Arg Ser
    130

<210> SEQ ID NO 13
<211> LENGTH: 131
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 13

Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Lys Arg Asp Asp Phe Glu Lys Leu Thr
                 85                  90                  95

Asn Tyr Thr Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg
    130

<210> SEQ ID NO 14
<211> LENGTH: 130
<212> TYPE: PRT
<213> ORGANISM: Artificial Sequence
<220> FEATURE:
<223> OTHER INFORMATION: Description of Artificial Sequence:
      C-terminally truncated [S99T]huIFG

<400> SEQUENCE: 14

Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Lys Arg Asp Asp Phe Glu Lys Leu Thr
                 85                  90                  95

Asn Tyr Thr Val Thr Asp Leu Asn Val Gln Arg Lys Ala Ile His Glu
```

```
                100               105               110
Leu Ile Gln Val Met Ala Glu Leu Ser Pro Ala Ala Lys Thr Gly Lys
        115               120               125

Arg Lys
    130
```

<210> SEQ ID NO 15
<211> LENGTH: 129
<212> TYPE: PRT
<213> ORGANISM: Artificial Sequence
<220> FEATURE:
<223> OTHER INFORMATION: Description of Artificial Sequence:
      C-terminally truncated [S99T]huIFNG

<400> SEQUENCE: 15

```
Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
                 20                  25                  30

Leu Lys Asn Trp Lys Glu Glu Ser Asp Arg Lys Ile Met Gln Ser Gln
             35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Gl

<210> SEQ ID NO 17
<211> LENGTH: 143
<212> TYPE: PRT
<213> ORGANISM: Homo sapiens

<400> SEQUENCE: 17

```
Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
     50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala Ser Gln
        130                 135                 140
```

<210> SEQ ID NO 18
<211> LENGTH: 166
<212> TYPE: PRT
<213> ORGANISM: Homo sapiens

<400> SEQUENCE: 18

```
Met Lys Tyr Thr Ser Tyr Ile Leu Ala Phe Gln Leu Cys Ile Val Leu
  1               5                  10                  15

Gly Ser Leu Gly Cys Tyr Cys Gln Asp Pro Tyr Val Lys Glu Ala Glu
             20                  25                  30

Asn Leu Lys Lys Tyr Phe Asn Ala Gly His Ser Asp Val Ala Asp Asn
         35                  40                  45

Gly Thr Leu Phe Leu Gly Ile Leu Lys Asn Trp Lys Glu Glu Ser Asp
     50                  55                  60

Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
                100                 105                 110

Asp Asp Phe Glu Lys Leu Thr Asn Tyr Ser Val Thr Asp Leu Asn Val
            115                 120                 125

Gln Arg Lys Ala Ile His Glu Leu Ile Gln Val Met Ala Glu Leu Ser
        130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```

<210> SEQ ID NO 19

```
<211> LENGTH: 142
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 19

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala Ser
        130                 135                 140

<210> SEQ ID NO 20
<211> LENGTH: 141
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 20

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala
        130                 135                 140

<210> SEQ ID NO 21
<211> LENGTH: 140
<212> TYPE: PRT
<213> ORGANISM: Artificial Sequence
```

<220> FEATURE:
<223> OTHER INFORMATION: Description of Artificial Sequence:
    C-terminally truncated huIFNG

<400> SEQUENCE: 21

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
     50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg
        130                 135                 140

<210> SEQ ID NO 22
<211> LENGTH: 139
<212> TYPE: PRT
<213> ORGANISM: Artificial Sequence
<220> FEATURE:
<223> OTHER INFORMATION: Description of Artificial Sequence:
    C-terminally truncated huIFNG

<400> SEQUENCE: 22

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
     50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg
        130                 135

<210> SEQ ID NO 23
<211> LENGTH: 138
<212> TYPE: PRT
<213> ORGANISM: Artificial Sequence
<220> FEATURE:
<223> OTHER INFORMATION: Description of Artificial Sequence:
    C-terminally truncated huIFNG

```
<400> SEQUENCE: 23

Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly
        130                 135

<210> SEQ ID NO 24
<211> LENGTH: 137
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 24

Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg
        130                 135

<210> SEQ ID NO 25
<211> LENGTH: 136
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 25
```

```
Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
     50                  55                  60

Ser Ile Gln Lys Ser Val Glu Thr Ile Lys Glu Asp Met Asn Val Lys
 65                  70                  75                  80

Phe Phe Asn Ser Asn Lys Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe
        130                 135

<210> SEQ ID NO 26
<211> LENGTH: 135
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 26

Gln Asp Pro Tyr Val Lys Glu Ala Glu Asn Leu Lys Lys Tyr Phe Asn
  1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
     50                  55                  60

Ser Ile Gln Lys Ser Val Glu Thr Ile Lys Glu Asp Met Asn Val Lys
 65                  70                  75                  80

Phe Phe Asn Ser Asn Lys Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu
        130                 135

<210> SEQ ID NO 27
<211> LENGTH: 134
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 27

Gln Asp Pro Tyr Val Lys Glu Ala Glu Asn Leu Lys Lys Tyr Phe Asn
  1               5                  10                  15
```

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met
    130

<210> SEQ ID NO 28
<211> LENGTH: 133
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 28

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln
    130

<210> SEQ ID NO 29
<211> LENGTH: 132
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 29

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

-continued

```
Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser
        130
```

<210> SEQ ID NO 30
<211> LENGTH: 131
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 30

```
Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
 50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg
        130
```

<210> SEQ ID NO 31
<211> LENGTH: 130
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 31

```
Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45
```

```
Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
        115                 120                 125

Arg Lys
    130

<210> SEQ ID NO 32
<211> LENGTH: 129
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 32

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
        115                 120                 125

Arg

<210> SEQ ID NO 33
<211> LENGTH: 128
<212> TYPE: PRT
<213> ORGANISM: Artificial Sequence
<220> FEATURE:
<223> OTHER INFORMATION: Description of Artificial Sequence:
      C-terminally truncated huIFNG

<400> SEQUENCE: 33

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
```

```
                65                  70                  75                  80
        Phe Phe Asn Ser Asn Lys Lys Arg Asp Asp Phe Glu Lys Leu Thr
                        85                  90                  95

Asn Tyr Ser Val Thr Asp Leu Asn Val Gln Arg Lys Ala Ile His Glu
                    100                 105                 110

Leu Ile Gln Val Met Ala Glu Leu Ser Pro Ala Ala Lys Thr Gly Lys
                115                 120                 125

<210> SEQ ID NO 34
<211> LENGTH: 140
<212> TYPE: PRT
<213> ORGANISM: Artificial Sequence
<220> FEATURE:
<223> OTHER INFORMATION: Description of Artificial Sequence:
      Actimmune(r)

<400> SEQUENCE: 34

Met Gln Asp Pro Tyr Val Lys Glu Ala Glu Asn Leu Lys Lys Tyr Phe
 1               5                  10                  15

Asn Ala Gly His Ser Asp Val Ala Asp Asn Gly Thr Leu Phe Leu Gly
                20                  25                  30

Ile Leu Lys Asn Trp Lys Glu Glu Ser Asp Arg Lys Ile Met Gln Ser
            35                  40                  45

Gln Ile Val Ser Phe Tyr Phe Lys Leu Phe Lys Asn Phe Lys Asp Asp
        50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Arg Asp Asp Phe Glu Lys Leu
                85                  90                  95

Thr Asn Tyr Ser Val Thr Asp Leu Asn Val Gln Arg Lys Ala Ile His
                    100                 105                 110

Glu Leu Ile Gln Val Met Ala Glu Leu Ser Pro Ala Ala Lys Thr Gly
                115                 120                 125

Lys Arg Lys Arg Ser Gln Met Leu Phe Arg Gly Arg
        130                 135                 140

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Tag

<400> SEQUENCE: 35

His His His His His His
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Tag

<400> SEQUENCE: 36

Met Lys His His His His His His
 1               5

<210> SEQ ID NO 37
<211> LENGTH: 10
<212> TYPE: PRT
```

```
<213> ORGANISM: Artificial Sequence
<220> FEATURE:
<223> OTHER INFORMATION: Description of Artificial Sequence: Tag

<400> SEQUENCE: 37

Met Lys His His Ala His His Gln His His
 1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Tag

<400> SEQUENCE: 38

Met Lys His Gln His Gln His Gln His Gln His Gln His Gln
 1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Tag

<400> SEQUENCE: 39

Glu Gln Lys Leu Ile Ser Glu Glu Asp Leu
 1               5                   10

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Tag

<400> SEQUENCE: 40

Asp Tyr Lys Asp Asp Asp Asp Lys
 1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Tag

<400> SEQUENCE: 41

Tyr Pro Tyr Asp Val Pro Asp Tyr Ala
 1               5

<210> SEQ ID NO 42
<211> LENGTH: 498
<212> TYPE: DNA
<213> ORGANISM: Artificial Sequence
<220> FEATURE:
<223> OTHER INFORMATION: Description of Artificial Sequence: Expression
      casette optimised for expression of interferon
      gamma in CHO cells

<400> SEQUENCE: 42
atgaagtaca caagctatat cctggccttt cagctgtgca tcgtgctggg ctccctgggc      60
tgctattgcc aggacccctta cgtgaaggag gccgagaacc tgaagaagta ctttaacgcc    120
ggccacagcg atgtggccga caatggcaca ctgtttctgg catcctgaa gaattggaag    180
```

```
gaggagagcg atcggaagat catgcagtcc cagatcgtgt ccttctattt caagctgttt      240
aagaatttca aggacgatca gtccatccag aagtccgtgg agaccatcaa ggaggacatg      300
aacgtgaagt ttttcaatag caataagaag aagagagacg atttcgagaa gctgaccaat      360
tactccgtga cagacctgaa cgtgcagaga aaggccatcc acgagctgat ccaggtgatg      420
gccgagctgt cccccgccgc caagaccggc aagagaaaga gaagccagat gctgttcaga      480
ggcagacggg ccagccag                                                    498
```

```
<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 43
gatggctggc aactagaag                                                   19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 44
tgtacggtgg gaggtctat                                                   19

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 45
gttcaggtct gtcacgctgt aattggtcag ctt                                   33

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 46
aagctgacca attaccgt gacagacctg aac                                     33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 47
catgatcttc cgatcggtct cgttcttcca att                                   33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Primer
```

```
<400> SEQUENCE: 48
aattggaaga acgagaccga tcggaagatc atg                                    33

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 49
gagtctagat tacagcatct ggcttctctt                                        30

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 50
cacggatccg ccgccaccat gaagtacaca agctatatcc tg                          42

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 51
tcatctagat tagcttctct ttctcttgcc gg                                     32
```